United States Patent
Aebi et al.

(10) Patent No.: US 8,592,426 B2
(45) Date of Patent: Nov. 26, 2013

(54) ARYL-BENZOCYCLOALKYL AMIDE DERIVATIVES

(75) Inventors: Johannes Aebi, Binningen (CH); Alfred Binggeli, Binningen (CH); Cornelia Hertel, Brislach (CH); Anish Ashok Konkar, Binningen (CH); Holger Kuehne, Loerrach (DE); Bernd Kuhn, Reinach BL (CH); Hans P. Maerki, Basel (CH); Haiyan Wang, Allschwil (CH)

(73) Assignee: Hoffmann—La Roche Inc., Nutley, NJ (US)

( * ) Notice: Subject to any disclaimer, the term of this patent is extended or adjusted under 35 U.S.C. 154(b) by 8 days.

(21) Appl. No.: 13/351,253

(22) Filed: Jan. 17, 2012

(65) Prior Publication Data
US 2013/0018055 A1 Jan. 17, 2013

(30) Foreign Application Priority Data
Jan. 24, 2011 (EP) .................... 11151890

(51) Int. Cl.
*A61K 31/24* (2006.01)
*A61K 31/42* (2006.01)
*C07D 271/06* (2006.01)

(52) U.S. Cl.
USPC ...... 514/252.05; 544/510; 544/340; 544/256; 544/364; 548/131; 546/112; 560/68

(58) Field of Classification Search
None
See application file for complete search history.

(56) References Cited

FOREIGN PATENT DOCUMENTS

| WO | 03/097610 | 11/2003 |
|---|---|---|
| WO | 2004/019868 | 3/2004 |
| WO | 2010/097374 | 9/2010 |

OTHER PUBLICATIONS (International Search Report in Corres PCT/EP2012/050667 Jul. 23,2012).
Goodman et al., "The Pharmacological Basis of Therapeutics" 7:35-48 ( 1985).

*Primary Examiner* — Bong-Sook Baek
*Assistant Examiner* — Taina D Matos Negron

(57) ABSTRACT

The invention provides novel compounds having the general formula (I)

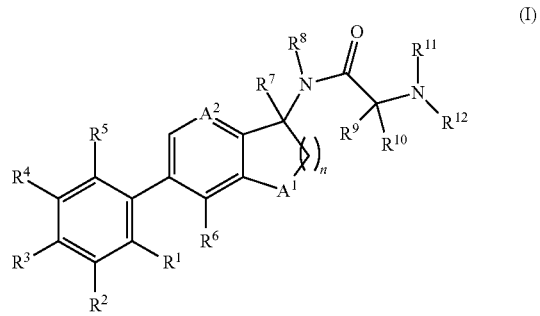

wherein $R^1, R^2, R^3, R^4, R^5, R^6, R^7, R^8, R^9, R^{10}, R^{11}, R^{12}, A^1, A^2$ and n are as described herein, compositions including the compounds and methods of using the compounds.

29 Claims, No Drawings

ARYL-BENZOCYCLOALKYL AMIDE DERIVATIVES

PRIORITY TO RELATED APPLICATION(S)

This application claims the benefit of European Patent Application No. 11151890.8, filed Jan. 24, 2011, which is hereby incorporated by reference in its entirety.

FIELD OF THE INVENTION

The present invention relates to organic compounds useful for therapy or prophylaxis in a mammal, and in particular to bradykinin B1-receptor (BDKRB1 or B1R) antagonists or inverse agonists for the treatment or prophylaxis of glomerulonephritides, Henoch-Schönlein purpura nephropathy (HSPN), ANCA-associated crescentic glomerulonephritis, lupus nephritis and IgA nephritis.

BACKGROUND OF THE INVENTION

Kinins belong to a family of bioactive octa- to decapeptides generated from the inactive precursor kininogen in a stepwise proteolytic process in body fluids and tissues. Kinins are hormones formed by a group of 9-11 amino acid peptides, including bradykinin (BK), kallidin (KD/Lys-BK), and their active metabolites (des-Arg$^9$-BK and des-Arg$^{10}$-kallidin/Lys-des-Arg$^9$-BK). The kinins play an important physiological role in inflammatory and nociceptive processes. The biological effects of BK and other kinins are mediated by two physiologically distinct G protein-couple receptors (GPCRs), termed BDKRB1 (B1R) and BDKRB2 (B2R). It is believed that under physiological conditions, the constitutively expressed B2R mediates the effects of circulating or locally generated kinins, since B1R is not expressed in normal tissues. The B2R is constitutively expressed in numerous cell types of the central and peripheral nervous systems, the vascular endothelium and inflammatory cells, and is activated by the short lived natural ligands, BK and kallidin (KD). Once synthesized, BK causes vasodilatation and increased vascular permeability by interaction with B2Rs. However, B2Rs are rapidly desensitized and internalized following binding and activation by the endogenous ligands. Catalytic degradation of kinins by enzymes including carboxypeptidase N and carboxypeptidase M yields des-Arg$^9$-BK (DABK) and des-Arg$^{10}$-kallidin/Lys-des-Arg$^9$-BK, which preferentially activate the B1R. Although not expressed in normal tissues (or expressed at very low levels), the B1R is rapidly induced following bacterial infections, tissue injury and release of inflammatory mediators, and has been observed in sympathetic neurons, macrophages, fibroblasts, smooth muscle cells, and the vascular endothelium. The endogenous B1R agonists, including des-Arg$^9$-BK and des-Arg$^{10}$-kallidin/Lys-des-Arg$^9$-BK, are relatively long-lasting peptides. Moreover, the B1R does not undergo rapid desensitization and internalization after stimulation. Once upregulated, B1R activity persists in damaged or inflamed tissues and is thought to participate in prolonging the pathological response to kinins. Thus, the B1R has been implicated in maintaining chronic pain, vasodilation, plasma extravasation, neutrophil recruitment and further release of inflammatory mediators, such as IL-β, TNF-α and IL-6 which sustain a positive feedback loop between B1R expression and inflammation. The proposed upregulation of B1R only under pathological conditions, including inflammation, trauma, burns, shock, and allergy, makes B1R a particularly attractive drug target.

The proposed role of kinins in mediating pain and inflammation has propelled interest in the discovery of potent and selective BK antagonists. Recent evidence suggests that bradykinin receptors may also play an important role in a number of pathological processes or diseases, including ischemia-reperfusion injury, diabetic retinopathy, atherosclerosis, renal disease. Hence, there is an urgent need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools.

SUMMARY OF THE INVENTION

The present invention relates to compounds according to formula (I)

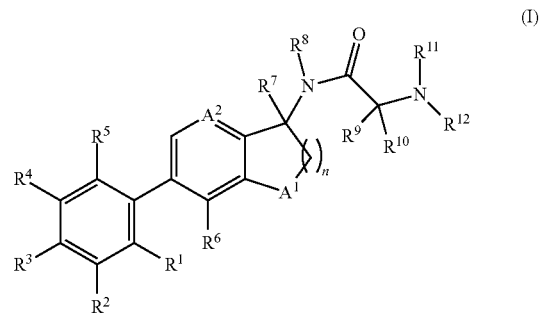

wherein
$R^1$ is selected from the group consisting of alkyl, cycloalkyl, cycloalkylalkyl, alkoxy, alkoxyalkyl, cycloalkoxy, cycloalkoxyalkyl, haloalkyl, haloalkoxy, haloalkoxyalkyl, halocycloalkyl, halocycloalkylalkyl, halocycloalkoxy, halocycloalkoxyalkyl, alkoxycarbonyl, cycloalkoxycarbonyl, haloalkoxycarbonyl, halocycloalkoxycarbonyl, cyano, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, alkoxy, alkoxyalkyl, haloalkoxy, alkoxyalkoxy, alkoxyalkoxyalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;
$R^2$ is selected from the group consisting of hydrogen, alkyl, haloalkyl, alkoxy, cycloalkyl, cyano and halogen;
$R^3$ is selected from the group consisting of hydrogen, alkyl, haloalkyl, alkoxy, cycloalkyl, cyano and halogen;
$R^4$ is selected from the group consisting of hydrogen, alkyl, haloalkyl, alkoxy, cycloalkyl, cyano and halogen;

$R^5$ is selected from the group consisting of hydrogen, alkyl, haloalkyl, alkoxy, cycloalkyl, cyano and halogen;

$R^6$ is selected from the group consisting of hydrogen, alkyl, haloalkyl, alkoxy, cycloalkyl, cyano and halogen;

$R^7$ is selected from the group consisting of hydrogen, alkyl and cycloalkyl;

$R^8$ is selected from the group consisting of hydrogen, alkyl and cycloalkyl;

$R^9$ is selected from the group consisting of hydrogen, alkyl and cycloalkyl;

$R^{10}$ is selected from the group consisting of hydrogen, alkyl and cycloalkyl;

or $R^9$ and $R^{10}$ together with the carbon they are attached to form a cycloalkyl or a heterocycloalkyl;

$R^{11}$ is selected from the group consisting of hydrogen, alkyl and cycloalkyl;

$R^{12}$ is selected from the group consisting of hydrogen, alkyl, cycloalkyl and —C(O)—$R^{13}$;

$R^{13}$ is selected from the group consisting of alkyl, cycloalkyl, cycloalkylalkyl, alkoxy, alkoxyalkoxy, cycloalkoxy, halocycloalkoxy, alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;

$R^{14}$ is selected from the group consisting of hydrogen, alkyl, alkoxy and cycloalkyl;

$R^{15}$ is selected from the group consisting of hydrogen, alkyl and cycloalkyl;

$R^{16}$ is selected from the group consisting of hydrogen, alkyl, haloalkyl, alkoxy, cycloalkyl, cyano and halogen;

$A^1$ is selected from the group consisting of $CR^{14}$, O, $NR^{15}$ and S;

$A^2$ is $CR^{16}$ or N; and n is 1, 2 or 3;

and to pharmaceutically acceptable salts thereof.

The present invention also relates to a pharmaceutical composition comprising a compound as described above and a therapeutically inert carrier.

DETAILED DESCRIPTION OF THE INVENTION

The present invention relates to compounds according to formula (I)

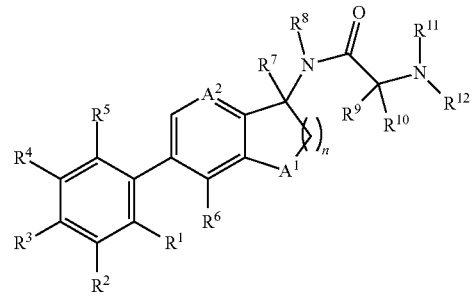

wherein $R^1$ is selected from the group consisting of alkyl, cycloalkyl, cycloalkylalkyl, alkoxy, alkoxyalkyl, cycloalkoxy, cycloalkoxyalkyl, haloalkyl, haloalkoxy, haloalkoxyalkyl, halocycloalkyl, halocycloalkylalkyl, halocycloalkoxy, halocycloalkoxyalkyl, alkoxycarbonyl, cycloalkoxycarbonyl, haloalkoxycarbonyl, halocycloalkoxycarbonyl, cyano, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, alkoxy, alkoxyalkyl, haloalkoxy, alkoxyalkoxy, alkoxyalkoxyalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;

$R^2$ is selected from the group consisting of hydrogen, alkyl, haloalkyl, alkoxy, cycloalkyl, cyano and halogen;

$R^3$ is selected from the group consisting of hydrogen, alkyl, haloalkyl, alkoxy, cycloalkyl, cyano and halogen;

$R^4$ is selected from the group consisting of hydrogen, alkyl, haloalkyl, alkoxy, cycloalkyl, cyano and halogen;

$R^5$ is selected from the group consisting of hydrogen, alkyl, haloalkyl, alkoxy, cycloalkyl, cyano and halogen;

$R^6$ is selected from the group consisting of hydrogen, alkyl, haloalkyl, alkoxy, cycloalkyl, cyano and halogen;

$R^7$ is selected from the group consisting of hydrogen, alkyl and cycloalkyl;

$R^8$ is selected from the group consisting of hydrogen, alkyl and cycloalkyl;

$R^9$ is selected from the group consisting of hydrogen, alkyl and cycloalkyl;

$R^{10}$ is selected from the group consisting of hydrogen, alkyl and cycloalkyl;

or $R^9$ and $R^{10}$ together with the carbon they are attached to form a cycloalkyl or a heterocycloalkyl;

$R^{11}$ is selected from the group consisting of hydrogen, alkyl and cycloalkyl;

$R^{12}$ is selected from the group consisting of hydrogen, alkyl, cycloalkyl and —C(O)—$R^{13}$;

$R^{13}$ is selected from the group consisting of alkyl, cycloalkyl, cycloalkylalkyl, alkoxy, alkoxyalkoxy, cycloalkoxy, halocycloalkoxy, alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkyloxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;

$R^{14}$ is selected from the group consisting of hydrogen, alkyl, alkoxy and cycloalkyl;

$R^{15}$ is selected from the group consisting of hydrogen, alkyl and cycloalkyl;

$R^{16}$ is selected from the group consisting of hydrogen, alkyl, haloalkyl, alkoxy, cycloalkyl, cyano and halogen;

$A^1$ is selected from the group consisting of $CR^{14}$, O, $NR^{15}$ and S;

$A^2$ is $CR^{16}$ or N; and n is 1, 2 or 3;

and to pharmaceutically acceptable salts thereof.

The present invention also relates to a pharmaceutical composition comprising a compound as described above and a therapeutically inert carrier.

As described herein, the compounds of formula (I) are antagonists or inverse agonists of the bradykinin-receptor, in particular the bradykinin B1-receptor (B1R), and as such are useful in the treatment and prevention of diseases and conditions mediated through the stimulation of bradykinin receptor pathway such as pain, inflammation, vasodilation, plasma extravasation, neutrophil recruitment, macrophage infiltration and further release of inflammatory mediators, such as IL-β and TNF-α.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of glomerulonephritides, Henoch-Schönlein purpura nephropathy (HSPN), ANCA-associated crescentic glomerulonephritis, lupus nephritis and IgA nephritis and the use of the said compounds, salts or esters for the production of medicaments for the treatment or prophylaxis of glomerulonephritides, Henoch-Schönlein purpura nephropathy (HSPN), ANCA-associated crescentic glomerulonephritis, lupus nephritis and IgA nephritis.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "antagonist" denotes a compound that diminishes or prevents the action of another compound or receptor site as defined e.g. in Goodman and Gilman's "The Pharmacological Basis of Therapeutics, 7th ed." in page 35, Macmillan Publ. Company, Canada, 1985. In particular, antagonists refers to a compound that attenuates the effect of an agonist. A "competitive antagonist" binds to the same site as the agonist but does not activate it, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy and ethoxy. More particular alkoxy group is methoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxymethyl, ethoxyethyl, methoxypropyl and ethoxypropyl. Particular alkoxyalkyl group include methoxymethyl and methoxyethyl. More particular alkoxyalkyl group is methoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy or ethoxy. Particular alkoxycarbonyl group is a group of the formula —C(O)—R', wherein R' is methoxy.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, and tert-butyl. Particular alkyl groups include methyl or ethyl. More particular alkyl group is methyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethylcyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "amino" denotes a —NH$_2$ group.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkoxycarbonyl" denotes a group of the formula —C(O)—R', wherein R' is a cycloalkoxy group. Examples of cycloalkoxycarbonyl groups include groups of the formula —C(O)—R', wherein R' is cyclopropoxy, cyclobutoxy, cyclopentyloxy, cyclohexyloxy, cycloheptyloxy and cyclooctyloxy. Particular cycloalkoxycarbonyl group is a group of the formula —C(O)—R', wherein R' is cyclopropoxy.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and 2,2-difluoroethoxy. More particular haloalkoxy group is 2,2-difluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl.

The term "haloalkoxycarbonyl" denotes a group of the formula —C(O)—R', wherein R' is an haloalkoxy group. Examples of haloalkoxycarbonyl groups include a group of the formula —C(O)—R', wherein R' is fluoromethoxy, difluoromethoxy, trifluoromethoxy, trifluoroethoxy, trifluoromethylethoxy, trifluorodimethylethoxy or pentafluoroethoxy.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halocycloalkoxy" denotes a cycloalkoxy group wherein at least one of the hydrogen atoms of the cycloalkoxy group has been replaced by same or different halogen atoms, particularly fluoro atoms. Examples of halocycloalkoxyl include fluorocyclopropoxy, difluorocyclopropoxy, fluorocyclobutoxy and difluorocyclobutoxy.

The term "halocycloalkoxyalkyl" denotes an alkyl group wherein at least one of the hydrogen atoms of the alkyl group has been replaced by a halocycloalkoxy. Examples of halocycloalkoxyalkyl include fluorocyclopropoxymethyl, difluorocyclopropoxymethyl, fluorocyclopropoxyethyl, difluorocyclopropoxyethyl, fluorocyclobutoxymethyl, difluorocyclobutoxymethyl, fluorocyclobutoxyethyl and difluorocyclobutoxyethyl.

The term "halocycloalkoxycarbonyl" denotes a group of the formula —C(O)—R', wherein R' is an halocycloalkoxy group. Examples of halocycloalkoxycarbonyl groups include groups of the formula —C(O)—R', wherein R' is fluorocyclopropoxymethyl, difluorocyclopropoxymethyl, fluorocyclopropoxyethyl, difluorocyclopropoxyethyl, fluorocyclobutoxymethyl, difluorocyclobutoxymethyl, fluorocyclobutoxyethyl and difluorocyclobutoxyethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, isoxazolyl and isothiazolyl. More particular heteroaryl groups include imidazolyl, oxazolyl, thiazolyl, oxadiazolyl, thiadiazolyl, tetrazolyl, pyridinyl, pyrazinyl, pyrazolyl, pyridazinyl, pyrimidinyl, isoxazolyl and isothiazolyl. Further particular examples of heteroaryl groups in the definition of $R^1$ substituent include oxadiazolyl and tetrazolyl. Further particular examples of heteroaryl groups in the definition of $R^{13}$ substituent include oxadiazolyl, tetrazolyl, pyridazinyl, pyrimidinyl and isoxazolyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are oxetanyl, azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Further particular example of heterocycloalkyl group is oxetanyl.

The term "hydroxy" denotes a —OH group.

The term "hydroxyalkoxy" an alkoxy group wherein at least one of the hydrogen atoms of the alkoxy group has been replaced by a hydroxy group. Examples of hydroxyalkoxy include hydroxyethoxy, hydroxypropoxy, hydroxymethylpropoxy and dihydroxypropoxy.

The term "hydroxyhaloalkyl" denotes an alkyl wherein at least one of the hydrogen atoms of the alkyl has been replaced by a hydroxy group and wherein at least one of the hydrogen atoms of the alkyl has been replaced by a halogen. Examples of hydroxyhaloalkyl include hydroxytrifluoroethyl, hydroxytrifluoropropyl and hydroxyhexafluoropropyl.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A further embodiment of the present invention are compounds according to formula (I) as described herein, wherein $R^1$ is selected from the group consisting of haloalkoxy, alkoxycarbonyl, cycloalkoxycarbonyl, haloalkoxycarbonyl, heteroaryl and substituted heteroaryl, wherein substituted heteroaryl is substituted with one to three alkyl.

A particular embodiment of the present invention are compounds according to formula (I) as described herein, wherein $R^1$ is selected from the group consisting of haloalkoxy, alkoxycarbonyl and substituted heteroaryl, wherein substituted heteroaryl is substituted with one to three alkyl.

In a further embodiment of the present invention are compounds according to formula (I) as described herein, wherein $R^1$ is selected from the group consisting of haloalkoxy, alkoxycarbonyl, alkyloxadiazolyl and alkyltetrazolyl.

Another further embodiment of the present invention are compounds according to formula (I) as described herein, wherein $R^1$ is alkyloxadiazolyl.

Another embodiment of the present invention are compounds according to formula (I) as described herein, wherein $R^1$ is methyloxadiazolyl.

Another further embodiment of the present invention are compounds according to formula (I) as described herein, wherein $R^1$ is alkyltetrazolyl.

Another embodiment of the present invention are compounds according to formula (I) as described herein, wherein $R^1$ is methyltetrazolyl.

The present invention also relates to compounds according to formula (I) as described herein, wherein $R^2$ is hydrogen or halogen.

A further particular embodiment of the present invention are compounds according to formula (I) as described herein, wherein $R^2$ is halogen.

A more particular embodiment of the present invention are compounds according to formula (I) as described herein, wherein $R^2$ is chloro or fluoro.

Also an embodiment of the present invention are compounds according to formula (I) as described herein, wherein $R^3$ is hydrogen.

The present invention also relates to compounds according to formula (I) as described herein, wherein $R^4$ is hydrogen or halogen.

Another embodiment of the present invention are compounds according to formula (I) as described herein, wherein $R^4$ is halogen.

A further particular embodiment of the present invention are compounds according to formula (I) as described herein, wherein is $R^4$ is chloro.

A particular embodiment of the present invention are compounds according to formula (I) as described herein, wherein $R^5$ is hydrogen.

Also an embodiment of the present invention are compounds according to formula (I) as described herein, wherein $R^6$ is hydrogen.

The present invention also relates to compounds according to formula (I) as described herein, wherein $R^7$ is hydrogen or alkyl.

Another embodiment of the present invention are compounds according to formula (I) as described herein, wherein $R^7$ is hydrogen The present invention also relates to compounds according to formula (I) as described herein, wherein $R^8$ is hydrogen.

Also an embodiment of the present invention are compounds according to formula (I) as described herein, wherein $R^9$ is selected from the group consisting of hydrogen, alkyl and cycloalkyl.

Also an embodiment of the present invention are compounds according to formula (I) as described herein, wherein $R^{10}$ is selected from the group consisting of hydrogen, alkyl and cycloalkyl.

Another embodiment of the present invention are compounds according to formula (I) as described herein, wherein $R^9$ and $R^{10}$ together with the carbon they are attached to form a cycloalkyl or a heterocycloalkyl.

A particular embodiment of the present invention are compounds according to formula (I) as described herein, wherein $R^9$ and $R^{10}$ together with the carbon they are attached to form a cycloalkyl.

A further particular embodiment of the present invention are compounds according to formula (I) as described herein, wherein $R^9$ and $R^{10}$ together with the carbon they are attached to form a heterocycloalkyl.

A more particular embodiment of the present invention are compounds according to formula (I) as described herein, wherein $R^9$ and $R^{10}$ together with the carbon they are attached to form a cycloalkyl or an oxetanyl.

Also a particular embodiment of the present invention are compounds according to formula (I) as described herein, wherein $R^9$ and $R^{10}$ together with the carbon they are attached to form a cyclopropyl.

Also a particular embodiment of the present invention are compounds according to formula (I) as described herein, wherein $R^9$ and $R^{10}$ together with the carbon they are attached to form an oxetanyl.

Another embodiment of the present invention are compounds according to formula (I) as described herein, wherein $R^{11}$ is hydrogen.

Another embodiment of the present invention are compounds according to formula (I) as described herein, wherein $R^{12}$ is selected from the group consisting of hydrogen, alkyl and cycloalkyl.

Also an embodiment of the present invention are compounds according to formula (I) as described herein, wherein $R^{12}$ is hydrogen.

Also an embodiment of the present invention are compounds according to formula (I) as described herein, wherein $R^{12}$ is hydrogen or —C(O)—$R^{13}$.

A further embodiment of the present invention are compounds according to formula (I) as described herein, wherein $R^{12}$ is —C(O)—$R^{13}$.

Another embodiment of the present invention are compounds according to formula (I) as described herein, wherein $R^{13}$ is selected from the group consisting of alkoxy, alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, halogen, cyano, haloalkyl, alkoxy, alkoxyalkyl, amino and substituted amino, wherein substituted amino is substituted with one to two substituents independently selected from alkyl and cycloalkyl.

A further embodiment of the present invention are compounds according to formula (I) as described herein, wherein $R^{13}$ is selected from the group consisting of alkoxy, alkoxyalkyl, haloalkyl, substituted phenyl, heteroaryl and substituted heteroaryl, wherein substituted phenyl and substituted heteroaryl are substituted with one to three substituents independently selected from the group consisting of alkyl, halogen, haloalkyl, alkoxy and amino. A particular embodiment of the present invention are compounds according to formula (I) as described herein, wherein $R^{13}$ is selected from the group consisting of alkoxy, haloalkyl, heteroaryl and substituted heteroaryl, wherein substituted heteroaryl is substituted with one to three alkoxy substituents.

A further particular embodiment of the present invention are compounds according to formula (I) as described herein, wherein $R^{13}$ is selected from the group consisting of alkoxy, alkoxyalkyl, haloalkyl, imidazolyl, isoxazolyl, oxadiazolyl, thiadiazolyl, pyridinyl, pyridazinyl, and pyrimidinyl, or is selected from the group consisting of phenyl, imidazolyl, isoxazolyl, oxadiazolyl, thiadiazolyl, pyridinyl, pyridazinyl and pyrimidinyl substituted with one to three substituents independently selected from the group consisting of alkyl, halogen, haloalkyl, alkoxy and amino.

A more particular embodiment of the present invention are compounds according to formula (I) as described herein, wherein $R^{13}$ is selected from the group consisting of alkoxy, haloalkyl, isoxazolyl, oxadiazolyl, pyridazinyl, and pyrimidinyl, or is selected from isoxazolyl or oxadiazolyl substituted with one to three substituents alkoxy.

Another embodiment of the present invention are compounds according to formula (I) as described herein, wherein $R^{13}$ is selected from the group consisting of haloalkyl, alkoxyisoxazolyl, pyridazinyl and alkoxypyrimidinyl.

Another particular embodiment of the present invention are compounds according to formula (I) as described herein, wherein $R^{13}$ is selected from the group consisting of trifluoromethyl, methoxyisoxazolyl, pyridazinyl and methoxypyrimidinyl.

Another particular embodiment of the present invention are compounds according to formula (I) as described herein, wherein $R^1$ is selected from the group consisting of trifluoromethyl, methoxyisoxazolyl, pyridazinyl, pyrimidinyl and methoxypyrimidinyl.

A particular embodiment of the present invention are compounds according to formula (I) as described herein, wherein $A^1$ is selected from the group consisting of $CR^{14}$, O and S.

Also an embodiment of the present invention are compounds according to formula (I) as described herein, wherein $A^1$ is $CR^{14}$.

Another embodiment of the present invention are compounds according to formula (I) as described herein, wherein $A^1$ is O.

The present invention also relates to compounds according to formula (I) as described herein, wherein $A^1$ is S.

A further embodiment of the present invention are compounds according to formula (I) as described herein, wherein $A^1$ is $NR^{15}$.

A embodiment of the present invention are compounds according to formula (I) as described herein, wherein $A^2$ is $CR^{16}$.

Also an embodiment of the present invention are compounds according to formula (I) as described herein, wherein $A^2$ is N.

The present invention also relates to compounds according to formula (I) as described herein, wherein $R^{14}$ is hydrogen.

The present invention also relates to compounds according to formula (I) as described herein, wherein $R^{15}$ is hydrogen.

Another embodiment of the present invention are compounds according to formula (I) as described herein, wherein $R^{16}$ is hydrogen or halogen.

A further embodiment of the present invention are compounds according to formula (I) as described herein, wherein $R^{16}$ is hydrogen.

Also a further embodiment of the present invention are compounds according to formula (I) as described herein, wherein $R^{16}$ is halogen.

A particular embodiment of the present invention are compounds according to formula (I) as described herein, wherein is $R^{16}$ is fluoro.

Another embodiment of the present invention are compounds according to formula (I) as described herein, n is 1 or 2.

A further embodiment of the present invention are compounds according to formula (I) as described herein, wherein n is 1.

A further embodiment of the present invention are compounds according to formula (I) as described herein of formula (Ia)

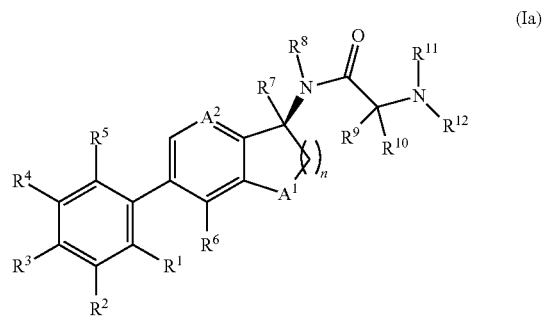

(Ia)

Also a further embodiment of the present invention are compounds according to formula (I) as described herein of formula (Ib)

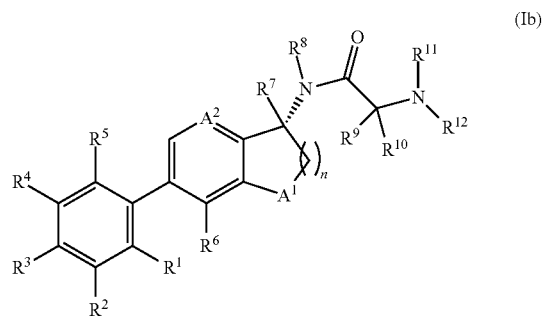

(Ib)

Particular examples of compounds of formula (I) as described herein are selected from
(rac)-2-(1-{[1-(2,2,2-Trifluoro-acetylamino)-cyclopropanecarbonyl]-amino}-indan-5-yl)-benzoic acid methyl ester;
1-(2,2,2-Trifluoro-acetylamino)-cyclopropanecarboxylic acid{(rac)-5-[3,5-dichloro-2-(2,2-difluoro-ethoxy)-phenyl]-indan-1-yl}-amide;
(rac)-2-Chloro-6-(1-{[1-(2,2,2-trifluoro-acetylamino)-cyclopropanecarbonyl]-amino}-indan-5-yl)-benzoic acid methyl ester;
1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-indan-1-yl}-amide;

1-(2,2,2-Trifluoro-acetylamino)-cyclopropanecarboxylic acid{(S)-5-[5-chloro-3-fluoro-2-(5-methyl-[1,2,4]oxadiazol-3-yl)-phenyl]-indan-1-yl}-amide;
2-Chloro-6-((S)-1-{[3-(2,2,2-trifluoro-acetylamino)-oxetane-3-carbonyl]-amino}-indan-5-yl)-benzoic acid methyl ester;
3-(2,2,2-Trifluoro-acetylamino)-oxetane-3-carboxylic acid {(S)-5-[5-chloro-3-fluoro-2-(5-methyl-[1,2,4]oxadiazol-3-yl)-phenyl]-indan-1-yl}-amide;
3-(2,2,2-Trifluoro-acetylamino)-oxetane-3-carboxylic acid {(S)-5-[5-chloro-3-fluoro-2-(2-methyl-2H-tetrazol-5-yl)-phenyl]-indan-1-yl}-amide;
1-(2,2,2-Trifluoro-acetylamino)-cyclopropanecarboxylic acid{(rac)-6-[3,5-dichloro-2-(2,2-difluoro-ethoxy)-phenyl]-1,2,3,4-tetrahydro-naphthalen-1-yl}-amide;
(rac)-2-Chloro-6-(5-{[1-(2,2,2-trifluoro-acetylamino)-cyclopropanecarbonyl]-amino}-5,6,7,8-tetrahydro-naphthalen-2-yl)-benzoic acid methyl ester;
1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-1,2,3,4-tetrahydro-naphthalen-1-yl}-amide;
1-(2,2,2-Trifluoro-acetylamino)-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide;
1-(2,2,2-Trifluoro-acetylamino)-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide;
1-(2,2,2-Trifluoro-acetylamino)-cyclopropanecarboxylic acid{(rac)-7-[5-chloro-3-fluoro-2-(5-methyl-[1,2,4]oxadiazol-3-yl)-phenyl]-chroman-4-yl}-amide;
1-(2,2,2-Trifluoro-acetylamino)-cyclopropanecarboxylic acid{(rac)-7-[5-chloro-3-fluoro-2-(2-methyl-2H-tetrazol-5-yl)-phenyl]-chroman-4-yl}-amide;
1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide;
1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-1-methyl-indan-1-yl}-amide;
1-(2,2,2-Trifluoro-acetylamino)-cyclopropanecarboxylic acid{5-[5-chloro-3-fluoro-2-(2-methyl-2H-tetrazol-5-yl)-phenyl]-1-methyl-indan-1-yl}-amide;
1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide;
1-(2,2,2-Trifluoro-acetylamino)-cyclopropanecarboxylic acid{(rac)-6-[5-chloro-3-fluoro-2-(2-methyl-2H-tetrazol-5-yl)-phenyl]-2,3-dihydro-benzofuran-3-yl}-amide;
1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-2,3-dihydro-benzo[b]thiophen-3-yl}-amide;
1-(2,2,2-Trifluoro-acetylamino)-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide;
(1-{(S)-5-[5-Chloro-3-fluoro-2-(5-methyl-[1,2,4]oxadiazol-3-yl)-phenyl]-indan-1-ylcarbamoyl}-cyclopropyl)-carbamic acid tert-butyl ester;
1-Amino-cyclopropanecarboxylic acid{(S)-5-[5-chloro-3-fluoro-2-(5-methyl-[1,2,4]oxadiazol-3-yl)-phenyl]-indan-1-yl}-amide;
Pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
2-Methoxy-pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
Pyridazine-4-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
Isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
5-Methyl-[1,3,4]oxadiazole-2-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
3-Methoxy-isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
and pharmaceutically acceptable salts thereof.

Also particular examples of compounds of formula (I) as described herein are selected from
(1-{(rac)-5-[5-Chloro-3-fluoro-2-(5-methyl-[1,2,4]oxadiazol-3-yl)-phenyl]-7-fluoro-indan-1-ylcarbamoyl}-cyclopropyl)-carbamic acid tert-butyl ester;
1-Amino-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide;
2-Methoxy-pyrimidine-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;
Pyridazine-4-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;
3-Methoxy-isoxazole-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;
(1-{(rac)-3-[5-Chloro-3-fluoro-2-(5-methyl-[1,2,4]oxadiazol-3-yl)-phenyl]-6,7-dihydro-5H-[1]pyrindin-7-ylcarbamoyl}-cyclopropyl)-carbamic acid tert-butyl ester;
1-Amino-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide;
3-Methoxy-isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
Pyridazine-4-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
Pyridazine-4-carboxylic acid(1-{(R or S)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
Pyridazine-4-carboxylic acid(1-{(S or R)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
2-Methoxy-pyrimidine-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
Isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
(1-{(rac)-6-[5-Chloro-3-fluoro-2-(5-methyl-[1,2,4]oxadiazol-3-yl)-phenyl]-2,3-dihydro-benzofuran-3-ylcarbamoyl}-cyclopropyl)-carbamic acid tert-butyl ester;

1-Amino-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide;

Pyridazine-4-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

2-Methoxy-pyrimidine-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

3-Methoxy-isoxazole-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

3-Amino-oxetane-3-carboxylic acid{(S)-5-[5-chloro-3-fluoro-2-(5-methyl-[1,2,4]oxadiazol-3-yl)-phenyl]-indan-1-yl}-amide;

Pyrimidine-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

Isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

3-Methyl-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

3-Methoxy-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

(1-{(rac)-3-[5-Chloro-3-fluoro-2-(2-methyl-2H-tetrazol-5-yl)-phenyl]-6,7-dihydro-5H-[1]pyrindin-7-ylcarbamoyl}-cyclopropyl)-carbamic acid tert-butyl ester;

1-Amino-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide;

2-Methoxy-pyrimidine-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

Isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

3-Methyl-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

3-Methoxy-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

(1-{(rac)-6-[5-Chloro-3-fluoro-2-(2-methyl-2H-tetrazol-5-yl)-phenyl]-2,3-dihydro-benzo[b]thiophen-3-ylcarbamoyl}-cyclopropyl)-carbamic acid tert-butyl ester;

1-Amino-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide;

5-Methyl-[1,3,4]oxadiazole-2-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

Pyrimidine-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

Isoxazole-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

3-Methoxy-isoxazole-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

and pharmaceutically acceptable salts thereof.

Further particular examples of compounds of formula (I) as described herein are selected from 1-(2,2,2-Trifluoro-acetylamino)-cyclopropanecarboxylic acid{(S)-5-[5-chloro-3-fluoro-2-(5-methyl-[1,2,4]oxadiazol-3-yl)-phenyl]-indan-1-yl}-amide;

1-(2,2,2-Trifluoro-acetylamino)-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide;

1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide;

2-Methoxy-pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;

Pyridazine-4-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;

3-Methoxy-isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;

and pharmaceutically acceptable salts thereof.

Also further particular examples of compounds of formula (I) as described herein are selected from 2-Methoxy-pyrimidine-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;

3-Methoxy-isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

2-Methoxy-pyrimidine-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

2-Methoxy-pyrimidine-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

3-Methoxy-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

2-Methoxy-pyrimidine-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

3-Methoxy-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

Pyrimidine-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
AcOH=acetic acid, BOC=t-butyloxycarbonyl, BuLi=butyllithium, CDI=1,1-carbonyldiimidazole, $CH_2Cl_2$=dichloromethane, DBU=2,3,4,6,7,8,9,10-octahydro-pyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3$ N=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=$iPr_2NEt$=N-ethyl diisopropylamine, IPC=in process control, LAH=lithium aluminium hydride, LDA=lithium diisopropylamide, $LiBH_4$=lithium borohydride, MeOH=methanol, $NaBH_3CN$, sodium cyanoborohydride, $NaBH_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Amines 1 (Scheme 1a) can be coupled with acids 2 to give amides 3 by using well known coupling methods like e.g. with EDCI (N-(3-dimethylaminopropyl)-N'-ethylcarbodiimide hydrochloride), optionally in the presence of HOBT (1-hydroxybenzo-triazole) and a base like Huenig's base (N-ethyl diisopropylamine) in solvents like N,N-dimethylformamide preferably between 0° C. and room temperature or by use of HATU (O-(7-azabenzotriazol-1-yl)-1,1,3,3-tetramethyluronium hexafluorophosphate), triethylamine, in N,N-dimethylformamide preferably between 0° C. and room temperature (step a). Reaction of amides 3 with e.g. 4,4,4',4',5,5,5',5'-octamethyl-2,2'-bi(1,3,2-dioxaborolane) in solvents like dimethylsulfoxide or dioxane in the presence of potassium acetate and catalysts like (1,1'-bis-diphenylphosphino)-ferrocene)palladium-(II)dichloride (1:1 complex with dichloromethane) at temperatures up to about 100° C. gives aryl-boronic ester compounds 4 (step b). Condensation of aryl halides 3 with suitable aryl boronic acid or aryl boronic ester derivatives or condensation of boronic ester derivatives 4 with suitable aryl halides leading to adducts 5 or to compounds of the general formula 7 can be performed under Suzuki conditions, e.g. in the presence of catalysts, such as tri-o-tolylphosphine/palladium(II)acetate, tetrakis-(triphenylphosphine)-palladium or dichloro[1,1'-bis(diphenylphosphino)-ferrocene]palladium(II) optionally in the form of a dichloromethane complex (1:1), and in the presence of a base, such as aqueous or non aqueous potassium phosphate, sodium or potassium carbonate, in a solvent, such as dimethylsulfoxide, toluene, dioxane, tetrahydrofuran or N,N-dimethylformamide, and in an inert atmosphere such as argon or nitrogen, in a temperature range preferably between room temperature and about 130° C. (steps c, d). Removal of the protective groups present in compounds 5 can be performed under standard conditions well known for the respective protective function, thus liberating free amine compounds (step e). Coupling of amine compounds 6 with suitable derivatives under conditions as e.g. described in step a or know to the man skilled in the art gives compounds of the general formula (I) (step f).

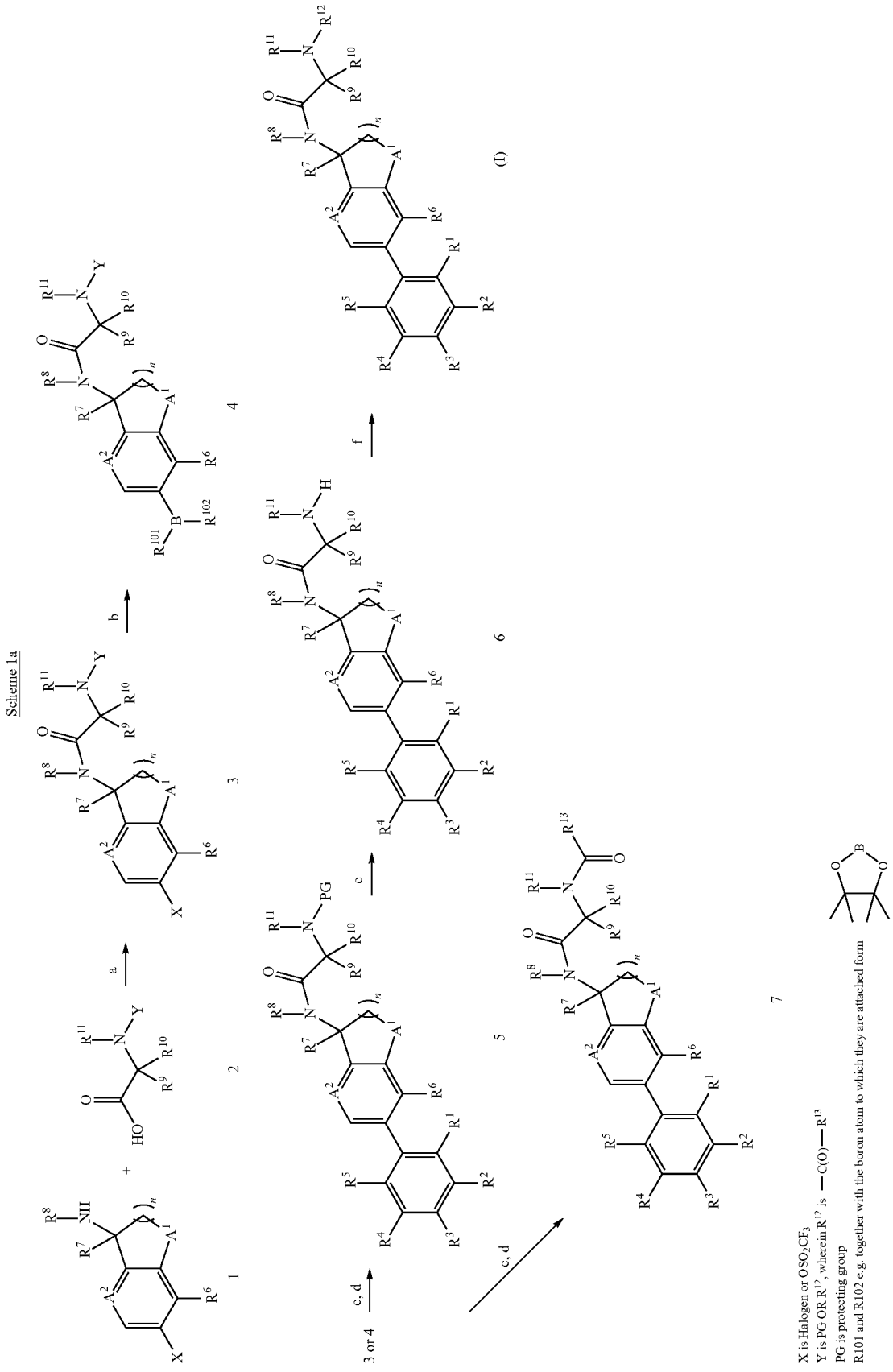

-continued
Scheme 1a
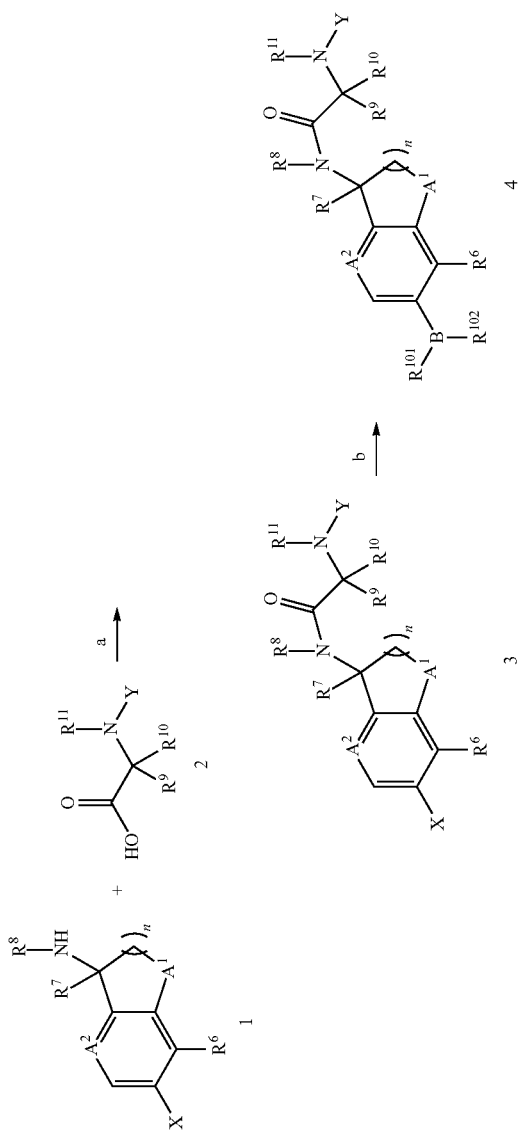

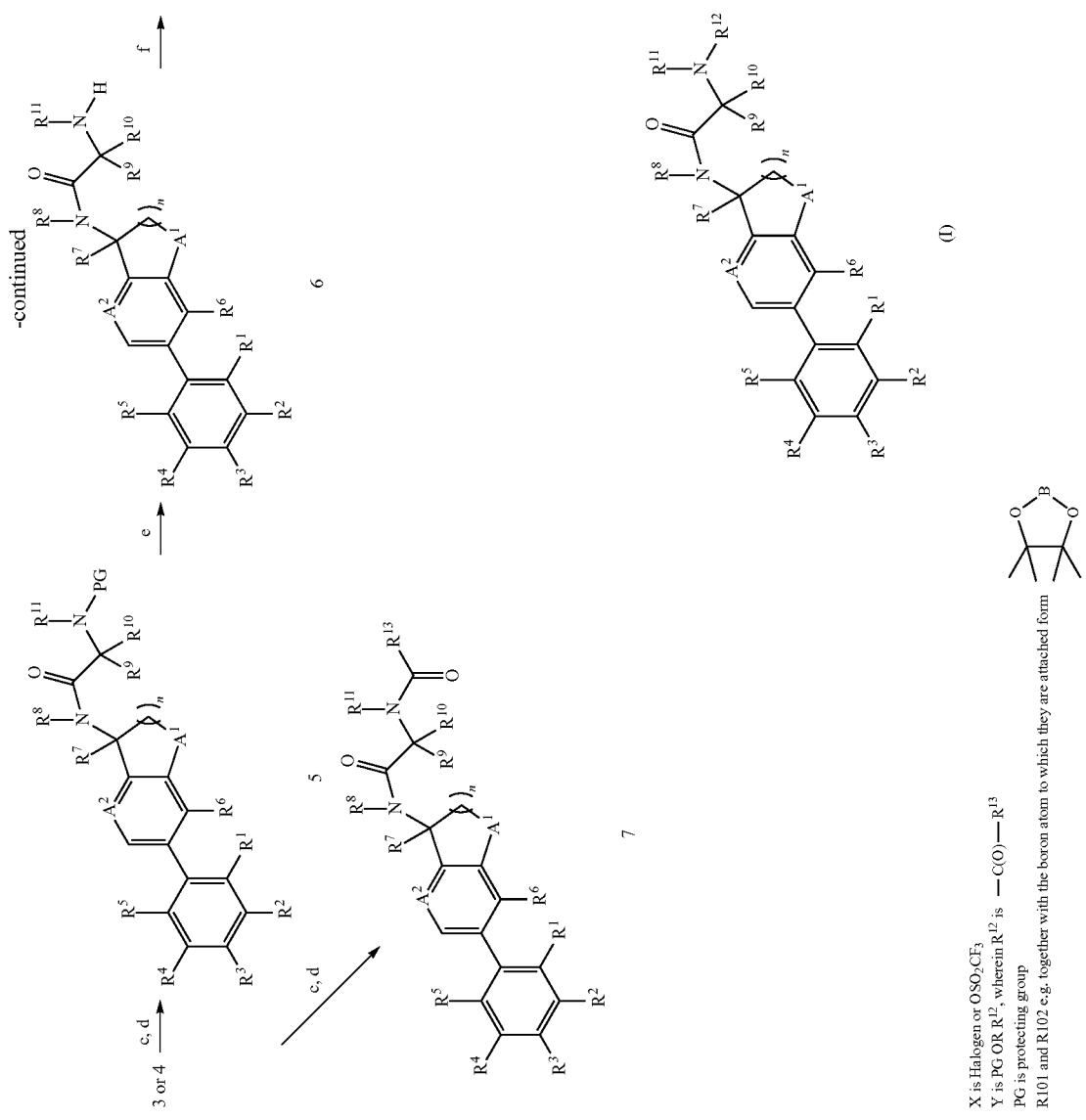
X is Halogen or OSO$_2$CF$_3$
Y is PG OR R$^{12}$, wherein R$^{12}$ is —C(O)—R$^{13}$
PG is protecting group
R101 and R102 e.g. together with the boron atom to which they are attached form Alternatively (Scheme 1b), a protective group can be attached to amines of formula I giving protected amines 8 (step g). Performing similar transformations as described above (steps b, c, d) gives amino protected biaryl compounds 10. Removal of the protective group liberates free amines 11 (step h), coupling under conditions as described above (step a) gives amides 12 carrying again a protective group. Removal of the protective group in compounds 12 leads then to compounds 6 (step k).

Scheme 1b

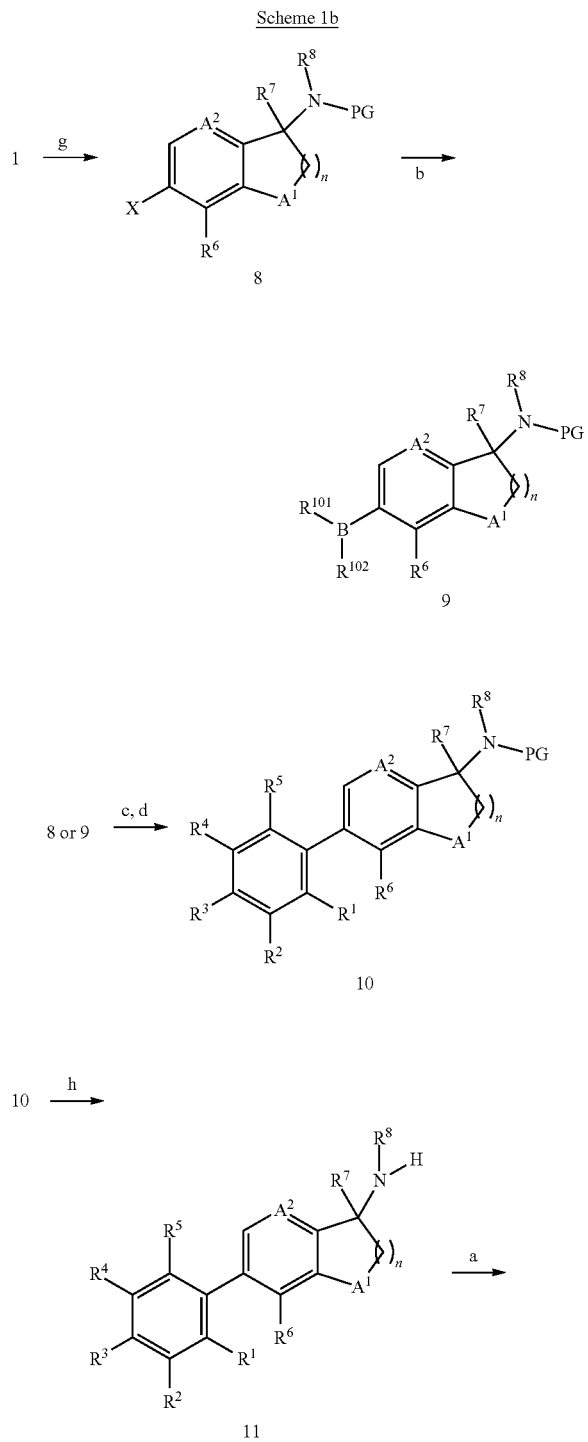

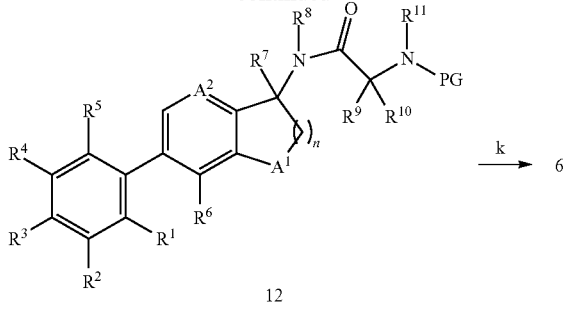

X is Halogen or OSO$_2$CF$_3$
PG is protecting group
R101 and R102 e.g.
together with the boron atom to which they are attached form 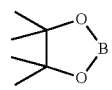

Amine derivatives 1, 102, 107, 108, 115 and 121 (Scheme 2a and 2b) are known or can be prepared by procedures known in the art. Reductive amination of ketone derivatives 101 e.g. by treatment with sodium cyanoborohydride, ammonium acetate in a solvent like isopropanol preferably at reflux gives racemic amino derivatives 102 (step a). Optically pure or optically enriched amine compounds 107 and 108 can be prepared by different methods such as i) by separation of racemic amino compounds 102 into its antipodes by methods known in the art, such as separation of the antipodes via diastereomeric salts by crystallization with optically pure acids or by separation of the antipodes by specific chromatographic methods using either a chiral adsorbens or a chiral eluent; or ii) by enantioselective syntheses starting e.g. from ketone derivatives 101: enantioselective reduction of ketone derivatives 101 can e.g. be performed with borane dimethylsulfide complex and (S or R) 1-methyl-3,3-diphenyl-tetrahydro-pyrrolo[1,2-c][1,3,2]oxazaborole as catalyst in solvents like toluene, dichloromethane or tetrahydrofuran at temperatures between −78° C. and RT leading to optically pure or optically enriched secondary alcohol derivatives 103 or 104 (step b). Secondary alcohol derivatives 103 or 104 can then be converted into the corresponding azido derivatives with inverted absolute configuration e.g. by reaction with diphenylphosphorylazide (DPPA) and 1,8-diazabicyclo-[5.4.0]undecene-7 (DBU) in a solvent like toluene at temperatures preferable between 0° C. and RT (step c). Azido derivatives 105 or 106 can then be reduced to the corresponding amino derivatives 107 or 108 e.g. by treatment with tin dichloride in methanol around RT or with triphenylphosphine, optionally with a base like potassium hydroxide preferably in solvent mixtures like tetrahyrofuran/water around room temperature giving optically pure or optically enriched amino compounds 107 or 108 (step d).

Addition of 1,3-dithiane lithium (prepared from 1,3-dithiane and n-butyllithium at temperatures around −30° C.) to ketones 101 in solvents like tetrahydrofuran at temperatures between −30° C. and RT gives hydroxy compounds 109 (step e). Water elimination, e.g. using p-toluenesulfonic acid in benezene or toluene with removal of water by a Dean-Stark trap gives olefins 110 (step f). Olefins 110 can be transformed into acids 111 e.g. by heating in a mixture of acetic and hydrochloric acid preferably at reflux (step g). Esters 112, obtained by standard esterification (step h), can be lithiated at the alpha position with lithium bis(trimethylsilyl)acetamide in solvents like tetrahydrofuran at −78° C. followed by reaction with an alkyl halide between −78° C. and RT leading to substituted ester compounds 113 (step i). Ester hydrolysis, e.g. by using sodium trimethylsilanoate in tetrahydrofuran at reflux gives acids 114 (step k). Treatment of acids 114 e.g. with diphenylphosphorylazide (DPPA) in toluene, triethylamine at reflux and quenching the isocyanate with sodium trimethylsilanoate in tetrahydrofuran around RT gives amines 115 with an alkyl substituent $R^7$ (step 1). Amines 115 can optionally be separated into its antipodes via diastereomeric salts formation or by separation of the antipodes by specific chromatographic methods using either a chiral adsorbens or a chiral eluent. Optionally amines 115 can be alkylated at the amine nitrogen atom e.g. by introduction of a Boc group, performing the alkylation by reaction with a base like sodium hydride following by addition of an alkylating agent like an alkyl or cycloalkyl halide, alkyl or cycloalkyl tosylate or an alkyl or cycloalkyl mesylate followed by removal of the Boc group to gives amine 1 carrying alkyl or cycloalkyl subsituents $R^8$ (step m).

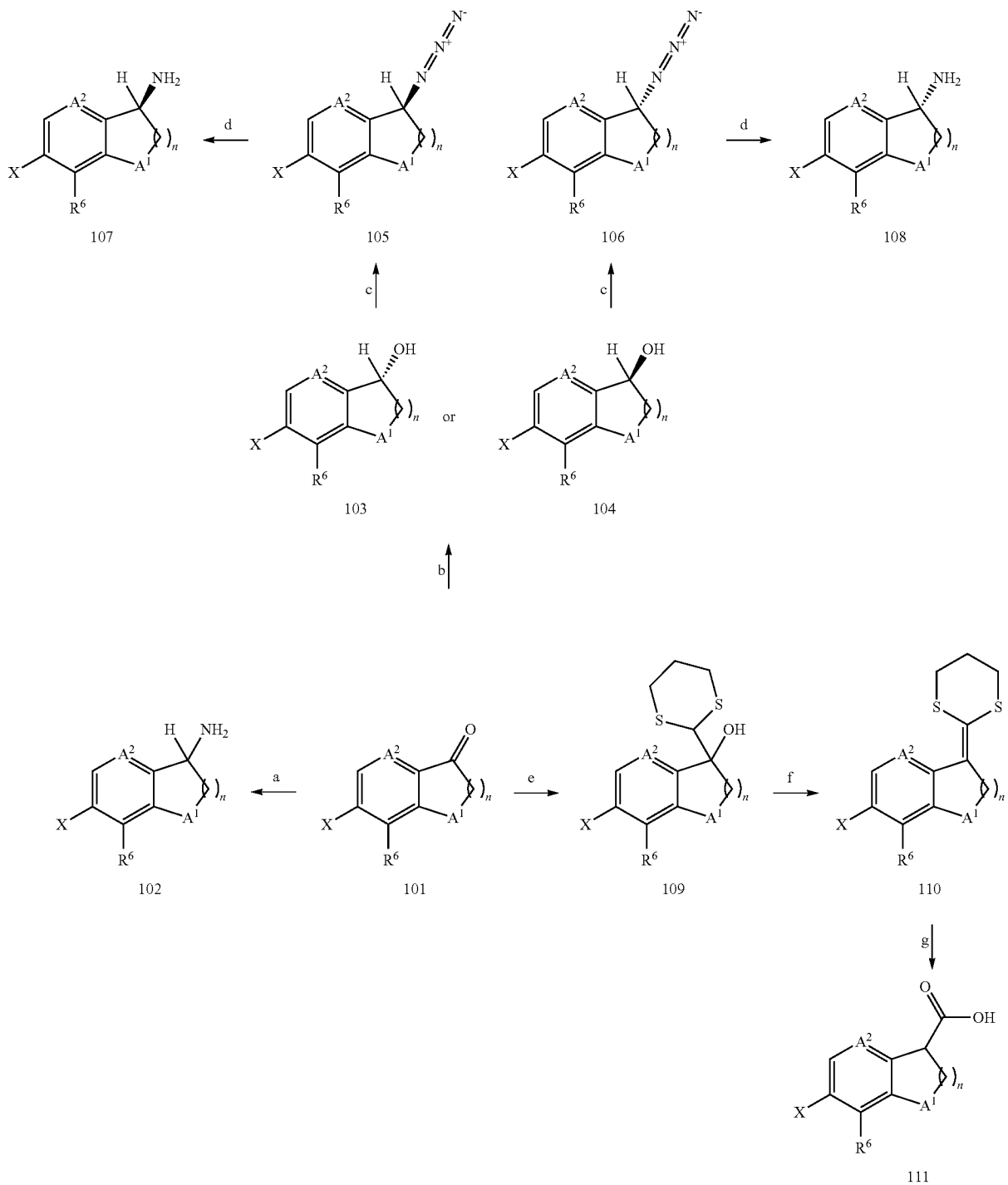

Scheme 2a

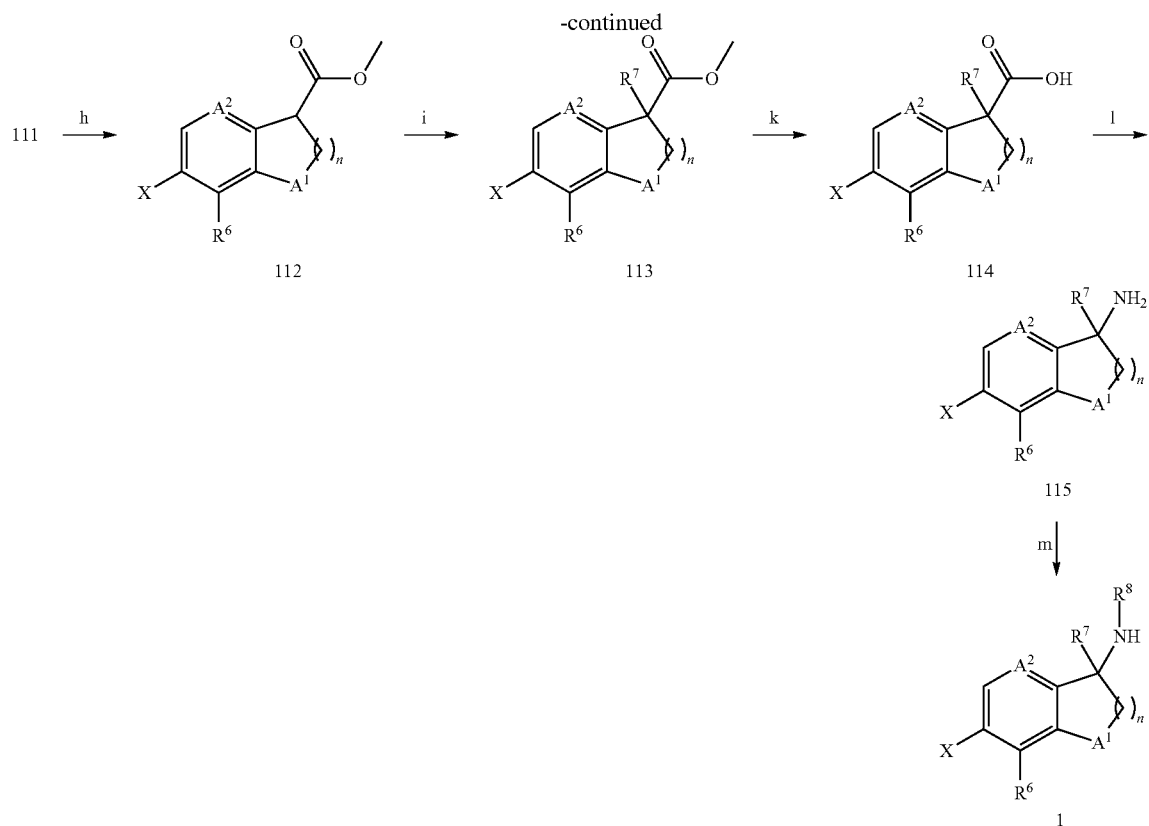

X is Halogen or OSO₂CF₃

Treatment of 1H-indole-2,3-diones 116 (Scheme 2b) with 4-methoxy-aniline in a solvent like methanol gives Schiff-bases 117 (step n), which can be reduced to methoxy-anilino substituted 2,3-dihydro-1H-indoles 118 e.g. with sodium borohydride in a solvent like methanol at elevated temperature (step o). Removal of the methoxy-phenyl moiety with ceric ammonium nitrate e.g. in a solvent mixture of acetonitrile and water gives amino substituted 2,3-dihydro-1H-indoles 119 (step p). Amino substituted 2,3-dihydro-1H-indoles 121 carrying two orthogonal protective groups can be prepared from amino substituted 2,3-dihydro-1H-indoles 119 by first introduction of a phthaloyl protective group at the primary amine moiety followed by introduction of protective group PG$^a$, removal of the phthaloyl moiety and introduction of protective group PG$^b$ (steps q, r). Compounds 121 can be used for further transformation into compounds of formula (I) using methods and procedures similar to those described for the further transformation of compounds 8 (Scheme 1b).

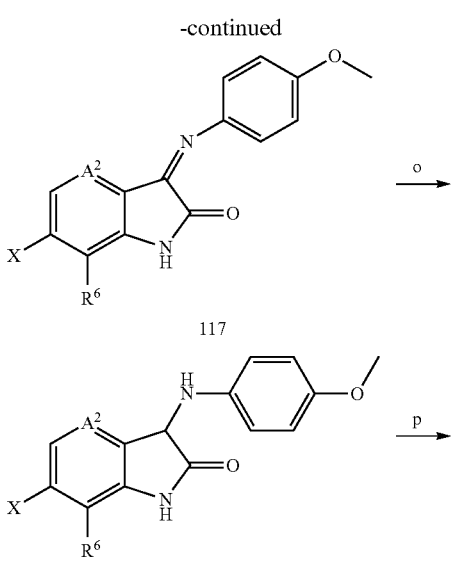

Scheme 2b

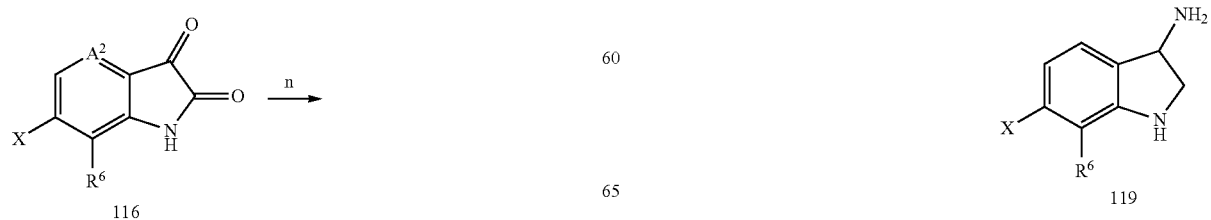

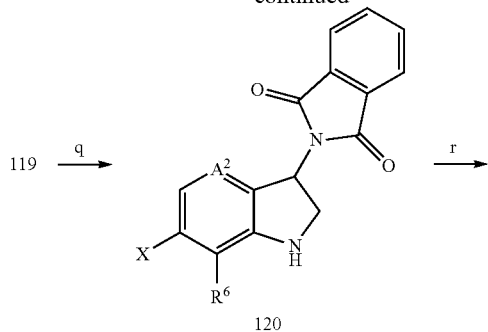

PG$^a$ and PG$^b$ are protecting group
X is Halogen or OSO$_2$CF$_3$

Ketone derivatives 204, 207, 209, 212, 216 and 220 are known or can be prepared by procedures known in the art. Thus, the acid derivatives 201 (Scheme 3) can be converted into the corresponding acid chloride derivatives 202 e.g. by reaction with thionyl chloride in a solvent like benzene or dichloromethane at temperatures preferably between 0° C. and the reflux temperatures of the respective solvent (step a). Treatment of acid chloride derivatives 202 with ethylene in the presence of a Lewis acid catalyst like aluminium trichloride in a solvent like dichloroethane preferably around room temperature gives chloroethyl ketones 203, which can be reacted further in the presence of aluminium chloride and optionally an additive like sodium chloride at elevated temperatures (up to about 200° C.) to give cyclic ketones 204 (steps b, c). Reaction of phenol derivatives 205 e.g. with chloroacetonitrile in the presence of aluminium chloride and boron trichloride in a solvent like dichloromethane preferably around RT gives chloromethyl ketone derivatives 206, which can be cyclized into cyclic ketones 207 in the presence of a base like triethylamine in solvents as e.g. acetonitrile (steps d, e). Reaction of phenol derivatives 205 e.g. with 3-bromopropionic acid in the presence of a base like sodium hydroxide e.g. in water gives 3-hydroxypropionic acid derivatives 208, 3-hydroxypropionic acid derivatives 208 and be cyclized into cylic ketones 209 in the presence of phosphorus pentachloride and aluminium trichloride at elevated temperature (steps f, g). Reaction of thiophenol derivatives 210 e.g. with 2-chloro-acetic acid in a solvent like water and in the presence of a base like sodium hydroxide at temperatures up to reflux gives thioacetic acid derivatives 211 (step h). Thioacetic acid derivatives 211 can then be converted into the corresponding acid chlorides e.g. by reaction with thionyl chloride at reflux and subsequently be cyclized with the help of aluminium trichloride in a solvent like 1,2-dichloro-benzene at temperatures up to about 100° C. (step i). Iodophenol derivatives 213 react with alkyl 3-mercaptopropionates in the presence of catalyst mixtures like 1,1'-bis(diphenylphosphino)-ferrocene and tris(dibenzylideneacetone)-dipalladium in solvents like N,N-dimethylformamide and in the presence of a base like triethylamine at temperatures up to about 100° C. to give ester compounds 214 (step k). Free acids 215 (obtained by ester hydrolysis under acidic or basic conditions) can be cyclized to ketones 216 e.g. in concentrated sulfuric acid at temperatures around RT (steps l, m). Annelated pyridine derivatives 217 can be oxidized to the corresponding N-oxide derivatives 218 e.g. by using meta-chloro perbenzoic acid in a solvent like dichloromethane preferably around RT or with aqueous hydrogen peroxide in acetic acid at temperatures up to reflux temperature (step n); subsequent rearrangement e.g. with trifluoroacetic anhydride in dichloromethane at a temperature around RT followed by mild saponification gives annelated hydroxy compounds 219 (step o). Annelated hydroxy compounds 219 can be used directly for the synthesis of amino compounds 1 as described in Scheme 2 or alternatively, oxidation of the annelated hydroxy compounds 219 e.g. by using manganese dioxide in a solvent like dichloromethane preferable at RT gives annelated ketone derivatives 220 (step p).

Scheme 3

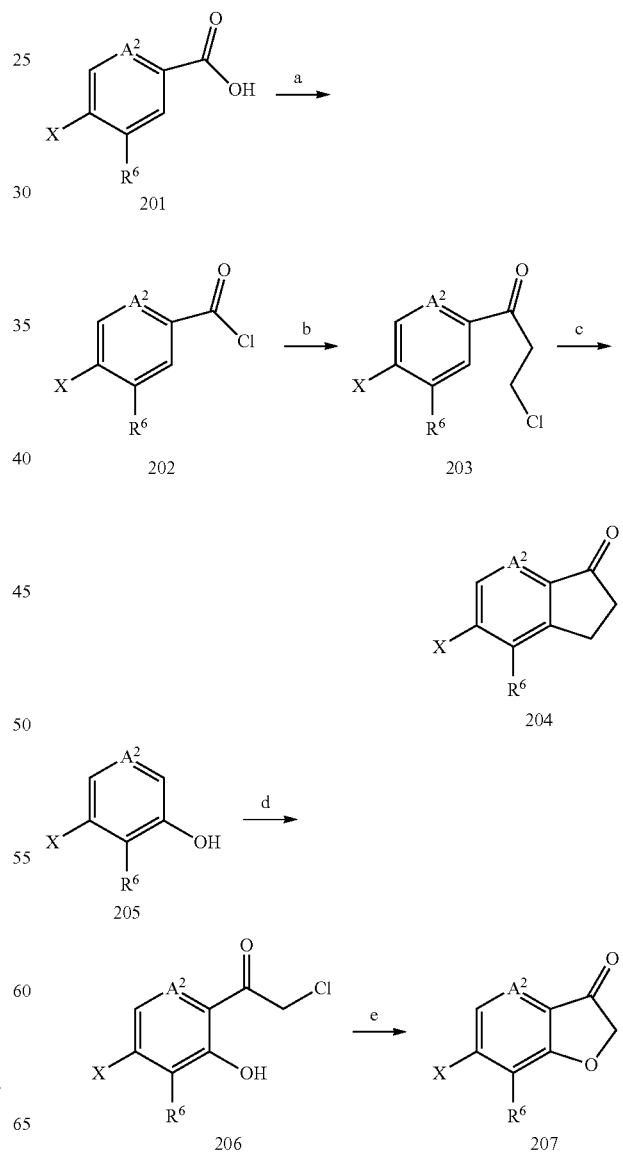

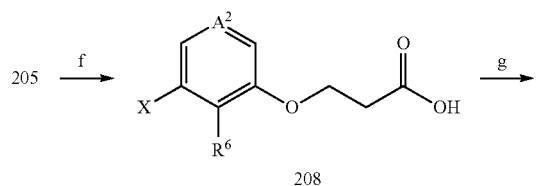

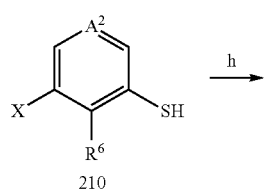

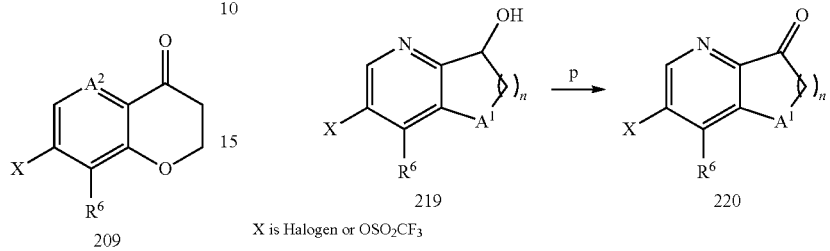

X is Halogen or OSO₂CF₃

Also an embodiment of the present invention is a process to prepare a compound of formula (I) as defined above comprising the reaction of a) a compound of formula (II) in the presence of a compound of formula (III);

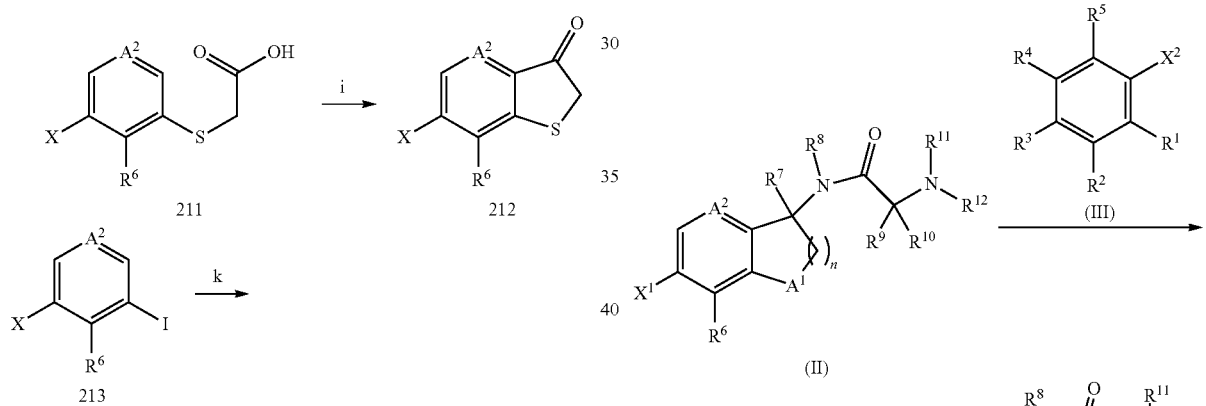

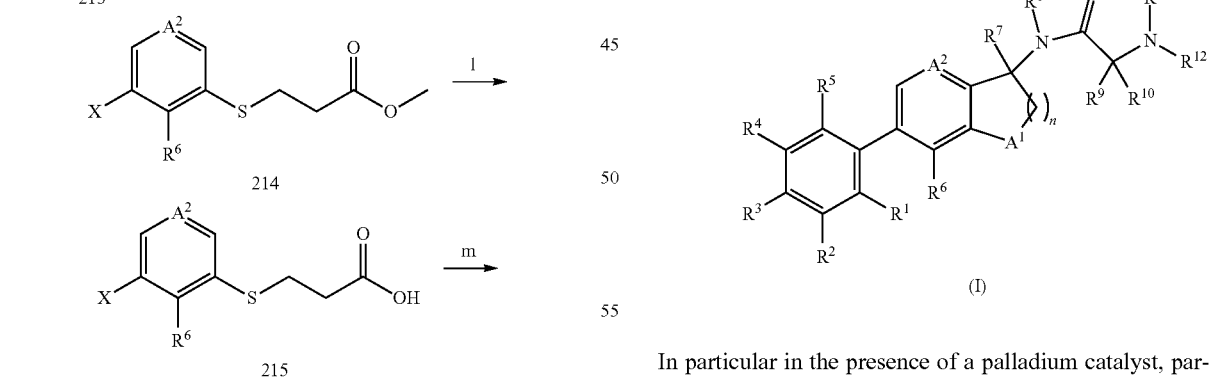

In particular in the presence of a palladium catalyst, particularly (1,1'-bis-diphenylphosphino)-ferrocene)palladium-(II)dichloride, in the presence or not of a boronic derivatives, particularly 4,4,4',4',5,5,5',5'-octamethyl-2,2'-bi(1,3,2-dioxaborolane), in the presence or not of a base, particularly in the presence of KOAc and K₂CO₃, in a solvent, particularly DMF and DMSO, at a temperature comprised between RT and reflux, wherein $A^1$, $A^2$, $R^1$, $R^2$, $R^3$, $R^4$, $R^5$, $R^6$, $R^7$, $R^8$, $R^9$, $R^{10}$, $R^{11}$, $R^{12}$ and n are as defined herein and wherein $X^1$ and $X^2$ are halogen, particularly chloro or bromo, boronic acid or boronic ester, particularly 4,4,5,5-tetramethyl-[1,3,2]dioxaborolanyl, wherein in case one of $X^1$ or $X^2$ is boronic acid or boronic ester then the other one is halogen; or b) a compound of formula (IV) in the presence of a compound of formula (V);

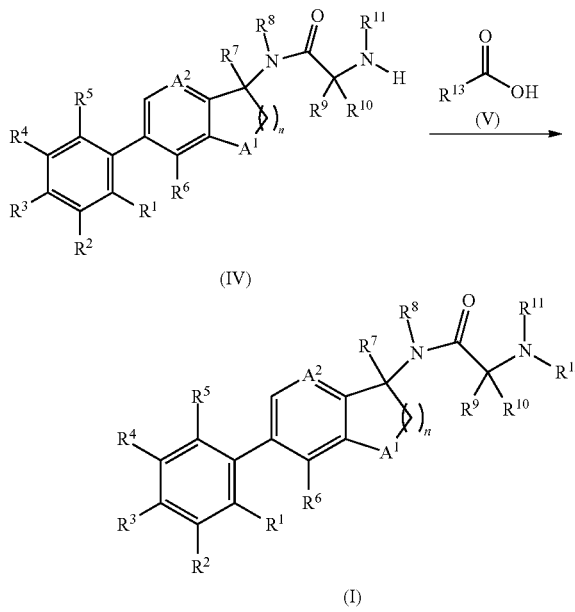

In particular in the presence of a coupling agent, particularly EDCI, HOBT or HATU, in the presence or not of a base, particularly in the presence of Hünig's base and triethylamine, in a solvent, particularly DMF, at a temperature comprised between 0° C. and reflux, wherein $A^1$, $A^2$, $R^1$, $R^2$, $R^3$, $R^4$, $R^5$, $R^6$, $R^7$, $R^8$, $R^9$, $R^{10}$, $R^{11}$, n are as defined herein and wherein $R^{12}$ is —C(O)—$R^{13}$, wherein $R^{13}$ is as defined herein.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

Also an object of the present invention is the use of a compound according to formula (I) as described herein for the treatment or prophylaxis of illnesses which are caused by disorders mediated through the stimulation of bradykinin receptor pathway.

The present invention also relates to the use of a compound according to formula (I) as described herein for the treatment or prophylaxis of glomerulonephritides, Henoch-Schönlein purpura nephropathy, ANCA-associated crescentic glomerulonephritis, lupus nephritis and IgA nephritis.

Also an embodiment of the present invention is the use of a compound according to formula (I) as described herein for the treatment or prophylaxis of glomerulonephritides.

A particular embodiment of the present invention is a compound according to formula (I) as described herein for the treatment or prophylaxis of glomerulonephritides, Henoch-Schönlein purpura nephropathy, ANCA-associated crescentic glomerulonephritis, lupus nephritis and IgA nephritis.

Also a particular embodiment of the present invention is a compound according to formula (I) as described herein for the treatment or prophylaxis of glomerulonephritides.

Also an object of the invention is a method for the treatment or prophylaxis of glomerulonephritides, Henoch-Schönlein purpura nephropathy, ANCA-associated crescentic glomerulonephritis, lupus nephritis and IgA nephritis, which method comprises administering an effective amount of a compound according to formula (I) as described herein.

Also an embodiment of the present invention is a method for the treatment or prophylaxis of glomerulonephritides, which method comprises administering an effective amount of a compound according to formula (I) as described herein.

The present invention also relates to the use of a compound according to formula (I) as described herein for the preparation of a medicament for the treatment or prophylaxis of glomerulonephritides, Henoch-Schönlein purpura nephropathy, ANCA-associated crescentic glomerulonephritis, lupus nephritis and IgA nephritis.

Also an embodiment of the present invention is the use of a compound according to formula (I) as described herein for the preparation of a medicament for the treatment or prophylaxis of glomerulonephritides.

A further object of the present invention comprises a compound according to formula (I) as described herein, when manufactured according to any one of the described processes.

Assay Procedures

Receptor Binding Assay

Binding assays were done with membranes from CHO-K1 cells overexpressing Bradykinin-1 receptor.

For binding, Bradykinin-1 receptor antagonist compounds were added in various concentrations in 50 mM Tris pH 7.4, 5 mM $MgCl_2$ together with 6 nM Kallidin (Des $Arg^{10}$, $Leu^9$), [3,4-Prolyl-3,4-$^3$H(N)](PerkinElmer, 1.85-4.44 TBq/mmol) to 40 µg membrane protein containing approximately 1 fmol Bradykinin-1 receptor and incubated for 15 min at 27° C. To determine non-specific binding 10 µM Lys-(Des-$Arg^9$)-Bradykinin (Bachem) was added. Membranes were harvested through GF/B (glass fiber filter; PerkinElmer) plates, equilibrated with 0.5% polyethylenimine, air dried at 50° C. for 2 h. Radioactivity was determined by counting in a top-counter (NXT Packard). Specific binding was defined as total binding minus nonspecific binding and typically represents about 90-95% of the total binding. Antagonist activity is expressed as Ki: inhibitor concentration required for 50% inhibition of specific binding corrected for the concentration of the radioligand.

Calcium Mobilization Assay

GeneBLAzer® Bradykinin (B1)-NFAT-bla CHO-K1 cells (from Invitrogen) stably overexpressing the human bradykinin 1 receptor were cultured in DMEM (high glucose) supplemented with 10% dialysed FBS, 1% NEAA (non essential amino acids) 1% penicillin/streptomycin, 1% G418 and 0.1 mg/ml zeocin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

| Example | B1R Binding Assay Ki [μM] | Ca mobilization Assay IC50 [μM] |
|---|---|---|
| 1 | 2.17 | 2.25 |
| 2 | 0.146 | 0.0768 |
| 3 | 0.123 | 0.0474 |
| 4 | 0.0202 | 0.002 |
| 5 | 0.0062 | 0.0006 |
| 6 | 0.381 | 0.455 |
| 7 | 0.0374 | 0.0286 |
| 8 | 0.0303 | 0.0244 |
| 9 | 0.236 | 0.0826 |
| 10 | 0.522 | 0.118 |
| 11 | 0.0416 | 0.004 |
| 12 | 0.0044 | 0.0005 |
| 13 | 0.0095 | 0.0005 |
| 14 | 0.212 | 0.0248 |
| 15 | 0.170 | 0.0246 |
| 16 | 0.0110 | 0.0005 |
| 17 | 0.0059 | 0.0006 |
| 18 | 0.0067 | 0.0005 |
| 19 | 0.0333 | 0.0045 |
| 20 | 0.0240 | 0.0036 |
| 21 | 0.0095 | 0.0023 |
| 22 | 0.0066 | 0.0008 |
| 23 | 0.669 | 0.332 |
| 24 | 0.0364 | 0.005 |
| 25 | 0.0031 | 0.0001 |
| 26 | 0.0026 | 0.0002 |
| 27 | 0.0036 | 0.0004 |
| 28 | 0.0041 | 0.0003 |
| 29 | 0.0095 | 0.0034 |
| 30 | 0.0039 | 0.0001 |
| 31 | 0.4754 | 0.1353 |
| 32 | 0.4580 | 0.0956 |
| 33 | 0.0189 | 0.0005 |
| 34 | 0.0151 | 0.0006 |
| 35 | 0.0171 | 0.0005 |
| 36 | 0.3606 | 0.0036 |
| 37 | 0.5908 | 0.3006 |
| 38 | 0.0030 | 0.0002 |
| 39 | 0.0075 | 0.0006 |
| 40 | 0.1298 | 0.0352 |
| 41 | 0.0040 | 0.0002 |
| 42 | 0.0040 | 0.0002 |
| 43 | 0.0063 | 0.0003 |
| 45 | 1.5296 | 0.7006 |
| 46 | 0.0191 | 0.0047 |
| 47 | 0.0054 | 0.0002 |
| 48 | 0.0238 | 0.0040 |
| 50 | 0.0048 | 0.0004 |
| 51 | 0.0118 | 0.0027 |
| 52 | 0.0257 | 0.0043 |
| 53 | 0.0036 | 0.0004 |
| 54 | 0.0632 | 0.0058 |
| 55 | 0.2108 | 0.0611 |
| 56 | 0.0045 | 0.0002 |
| 57 | 0.0058 | 0.0004 |
| 58 | 0.0063 | 0.0004 |
| 59 | 0.0035 | 0.0003 |
| 61 | 0.2644 | 0.0174 |
| 62 | 0.0122 | 0.0048 |
| 63 | 0.0048 | 0.0002 |
| 64 | 0.0071 | 0.0005 |
| 65 | 0.0044 | 0.0002 |

Compounds of formula (I) and their pharmaceutically acceptable salts or esters thereof as described herein have $IC_{50}$ values between 0.000001 uM and 1000 uM, particular compounds have $IC_{50}$ values between 0.000005 uM and 500 uM, further particular compounds have $IC_{50}$ values between 0.00005 uM and 5 uM. Compounds of formula (I) and their pharmaceutically acceptable salts or esters thereof as described herein have Ki values between 0.0000001 uM and 1000 uM, particular compounds have Ki values between 0.0000005 uM and 500 uM, further particular compounds have Ki values between 0.000005 uM and 50 uM. These results have been obtained by using the foregoing binding and/or calcium mobilization assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of pain including, for example, visceral pain (such as pancreatitis, interstitial cystitis, renal colic, prostatitis, chronic pelvic pain), neuropathic pain (such as post-herpetic neuralgia, acute zoster pain, nerve injury, the "dynias", e.g., vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (e.g., post-mastectomy syndrome, post-thoracotomy syndrome, stump pain), bone and joint pain (osteoarthritis), spine pain (e.g., acute and chronic low back pain, neck pain, spinal stenosis), shoulder pain, repetitive motion pain, dental pain, sore throat, cancer pain, myofascial pain (muscular injury, fibromyalgia), post-operative, perioperative pain and preemptive analgesia (including but not limited to general surgery, orthopedic, and gynecological), chronic pain, dysmenorrhea (primary and secondary), as well as pain associated with angina, and inflammatory pain of varied origins (e.g. osteoarthritis, rheumatoid arthritis, rheumatic disease, teno-synovitis and gout, ankylosing spondylitis, bursitis).

Furthermore, the compounds of formula (I) or their pharmaceutically acceptable salts and esters as described herein can also be used to treat hyperreactive airways and to treat inflammatory events associated with airways disease (e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome").

The compounds of formula (I) or their pharmaceutically acceptable salts and esters as described herein may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssnoss.

In another embodiment, the compounds of formula (I) or their pharmaceutically acceptable salts and esters as described herein may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema, brain inflammation, stroke and angioedema.

The compounds of formula (I) or their pharmaceutically acceptable salts and esters as described herein may also be used for the treatment of glomerulonephritides and other inflammatory kidney diseases, including Henoch-Schönlein purpura nephropathy (HSPN) and ANCA-associated crescentic glomerulonephritis. They may be used to treat obesity, diabetes, diabetic vasculopathy, diabetic neuropathy, diabetic retinopathy, post-capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, e.g., Parkinson's and Alzheimers disease, epilepsy, septic shock, e.g. as anti-hypovolemic and/or anti-hypotensive agents, headache including cluster headache, migraine including prophylactic and acute use, stroke, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples were prepared under argon atmosphere.

Intermediate A-1

1-(2,2,2-Trifluoro-acetylamino)-cyclopropanecarboxylic acid[(rac)-5-(4,4,5,5-tetramethyl-[1,3,2]dioxaborolan-2-yl)-indan-1-yl]-amide

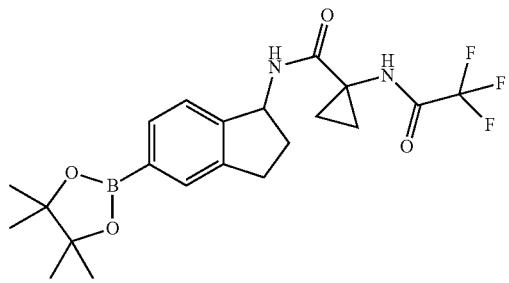 [SMILES: CC1(C)OB(c2ccc3c(c2)CCC3NC(=O)C2(NC(=O)C(F)(F)F)CC2)OC1(C)C]

[A] 1-(2,2,2-Trifluoro-acetylamino)-cyclopropanecarboxylic acid

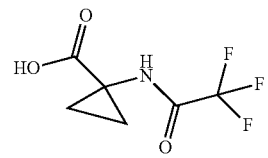 [SMILES: O=C(NC1(C(=O)O)CC1)C(F)(F)F]

Amino-cyclopropanecarboxylic acid (2.483 g, 23.8 mmol) was added to MeOH (60 ml) to give a white suspension. Et₃N (2.65 g, 3.65 ml, 26.2 mmol) and trifluoro-acetic acid ethyl ester (3.72 g, 3.12 ml, 26.2 mmol) were added and the mixture was stirred at RT. After 24 h, it was poured onto ice, acidified with 1N HCl and extracted four times with EtOAc. The organic layer was washed once with water and once with 1N HCl, dried over MgSO₄, filtered and evaporated; the residue formed was dried in vacuo to give the title compound (4.07 g, 87%) as colorless solid. MS: 196.0 (M−H⁻).

[B] 1-(2,2,2-Trifluoro-acetylamino)-cyclopropanecarboxylic acid ((rac)-5-bromo-indan-1-yl)-amide

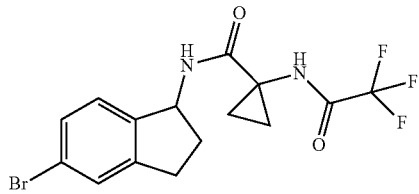 [SMILES: O=C(NC1(C(=O)NC2CCc3cc(Br)ccc32)CC1)C(F)(F)F]

1-(2,2,2-Trifluoroacetamido)cyclopropanecarboxylic acid (390 mg, 1.98 mmol) and HATU (753 mg, 1.98 mmol) were dissolved in DMF (12 ml), then Et$_3$N (601 mg, 828 µl, 5.94 mmol) was added and the reaction mixture was stirred for 30 minutes. Subsequently, (rac)-5-bromo-indan-1-ylamine (0.42 g, 1.98 mmol), dissolved in DMF (3 ml), was added and the mixture stirred at RT for 15 h. It was then poured into H$_2$O (50 ml) and extracted with CH$_2$Cl$_2$ (2×25 ml). The organic layers were dried over MgSO$_4$, filtered and concentrated in vacuo to give a crude product (0.876 g) which was purified by flash chromatography (silica gel, 20 g, 0% to 5% MeOH in CH$_2$Cl$_2$) to give the title compound (0.64 g, 83%) as light brown oil. MS: 389.0 (M−H$^-$, 1Br).

[C] 1-(2,2,2-Trifluoro-acetylamino)-cyclopropanecarboxylic acid[(rac)-5-(4,4,5,5-tetramethyl-[1,3,2]dioxaborolan-2-yl)-indan-1-yl]-amide

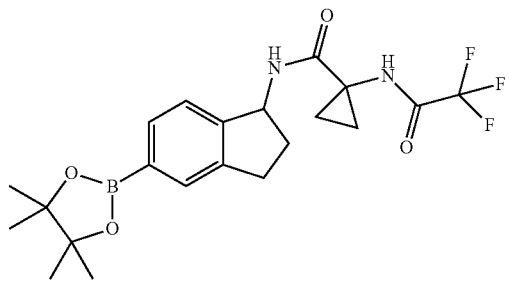 [SMILES: CC1(C)OB(c2ccc3c(c2)CCC3NC(=O)C2(NC(=O)C(F)(F)F)CC2)OC1(C)C]

1-(2,2,2-Trifluoro-acetylamino)-cyclopropanecarboxylic acid ((rac)-5-bromo-indan-1-yl)-amide (1.32 g, 3.37 mmol), 4,4,4',4',5,5,5',5'-octamethyl-2,2'-bi(1,3,2-dioxaborolane), (1.71 g, 6.75 mmol), potassium acetate (994 mg, 10.1 mmol) and (1,1'-bis-diphenylphosphino)-ferrocene)palladium-(II) dichloride (1:1 complex with CH$_2$Cl$_2$) (123 mg, 169 µmol, eq: 0.05) were dissolved in dioxane (33.7 ml) and reaction mixture was stirred at 90° C. for 3 h. It was then poured into H$_2$O (50 ml) and extracted with EtOAc (2×25 ml). The organic layers were dried over MgSO$_4$, filtered and concentrated in vacuo to give a crude product (2.370 g) which was purified by flash chromatography (silica gel, 20 g, 10% to 50% EtOAc in heptane) to yield the title compound (1.06 g, 72%) as light yellow amorphous solid. MS: 439.2 (MH$^+$).

Intermediate A-2

1-(2,2,2-Trifluoro-acetylamino)-cyclopropanecarboxylic acid[(S)-5-(4,4,5,5-tetramethyl-[1,3,2]dioxaborolan-2-yl)-indan-1-yl]-amide

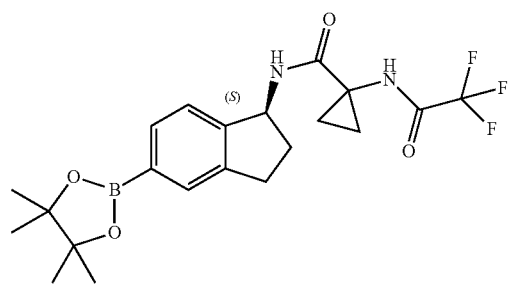

[A] (R)-5-Bromo-indan-1-ol and (S)-5-bromo-indan-1-ol

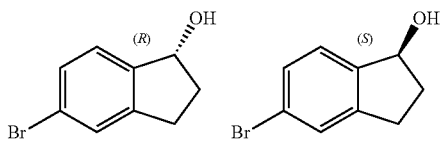

[S]-1-Methyl-3,3-diphenylhexahydropyrrolo[1,2-c][1,3,2]oxazaborole (7.11 ml, 7.11 mmol, eq: 0.15) was dissolved in CH$_2$Cl$_2$ (200 ml), borane-methyl sulfide complex (3.96 g, 4.95 ml, 52.1 mmol) was added with intense stirring and the solution was cooled to −70° C. Subsequently, a solution of 5-bromo-indan-1-one (10.0 g, 47.4 mmol) in CH$_2$Cl$_2$ (50.0 ml) was added drop by drop (0.5 ml/min.) below −75° C. The reaction mixture was then warmed up to RT over night very slowly in a CO$_2$/acetone bath. Now, cold water (50 ml) was added slowly (foaming) and the reaction mixture was extracted twice with CH$_2$Cl$_2$. The organic layers were dried over MgSO$_4$, filtered and concentrated in vacuo to give a crude product (10.786 g) which was purified by flash chromatography (silica gel, 100 g, 0% to 50% EtOAc in heptane) to give enriched title compound (9.716 g, R:S=88:12). This mixture was subsequently separated by HPLC chromatography (Chiralpak AD HPLC column, 5% EtOH in heptane) to give (R)-5-bromo-indan-1-ol, $[\alpha]^D_{(20\ deg)}$=−4.288, (c=1.259 in MeOH) (7.83 g, 78%) and (S)-5-bromo-indan-1-ol, $[\alpha]^D_{(20\ deg)}$=+4.294, (c=1.025 in MeOH) (1.16 g, 12%), both as light yellow solids.

[B] (S)-1-Azido-5-bromo-2,3-dihydro-1H-indene

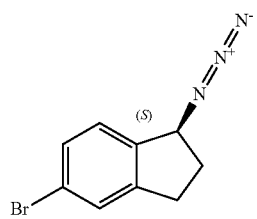

(R)-5-Bromo-indan-1-ol (7.47 g, 35.1 mmol) was dissolved in toluene (175 ml) and the mixture was cooled to 2° C., then treated with diphenylphosphoryl azide (12.5 g, 10.2 ml, 45.6 mmol), followed by a solution of 1,8-diazabicyclo[5.4.0]-undec-7-ene (7.47 g, 7.4 ml, 49.1 mmol) in toluene (3.0 ml). Subsequently, the reaction mixture was stirred for 2 h at 2-5° C. and then warmed up slowly to RT. It was then poured into $H_2O$ (200 ml) and extracted with EtOAc (2×150 ml). The organic layers were dried over $MgSO_4$, filtered and concentrated in vacuo to give a crude product (10.731 g) which was purified by flash chromatography (silica gel, 70 g, 5% to 10% EtOAc in heptane) to yield the title compound (8.10 g, 97%) as light yellow oil. MS: 236.9 ($M^+$, 1Br).

[C] (S)-5-Bromo-indan-1-ylamine

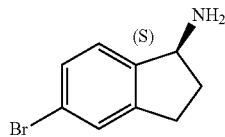

(S)-1-Azido-5-bromo-2,3-dihydro-1H-indene (8.09 g, 34.0 mmol) was dissolved in THF (155 ml), then water (17.2 ml) was added, followed by triphenylphosphine (9.8 g, 37.4 mmol). To this mixture, potassium hydroxide (1.0 N, 34.0 ml, 34.0 mmol) was added drop by drop below 25° C. and stirring continued over night at RT. The reaction mixture was then poured into $H_2O$ (150 ml) and extracted with EtOAc (2×100 ml). The organic layers were dried over $MgSO_4$, filtered and concentrated in vacuo to give a crude product (17.34 g), which was purified by flash chromatography (silica gel, 100 g, 0% to 40% MeOH in $CH_2Cl_2$) to yield the title compound (5.81 g, 81%) as light yellow oil. MS: 211 ($M^+$, 1Br).

[D] 1-(2,2,2-Trifluoro-acetylamino)-cyclopropanecarboxylic acid[(S)-5-(4,4,5,5-tetramethyl-[1,3,2]dioxaborolan-2-yl)-indan-1-yl]-amide

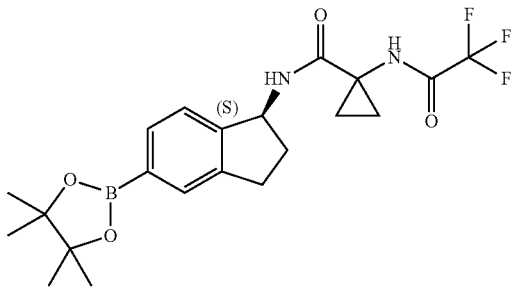

In analogy to the procedure described for the preparation of intermediate A-1 [B] and A-1 [C], (S)-5-bromo-indan-1-ylamine has been coupled with 1-(2,2,2-trifluoroacetamido)cyclopropanecarboxylic acid (intermediate A-1 [A]) to give 1-(2,2,2-trifluoro-acetylamino)-cyclopropanecarboxylic acid ((S)-5-bromo-indan-1-yl)-amide, which was subsequently reacted with 4,4,4',4',5,5,5',5'-octamethyl-2,2'-bi(1,3,2-dioxaborolane) to yield the title compound as light brown solid. MS: 439.3 ($MH^+$).

Intermediate A-3

3-(2,2,2-Trifluoro-acetylamino)-oxetane-3-carboxylic acid[(S)-5-(4,4,5,5-tetramethyl-[1,3,2]dioxaborolan-2-yl)-indan-1-yl]-amide

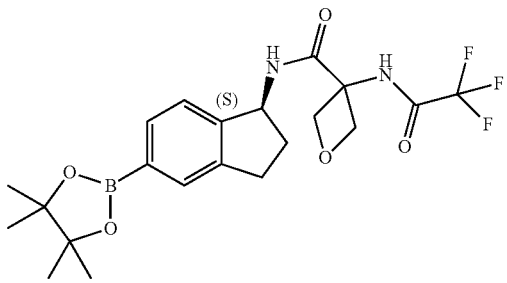

In analogy to the procedure described for the preparation of intermediate A-1 [B] and A-1 [C], (S)-5-bromo-indan-1-ylamine has been coupled with 3-(2,2,2-trifluoro-acetylamino)-oxetane-3-carboxylic acid (prepared from 3-amino-oxetane-3-carboxylic acid and trifluoro-acetic acid ethyl ester in analogy to the procedure described for the preparation of intermediate A-1 [A]) to give 3-(2,2,2-trifluoro-acetylamino)-oxetane-3-carboxylic acid ((S)-5-bromo-indan-1-yl)-amide, which was subsequently reacted with 4,4,4',4',5,5,5',5'-octamethyl-2,2'-bi(1,3,2-dioxaborolane) to yield the title compound as dark brown viscous oil. MS: 453.3 ($M-H^-$).

Intermediate A-4

1-(2,2,2-Trifluoro-acetylamino)-cyclopropanecarboxylic acid[(rac)-6-(4,4,5,5-tetramethyl-[1,3,2]dioxaborolan-2-yl)-1,2,3,4-tetrahydro-naphthalen-1-yl]-amide

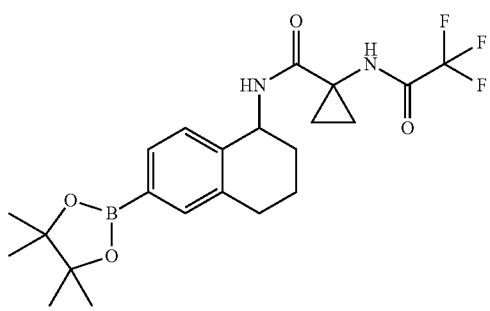 [SMILES: CC1(C)OB(c2ccc3c(c2)CCCC3NC(=O)C2(NC(=O)C(F)(F)F)CC2)OC1(C)C]

[A] (rac)-6-Bromo-1,2,3,4-tetrahydronaphthalen-1-amine

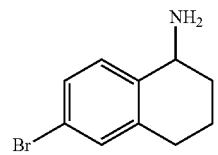 [SMILES: NC1CCCc2cc(Br)ccc21]

6-Bromo-3,4-dihydro-2H-naphthalen-1-one (9.5 g, 42.2 mmol) was suspended in 2-propanol (250 ml); then, NaBH$_3$CN (13.3 g, 211 mmol) was added, followed by ammonium acetate (65.1 g, 844 mmol). The reaction mixture was then stirred at RT for 4 hours. It was subsequently heated up to reflux and stirring was continued for 22 hours. The reaction mixture was then cooled down to RT and poured into cold H$_2$O (500 ml); the pH was adjusted to >10 with sodium hydroxide solution and the mixture was extracted with CH$_2$Cl$_2$ (2×25 ml). The organic layers were dried over MgSO$_4$, filtered and concentrated in vacuo to give a crude product (9.842 g) which was purified by flash chromatography (silica gel, 100 g, 2% to 10% MeOH in CH$_2$Cl$_2$) to yield the title compound (8.08 g, 85%) as light red oil. MS: 226.0 (MH$^+$, 1Br).

[B] 1-(2,2,2-Trifluoro-acetylamino)-cyclopropanecarboxylic acid[(rac)-6-(4,4,5,5-tetramethyl-[1,3,2]dioxaborolan-2-yl)-1,2,3,4-tetrahydro-naphthalen-1-yl]-amide

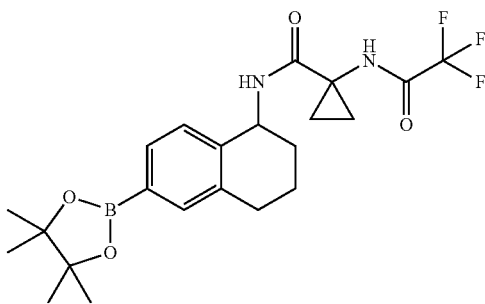 [SMILES: CC1(C)OB(c2ccc3c(c2)CCCC3NC(=O)C2(NC(=O)C(F)(F)F)CC2)OC1(C)C]

In analogy to the procedure described for the preparation of intermediate A-1 [B] and A-1 [C], (rac)-6-bromo-1,2,3,4-tetrahydronaphthalen-1-amine has been coupled with 1-(2,2,2-trifluoroacetamido)cyclopropanecarboxylic acid (intermediate A-1 [A]) to give 1-(2,2,2-trifluoro-acetylamino)-cyclopropanecarboxylic acid ((rac)-6-bromo-1,2,3,4-tetrahydro-naphthalen-1-yl)-amide, which was subsequently reacted with 4,4,4',4',5,5,5',5'-octamethyl-2,2'-bi(1,3,2-dioxaborolane) to yield the title compound as light brown oil. MS: 453.2 (MH$^+$).

Intermediate A-5

1-(2,2,2-Trifluoro-acetylamino)-cyclopropanecarboxylic acid ((rac)-3-bromo-6,7-dihydro-5H-[1]pyrindin-7-yl)-amide

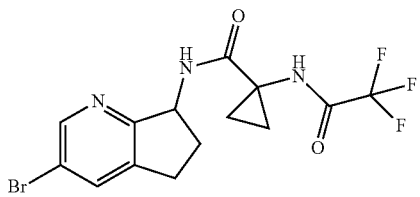 [SMILES: O=C(NC1(C(=O)NC2CCc3cc(Br)cnc32)CC1)C(F)(F)F]

[A] (rac)-3-Bromo-6,7-dihydro-5H-[1]pyrindin-7-ol

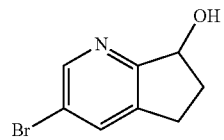 [SMILES: OC1CCc2cc(Br)cnc21]

3-Bromo-6,7-dihydro-5H-[1]pyrindine 1-oxide (6.97 g, 32.6 mmol) was dissolved in CH$_2$Cl$_2$ (150 ml); then, trifluoroacetic anhydride (20.5 g, 13.6 ml, 97.7 mmol) was added drop by drop below 25° C. with intense stirring and stirring was continued for 6 hours at RT. The mixture was then quenched with aqueous 1M NaOH solution. The aqueous mixture was stirred for two hours and extracted three times with CH$_2$Cl$_2$/2-propanol 4:1. The organic layers were dried over MgSO$_4$, filtered and concentrated in vacuo to give a crude product (6.279 g) which was purified by flash chromatography (silica gel, 50 g, 20% to 100% EtOAc in heptane) to yield the title compound (5.38 g, 77%) as light brown solid. MS: 214.0 (MH$^+$, 1Br).

[B] (rac)-3-Bromo-6,7-dihydro-5H-[1]pyrindin-7-ylamine

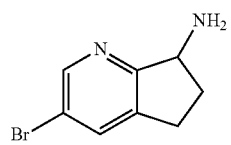 [SMILES: NC1CCc2cc(Br)cnc21]

(rac)-3-Bromo-6,7-dihydro-5H-[1]pyrindin-7-ol (4.84 g, 22.6 mmol) and isoindoline-1,3-dione (3.66 g, 24.9 mmol) were dissolved in THF (130 ml); then, triphenylphosphine (7.41 g, 28.3 mmol) was added, followed by a solution of di-tert-butyl azodicarboxylate (6.25 g, 27.1 mmol) in THF (3.0 ml) below 5° C.; stirring at RT was then continued for 20 hours. The reaction mixture was concentrated in vacuo to give a crude product (23.507 g), which was purified by flash chromatography (silica gel, 100 g, 10% to 50% EtOAc in heptane) to give 2-((rac)-3-bromo-6,7-dihydro-5H-cyclopenta[b]pyridin-7-yl)isoindoline-1,3-dione (11.114 g, not pure). This intermediate was dissolved in ethanol (140 ml), then, while stirring, hydrazine hydrate (3.01 g, 2.95 ml, 75.1 mmol) was added and the reaction mixture was heated up to reflux. After 2 hours, it was poured into NaOH 1N (150 ml) and extracted with CH$_2$Cl$_2$ (2×100 ml). The organic layers were dried over MgSO$_4$, filtered and concentrated in vacuo to give a crude product (8.845 g) which was purified by flash chromatography (silica gel, 100 g, 0% to 20% MeOH in CH$_2$Cl$_2$) to yield the title compound (1.80 g, 37%) as purple oil. MS: 213.0 (MH$^+$, 1Br).

[C] 1-(2,2,2-Trifluoro-acetylamino)-cyclopropanecarboxylic acid ((rac)-3-bromo-6,7-dihydro-5H-[1]pyrindin-7-yl)-amide

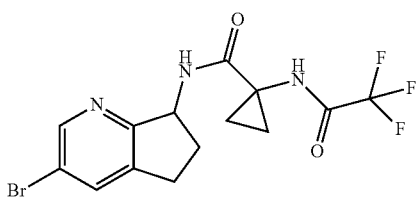 [SMILES: O=C(NC1(C(=O)NC2CCc3cc(Br)cnc32)CC1)C(F)(F)F]

In analogy to the procedure described for the preparation of intermediate A-1 [B], (rac)-3-bromo-6,7-dihydro-5H-[1]pyrindin-7-ylamine has been coupled with 1-(2,2,2-trifluoroacetamido)cyclopropanecarboxylic acid (intermediate A-1 [A]) to yield the title compound as grey solid. MS: 392.0 (MH⁺, 1Br).

Intermediate A-6

1-(2,2,2-Trifluoro-acetylamino)-cyclopropanecarboxylic acid[(rac)-7-(4,4,5,5-tetramethyl-[1,3,2]dioxaborolan-2-yl)-chroman-4-yl]-amide

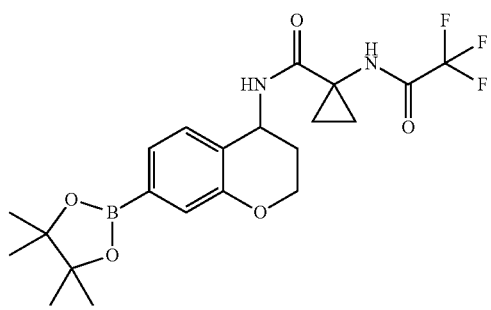 [SMILES: CC1(C)OB(c2ccc3c(c2)OCCC3NC(=O)C2(NC(=O)C(F)(F)F)CC2)OC1(C)C]

[A] (rac)-7-Bromo-chroman-4-ylamine

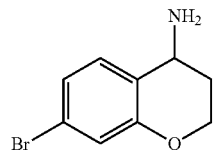 [SMILES: NC1CCOc2cc(Br)ccc21]

In analogy to the procedures described for the preparation of intermediates A-2 [B] and A-2 [C], (rac)-7-bromo-chroman-4-ol prepared from 7-bromo-chroman-4-one with sodium borohydride in ethanol at 60-70° C., was treated with diphenylphosphoryl azide, DBU in toluene to give (rac)-4-azido-7-bromo-chroman, which was subsequently reduced with triphenylphosphine in THF/water to yield the title compound as light yellow oil. MS: 227 (M⁺, 1Br).

[B] 1-(2,2,2-Trifluoro-acetylamino)-cyclopropanecarboxylic acid[(rac)-7-(4,4,5,5-tetramethyl-[1,3,2]dioxaborolan-2-yl)-chroman-4-yl]-amide

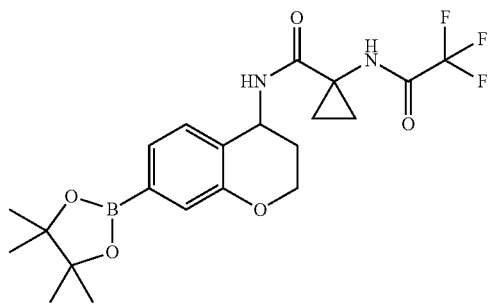 [SMILES: CC1(C)OB(c2ccc3c(c2)OCCC3NC(=O)C2(NC(=O)C(F)(F)F)CC2)OC1(C)C]

In analogy to the procedure described for the preparation of intermediate A-1 [B] and A-1 [C], (rac)-7-bromo-chroman-4-ylamine has been coupled with 1-(2,2,2-trifluoroacetamido) cyclopropanecarboxylic acid (intermediate A-1 [A]) to give 1-(2,2,2-trifluoro-acetylamino)-cyclopropanecarboxylic acid ((rac)-7-bromo-chroman-4-yl)-amide, which was subsequently reacted with 4,4,4',4',5,5,5',5'-octamethyl-2,2'-bi(1,3,2-dioxaborolane) to yield the title compound as light yellow solid. MS: 453.2 (M–H⁻).

Intermediate A-7

1-(2,2,2-Trifluoro-acetylamino)-cyclopropanecarboxylic acid[(rac)-7-fluoro-5-(4,4,5,5-tetramethyl-[1,3,2]dioxaborolan-2-yl)-indan-1-yl]-amide

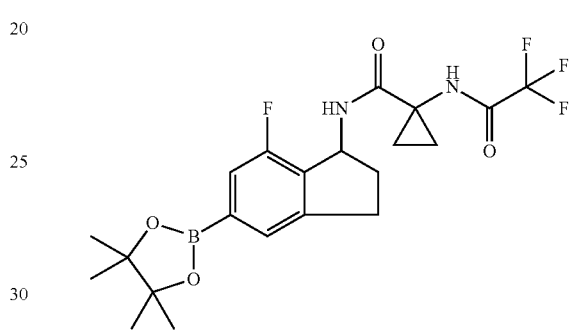

[A] 1-(4-Bromo-2-fluoro-phenyl)-3-chloro-propan-1-one

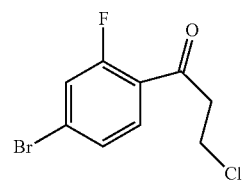 [SMILES: O=C(CCCl)c1ccc(Br)cc1F]

To a suspension of 4-bromo-2-fluoro-benzoic acid (10 g, 45.65 mmol) in benzene (50 ml) was added thionyl chloride (7.8 ml, 12.79 g, 91.32 mmol) and the resulting mixture was heated to reflux for 12 hours. Thionyl chloride was evaporated, the reaction mixture was diluted with 1,2-dichloroethane (50 ml) and added to a slurry of aluminum chloride (5.7 g, 42.53 mmol) in 1,2 dichloroethane (50 ml) at room temperature. Ethylene was bubbled through the reaction mixture for 5 hours and the reaction mixture was stirred for another 2 hours at room temperature. It was then quenched with 2N HCl (50 ml). The layers were separated. The aqueous phase was extracted twice with 100 ml dichloromethane. The combined organic phases were washed with saturated sodium bicarbonate solution (50 ml) followed by water (50 ml). It was then dried over Na₂SO₄ and evaporated under reduced pressure to get the crude product, which was purified subsequently by column chromatography (silica gel, 0-5% ethyl acetate/hexane) to afford 8.6 g (71%) of the title compound as reddish solid.

[B] 5-Bromo-7-fluoro-indan-1-one

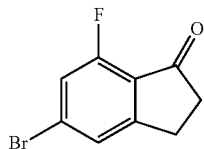 [SMILES: O=C1CCc2cc(Br)cc(F)c21]

To a mixture of AlCl$_3$ (37.5 g, 282.48 mmol) and NaCl (11 g, 188.32 mmol) was added 1-(4-bromo-2-fluoro-phenyl)-3-chloro-propan-1-one (5 g, 18.83 mmol) at 130° C. The reaction temperature was slowly increased to 180° C. and kept for 1 hour. It was cooled, the mixture was poured into ice and extracted twice with ethyl acetate (2×100 ml). The combined ethyl acetate phases were dried over Na$_2$SO$_4$ and evaporated to get the crude product which was purified by column chromatography (silica gel, 5-10% ethyl acetate/hexane) to give 2.4 g (55%) of the title compound as brown solid. MS: 229.2 (MH$^+$, 1Br).

[C] (rac)-5-Bromo-7-fluoro-indan-1-ylamine

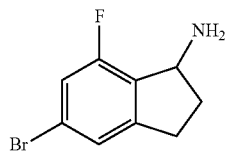 [SMILES: NC1CCc2cc(Br)cc(F)c21]

In analogy to the procedure described for the preparation of intermediates A-4 [A], 5-bromo-7-fluoro-indan-1-one was reacted with sodium cyanoborohydride and ammonium acetate in 2-propanol at reflux to yield the title compound as light yellow oil. MS: 228 (M−H$^−$, 1Br).

[D] 1-(2,2,2-Trifluoro-acetylamino)-cyclopropanecarboxylic acid[(rac)-7-fluoro-5-(4,4,5,5-tetramethyl-[1,3,2]dioxaborolan-2-yl)-indan-1-yl]-amide

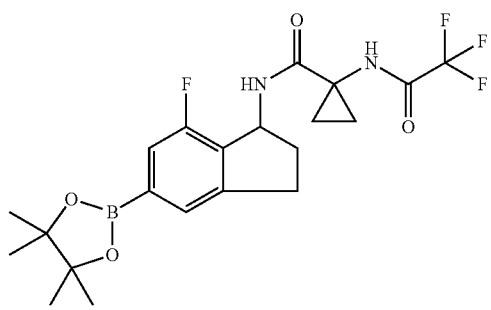 [SMILES: CC1(C)OB(c2cc(F)c3c(c2)CCC3NC(=O)C2(NC(=O)C(F)(F)F)CC2)OC1(C)C]

In analogy to the procedure described for the preparation of intermediate A-1 [B] and A-1 [C], (rac)-5-bromo-7-fluoro-indan-1-ylamine has been coupled with 1-(2,2,2-trifluoroacetamido)cyclopropanecarboxylic acid (intermediate A-1 [A]) to give 1-(2,2,2-trifluoro-acetylamino)-cyclopropanecarboxylic acid ((rac)-5-bromo-7-fluoro-indan-1-yl)-amide, which was subsequently reacted with 4,4,4',4',5,5,5',5'-octamethyl-2,2'-bi(1,3,2-dioxaborolane) to yield the title compound as light yellow amorphous solid. MS: 455.2 (M−H$^−$).

Intermediate A-8

1-(2,2,2-Trifluoro-acetylamino)-cyclopropanecarboxylic acid[(rac)-6-(4,4,5,5-tetramethyl-[1,3,2]dioxaborolan-2-yl)-2,3-dihydro-benzofuran-3-yl]-amide

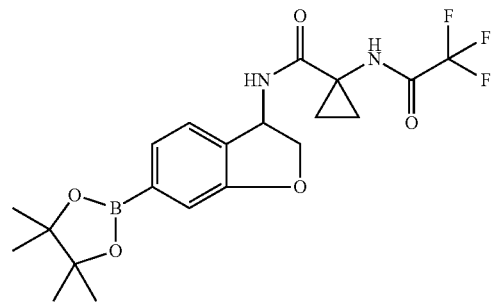 [SMILES: CC1(C)OB(c2ccc3c(c2)OCC3NC(=O)C2(NC(=O)C(F)(F)F)CC2)OC1(C)C]

[A] (rac)-6-Bromo-2,3-dihydro-benzofuran-3-ol

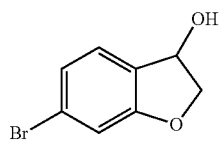 [SMILES: OC1COc2cc(Br)ccc21]

To a solution of 6-bromo-benzofuran-3-one (10.5 g, 49.28 mmol) in methanol (100 ml) was added NaBH$_4$ (2.37 g, 64.07 mmol) at 0° C. The reaction mixture was then stirred for 2 hours at room temperature. It was subsequently quenched with saturated ammonium chloride solution (50 ml) and extracted twice with ethyl acetate (2×50 ml). The combined organic phases were dried over Na$_2$SO$_4$ and evaporated under reduced pressure to give 9.75 g (92%) of the title compound as colorless liquid.

[B]
(rac)-6-Bromo-2,3-dihydro-benzofuran-3-ylamine

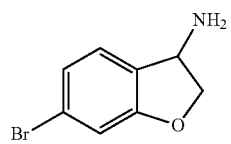 [SMILES: NC1COc2cc(Br)ccc21]

In analogy to the procedures described for the preparation of intermediates A-2 [B] and A-2 [C], (rac)-6-bromo-2,3-dihydro-benzofuran-3-ol was treated with diphenylphosphoryl azide, DBU in toluene to give (rac)-3-azido-6-bromo-2,3-dihydro-benzofuran, which was subsequently reduced with triphenylphosphine in THF/water to yield the title compound as light yellow oil. MS: 213 (M$^+$, 1Br).

[C] 1-(2,2,2-Trifluoro-acetylamino)-cyclopropan-ecarboxylic acid[(rac)-6-(4,4,5,5-tetramethyl-[1,3,2]dioxaborolan-2-yl)-2,3-dihydro-benzofuran-3-yl]-amide

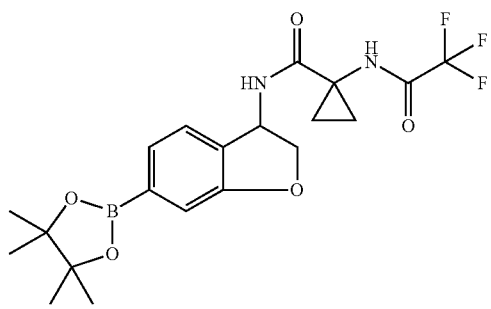

In analogy to the procedure described for the preparation of intermediate A-1 [B] and A-1 [C], (rac)-6-bromo-2,3-dihydro-benzofuran-3-ylamine has been coupled with 1-(2,2,2-trifluoroacetamido)cyclopropanecarboxylic acid (intermediate A-1 [A]) to give 1-(2,2,2-trifluoro-acetylamino)-cyclopropanecarboxylic acid ((rac)-6-bromo-2,3-dihydro-benzofuran-3-yl)-amide, which was subsequently reacted with 4,4,4',4',5,5,5',5'-octamethyl-2,2'-bi(1,3,2-dioxaborolane) to yield the title compound as light brown solid. MS: 439.2 (M−H⁻).

Intermediate A-9

1-(2,2,2-Trifluoro-acetylamino)-cyclopropanecarboxylic acid[(rac)-6-(4,4,5,5-tetramethyl-[1,3,2]dioxaborolan-2-yl)-2,3-dihydro-benzo[b]thiophen-3-yl]-amide

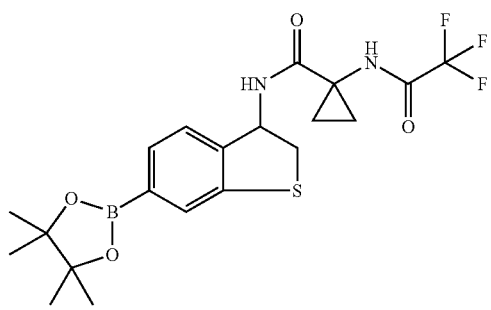 [SMILES: CC1(C)OB(c2ccc3c(c2)OCC3NC(=O)C2(NC(=O)C(F)(F)F)CC2)OC1(C)C]

[A] (rac)-6-Bromo-2,3-dihydro-benzo[b]thiophen-3-ylamine

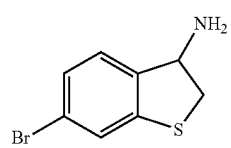 [SMILES: NC1CSc2cc(Br)ccc21]

In analogy to the procedures described for the preparation of intermediate A-8 [A], intermediates A-2 [B] and A-2 [C], 6-bromo-benzo[b]thiophen-3-one was reacted with sodium borohydride in ethanol to give (rac)-6-bromo-2,3-dihydro-benzo[b]thiophen-3-ol, which was subsequently reacted with diphenylphosphoryl azide, DBU in toluene to give (rac)-3-azido-6-bromo-2,3-dihydro-benzo[b]thiophene, which was then reduced with triphenylphosphine in THF/water to yield the title compound as light yellow oil. MS: 229 (M⁺, 1Br).

[B] 1-(2,2,2-Trifluoro-acetylamino)-cyclopropan-ecarboxylic acid[(rac)-6-(4,4,5,5-tetramethyl-[1,3,2]dioxaborolan-2-yl)-2,3-dihydro-benzo[b]thiophen-3-yl]-amide

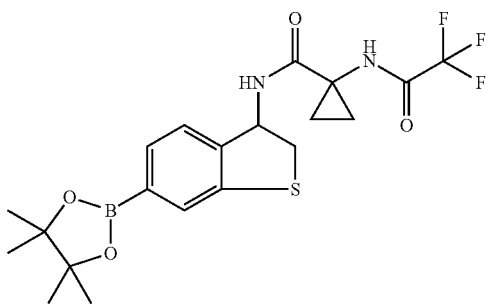

In analogy to the procedure described for the preparation of intermediate A-1 [B] and A-1 [C], (rac)-6-bromo-2,3-dihydro-benzo[b]thiophen-3-ylamine has been coupled with 1-(2,2,2-trifluoroacetamido)cyclopropanecarboxylic acid (intermediate A-1 [A]) to give 1-(2,2,2-trifluoro-acetylamino)-cyclopropanecarboxylic acid ((rac)-6-bromo-2,3-dihydro-benzo[b]thiophen-3-yl)-amide, which was subsequently reacted with 4,4,4',4',5,5,5',5'-octamethyl-2,2'-bi(1,3,2-dioxaborolane) to yield the title compound as yellow oil. MS: 455.4 (M−H⁻).

Intermediate A-10

1-(2,2,2-Trifluoro-acetylamino)-cyclopropanecarboxylic acid ((rac)-5-bromo-1-methyl-indan-1-yl)-amide

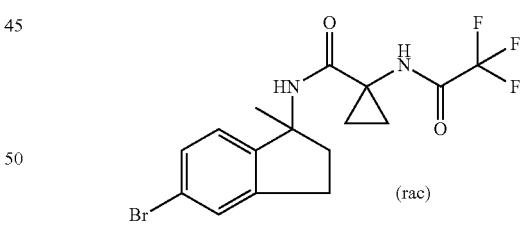

[A] (rac)-5-Bromo-1-[1,3]dithian-2-yl-indan-1-ol

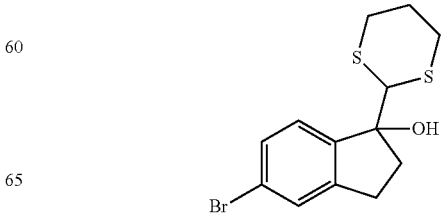

To a solution of 1,3-dithiane (1.82 g, 14.7 mmol) in dry THF (20 ml) was added n-butyllithium (8.62 ml, 13.8 mmol, 1.6 M in hexane) dropwise at −30° C. The resulting mixture was stirred for 2 h at −15° C. Then, a solution of 5-bromo-2, 3-dihydro-1H-inden-1-one (2 g, 9.19 mmol) in dry THF (24 ml) was added dropwise, maintaining the temperature between −15° C. and −6° C. After the addition was completed, the brown solution was allowed to warm to 0° C. and was then stored in the fridge overnight. Then, 1N HCl was added and the brown mixture was extracted two times with diethylether. The combined organic layers were washed with brine, dried with $Na_2SO_4$ and evaporated. The remaining residue was purified by chromatography (silica gel; heptane/EtOAc 90:10-75:25) to obtain the title compound as light yellow gum (2.167 g, 71%). MS: 330.1 $[M+H]^+$.

[B] 2-(5-Bromo-indan-1-ylidene)-[1,3]dithiane

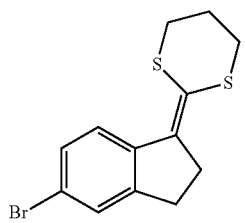 [SMILES: Brc1ccc2c(c1)CCC2=C1SCCCS1]

A mixture of (rac)-5-bromo-1-[1,3]dithian-2-yl-indan-1-ol (2.15 g, 6.49 mmol) and p-toluenesulfonic acid monohydrate (309 mg, 1.62 mmol) in benzene (30 ml) was heated to reflux for 2 h using a Dean-Stark trap to remove water. The brown solution was allowed to cool to room temperature and was diluted with sat. $NaHCO_3$ solution. The layers were separated and the organic layer was washed with brine, dried with $Na_2SO_4$ and evaporated. The title compound was obtained as brown gum (2.024 g, 99%) and was used without purification for the next reaction step.

[C] (rac)-5-Bromo-indan-1-carboxylic acid

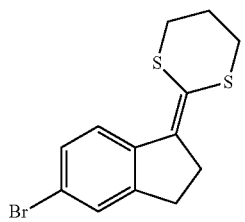 [SMILES: Brc1ccc2c(c1)CCC2=C1SCCCS1]

To a mixture of 2-(5-bromo-indan-1-ylidene)-[1,3] dithiane (2.02 g, 6.45 mmol) in acetic acid (34 ml) was added 37% HCl (11 ml). After the addition, the brown mixture was heated to reflux for 3 h; then, the reaction mixture was allowed to cool to room temperature and was concentrated to dryness, using toluene as co-evaporating solvent to remove acetic acid and water. This process was repeated four times. The remaining brown oil was purified by chromatography (silica gel; $CH_2Cl_2$/EtOAc 100:0-0:100) to obtain the title compound as light brown solid (1.335 g, 86%). MS: 238.6 $[M−H]^−$.

[D] (rac)-5-Bromo-indan-1-carboxylic acid methyl ester

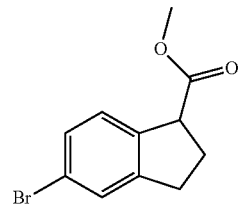

A solution of (rac)-5-bromo-indan-1-carboxylic acid (1.326 g, 5.5 mmol) in MeOH (55 ml) was treated with 4N HCl in dioxane (15 ml) and the mixture was stirred at reflux for 7 h. The yellow solution was allowed to cool to room temperature and all volatiles were removed. The remaining brown oil was purified by chromatography (silica gel; heptane/EtOAc 95:5) to obtain the title compound as light yellow oil (1.31 g, 93%).

[E] (rac)-5-Bromo-1-methyl-indan-1-carboxylic acid methyl ester

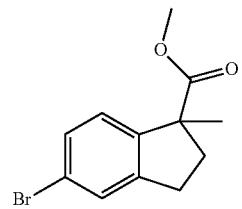

Lithium bis(trimethylsilyl)amide (6.16 ml, 6.16 mmol, 1M solution in THF) was added dropwise to a solution of (rac)-5-bromo-indan-1-carboxylic acid methyl ester (1.31 g, 5.14 mmol) in dry THF (25 ml) at −78° C. After the addition was completed, the solution was stirred at −78° C. for 45 minutes. Then, iodomethane (2.19 g, 959 µl, 15.4 mmol) was added, the solution was allowed to warm to room temperature and stirred for 48 h. The reaction was quenched by addition of sat. $NH_4Cl$ solution and extracted two times with EtOAc. The combined organic layers were washed with brine, dried with $Na_2SO_4$ and evaporated. The remaining yellow oil was purified by chromatography (silica gel; heptane/EtOAc 95:5) to obtain the title compound as yellow oil (1.319 g, 95%). MS: 269.2 $[M+H]^+$.

[F] (rac)-5-Bromo-1-methyl-indan-1-carboxylic acid

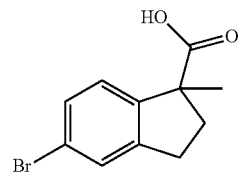

A solution of (rac)-5-bromo-1-methyl-indan-1-carboxylic acid methyl ester (1.318 g, 4.9 mmol) and potassium trimethylsilanolate (3.14 g, 24.5 mmol) in dry THF (25 ml) was stirred at reflux for 1 h. The reaction mixture was allowed to cool to room temperature, water was added and the mixture was extracted two times with tert-butyl methylether. The pH of the aqueous layer was carefully adjusted to 3 by addition of 1N HCl and the aqueous layer was extracted two times with EtOAc. The combined EtOAc-layers were washed with brine, dried with $Na_2SO_4$ and evaporated. Toluene was added to the remaining residue and it was evaporated to remove water. The title compound was obtained as light yellow solid (1.204 g, 96%). MS: 252.7 $[M-H]^-$.

[G] (rac)-5-Bromo-1-methyl-indan-1-ylamine

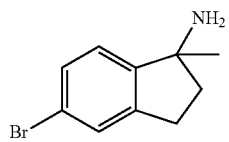

To a solution of (rac)-5-bromo-1-methyl-indan-1-carboxylic acid (1.197 g, 4.69 mmol) in dry toluene (65 ml) was added triethylamine (570 mg, 475 μl, 5.63 mmol) and diphenylphosphoryl azide (1.33 g, 1.04 ml, 4.69 mmol) and the colorless solution was heated to reflux for 3 h. After cooling to 0° C., sodium trimethylsilanolate (9.38 ml, 9.38 mmol, 1M solution in THF) was added and the mixture was stirred for 30 minutes at room temperature. After quenching the reaction with 5% citric acid (100 ml), the pH was adjusted to 12-13 by addition of 3N NaOH and the mixture was extracted three times with $CH_2Cl_2$. The combined organic layers were washed with brine, dried with $Na_2SO_4$ and evaporated. The remaining crude material was partitioned between 0.1N HCl and diethylether and the aqueous layer was extracted with diethylether. The pH of the aqueous layer was adjusted to 12 by addition of 0.1N NaOH and the aqueous layer was extracted three times with $CH_2Cl_2$. The combined $CH_2Cl_2$-layers were washed with brine, dried with $Na_2SO_4$ and evaporated to obtain the title compound as light yellow oil (963 mg, 91%). MS: 209.1 $[M+H-NH_3]^+$.

[H] 1-(2,2,2-Trifluoro-acetylamino)-cyclopropanecarboxylic acid ((rac)-5-bromo-1-methyl-indan-1-yl)-amide

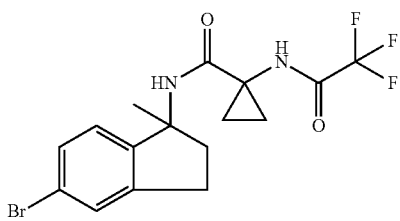 [SMILES: CC1(NC(=O)C2(NC(=O)C(F)(F)F)CC2)CCc2cc(Br)ccc21]

In analogy to the procedure described for the preparation of intermediate A-1 [B], (rac)-5-bromo-1-methyl-indan-1-ylamine has been coupled with 1-(2,2,2-trifluoroacetamido)cyclopropanecarboxylic acid (intermediate A-1 [A]) to yield the title compound as light brown solid. MS: 402.9 (M-H$^-$, 1Br).

Intermediate A-11

(S)-5-[5-Chloro-3-fluoro-2-(5-methyl-[1,2,4]oxadiazol-3-yl)-phenyl]-indan-1-ylamine

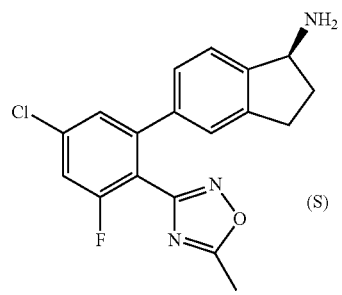 [SMILES: Cc1nc(-c2c(F)cc(Cl)cc2-c2ccc3c(c2)CC[C@@H]3N)no1 ; "(S)"]

[A] ((S)-5-Bromo-indan-1-yl)-carbamic acid tert-butyl ester

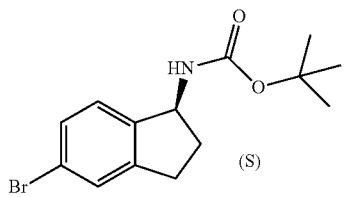

Di-tert-butyl dicarbonate (4.7 g, 21.6 mmol) and (S)-5-bromo-indan-1-ylamine (intermediate A-2 [C]) (3.81 g, 18.0 mmol) were dissolved in dioxane (40.0 ml); then, a solution of sodium bicarbonate (3.32 g, 39.5 mmol) in water (10 ml) was added while stirring and stirring at RT was continued for 20 hours. The reaction mixture was then treated with NaOH (5N, 20 ml) and stirring continued vigorously for 90 minutes (decomposition of $BOC_2O$). The reaction mixture was then poured into $H_2O$ (100 ml) and extracted with EtOAc (2×50 ml). The organic layers were dried over $MgSO_4$, filtered and concentrated in vacuo to give a crude product (5.690 g) which was purified by flash chromatography (silica gel, 20 g, 0% to 20% EtOAc in heptane) to yield the title compound (5.31 g, 95%) as colorless solid. MS: 331.1 ($MNH_4^+$, 1Br).

[B] {(S)-5-[5-Chloro-3-fluoro-2-(5-methyl-[1,2,4]oxadiazol-3-yl)-phenyl]-indan-1-yl}-carbamic acid tert-butyl ester

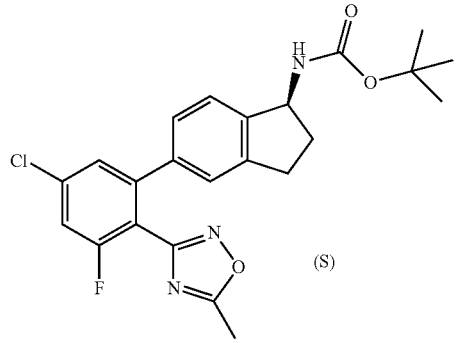 [SMILES: Cc1nc(-c2c(F)cc(Cl)cc2-c2ccc3c(c2)CC[C@@H]3NC(=O)OC(C)(C)C)no1 ; "(S)"]

In analogy to the procedures described for the preparation of intermediates A-1 [C] and example 5, ((S)-5-bromo-indan-1-yl)-carbamic acid tert-butyl ester has been reacted with 4,4,4',4',5,5,5',5'-octamethyl-2,2'-bi(1,3,2-dioxaborolane) to give [(S)-5-(4,4,5,5-tetramethyl-[1,3,2]dioxaborolan-2-yl)-indan-1-yl]-carbamic acid tert-butyl ester, which was further reacted with 3-(2-bromo-4-chloro-6-fluoro-phenyl)-5-methyl-[1,2,4]oxadiazole (intermediate B-2) to give the title compound as yellow amorphous solid. MS: 444.2 (MH+, 1Cl).

[C] (S)-5-[5-Chloro-3-fluoro-2-(5-methyl-[1,2,4]oxadiazol-3-yl)-phenyl]-indan-1-ylamine

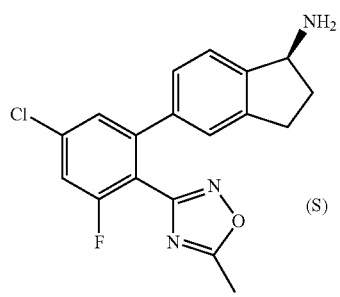 [SMILES: Cc1nc(-c2c(F)cc(Cl)cc2-c2ccc3c(c2)CC[C@@H]3N)no1 ; "(S)"]

{(S)-5-[5-Chloro-3-fluoro-2-(5-methyl-[1,2,4]oxadiazol-3-yl)-phenyl]-indan-1-yl}-carbamic acid tert-butyl ester (0.22 g, 496 μmol) was dissolved in CH$_2$Cl$_2$ (10.0 ml); then, while stirring, 2,2,2-trifluoroacetic acid 90% (628 μl, trifluoroacetic acid 100%/water=9:1 (v/v)) was added and stirring at RT was continued for 25 hours. The reaction mixture was then poured into a saturated aqueous K$_2$CO$_3$ solution and extracted twice with CH$_2$Cl$_2$. The organic layers were dried over MgSO$_4$, filtered and concentrated in vacuo to give a crude product (0.173 g) which was purified by flash chromatography (silica gel, CH$_2$Cl$_2$/MeOH) to yield the title compound (0.129 g, 76%) as light yellow oil. MS: 344.1 (MH+, 1Cl).

Intermediate A-12

(3-{(S)-5-[5-Chloro-3-fluoro-2-(5-methyl-[1,2,4]oxadiazol-3-yl)-phenyl]-indan-1-ylcarbamoyl}-oxetan-3-yl)-carbamic acid 9H-fluoren-9-ylmethyl ester

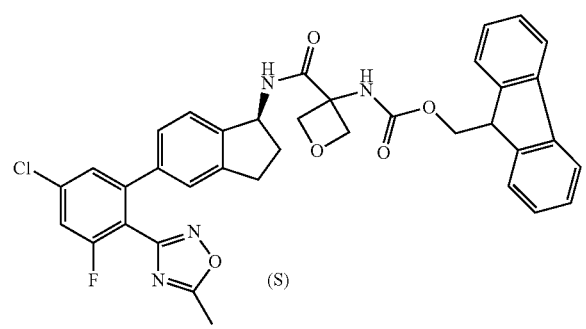 [SMILES: Cc1nc(-c2c(F)cc(Cl)cc2-c2ccc3c(c2)CC[C@@H]3NC(=O)C2(NC(=O)OCC3c4ccccc4-c4ccccc43)COC2)no1 ; "(S)"]

[A] 3-(9H-Fluoren-9-ylmethoxycarbonylamino)-oxetane-3-carboxylic acid

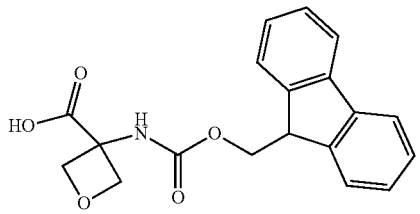 [SMILES: O=C(NC1(C(=O)O)COC1)OCC1c2ccccc2-c2ccccc21]

A solution of (9H-fluoren-9-yl)methyl 2,5-dioxopyrrolidin-1-yl carbonate (3.2 g, 9.5 mmol) in dioxane (30 ml) was added to a solution of 3-amino-oxetane-3-carboxylic acid (1.17 g, mmol) and potassium carbonate (2.76 g, 20.0 mmol) in water (30 ml). The light yellow opaque solution was stirred at room temperature for 75 minutes. During that time, a white solid precipitated. The mixture was diluted with water and extracted two times with diethyl ether. The white solid did not dissolve and was kept therefore in the aqueous layer, which was acidified to pH 2 by addition of 1N HCl and extracted three times with EtOAc. The combined EtOAc layers were washed with brine, dried with Na$_2$SO$_4$ and evaporated. The crude title compound was obtained as white solid and was used without further purification.

[B] (3-{(S)-5-[5-Chloro-3-fluoro-2-(5-methyl-[1,2,4]oxadiazol-3-yl)-phenyl]-indan-1-ylcarbamoyl}-oxetan-3-yl)-carbamic acid 9H-fluoren-9-ylmethyl ester

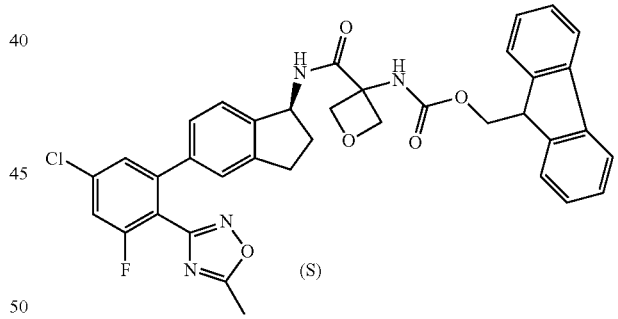

To a solution of 3-(9H-fluoren-9-ylmethoxycarbonylamino)-oxetane-3-carboxylic acid (1.70 g, 5.01 mmol) in dry DMF (50.0 ml) were added N-(3-dimethylaminopropyl)-N'-ethylcarbodiimide hydrochloride (1.60 g, 8.35 mmol) and 1-hydroxybenzotriazole hydrate (0.95 g, 6.20 mmol) at room temperature. The resulting colorless solution was stirred for 10 min before a solution of (S)-5-[5-chloro-3-fluoro-2-(5-methyl-[1,2,4]oxadiazol-3-yl)-phenyl]-indan-1-ylamine (1.64 g, 4.77 mmol, intermediate A-11) in dry DMF (2.0 ml) was added. This mixture was stirred at room temperature for 20 h. Then water was added, the pH was adjusted to 9 with sat. K$_2$CO$_3$ solution and the mixture was extracted twice with MeCl$_2$. The combined organic layers were washed with water and brine, dried with MgSO$_4$ and evaporated. The remaining light brown foam was purified by chromatography (silica gel;

MeCl₂/MeOH 100:0 to 98:2%) and the title compound was obtained as off white foam (3.17 g, 100%). MS: 665.2 (MH⁺, 1Cl).

Intermediate B-1

1-Bromo-3,5-dichloro-2-(2,2-difluoro-ethoxy)-benzene

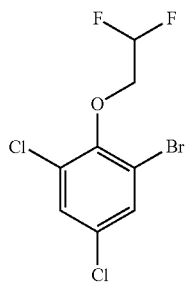 [SMILES: FC(F)COc1c(Cl)cc(Cl)cc1Br]

[A] 2-Bromo-4,6-dichloro-phenol

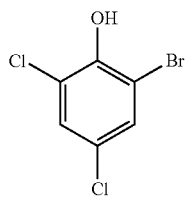

To a solution of 2,4-dichloro-phenol (15 g, 19.02 mmol) in toluene (200 ml) was added bromine (5.1 ml, 184.04 mmol) dropwise at −50° C. Then, tert-butylamine (19.4 ml, 99.02 mmol) was added dropwise and the reaction mixture was stirred at −50° C. for 30 minutes. The reaction was quenched by addition of 38% aqueous NaHSO₃ solution, the organic layer was separated and the aqueous layer was extracted two times with EtOAc. The combined organic extracts were dried with Na₂SO₄, filtered and evaporated to obtain the title compound (21.5 g, 96%) as white solid.

[B] Methanesulfonic acid 2,2-difluoro-ethyl ester

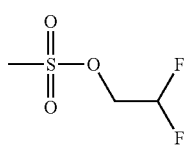

To a solution of 2,2-difluoro-ethanol (6 g, 73.12 mmol) and mesyl chloride (6.26 ml, 80.43 mmol) in CH₂Cl₂ (40 ml) was added triethylamine (12.66 ml, 87.74 mmol) dropwise at 0° C. After the addition was completed, the mixture was allowed to warm to room temperature and was stirred for 1 h. The reaction mixture was then washed two times with water and with brine and dried with Na₂SO₄. Evaporation of the solvent yielded the title compound (10.7 g, 92%) as yellow liquid.

[C] 1-Bromo-3,5-dichloro-2-(2,2-difluoro-ethoxy)-benzene

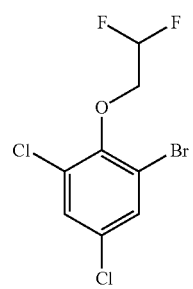 [SMILES: FC(F)COc1c(Cl)cc(Cl)cc1Br]

To a solution of 2-bromo-4,6-dichloro-phenol (14.6 g, 60.3 mmol) (intermediate B-1 [A]) in DMF (10 ml) were added K₂CO₃ (16.53 g, 120.6 mmol) and methanesulfonic acid 2,2-difluoro-ethyl ester (10.7 g, 66.4 mmol) (intermediate B-1 [B]) and the mixture was heated to reflux for 16 h. The DMF was then evaporated in vacuo and the resulting residue was dissolved in EtOAc (300 ml). This solution was washed two times with water, with brine, dried with Na₂SO₄ and evaporated. The remaining crude product was purified by chromatography (silica gel; hexane) and the title compound (14.5 g, 79%) was obtained as white solid. MS: 304 (M⁺, 1Br).

Intermediate B-2

3-(2-Bromo-4-chloro-6-fluoro-phenyl)-5-methyl-[1,2,4]oxadiazole

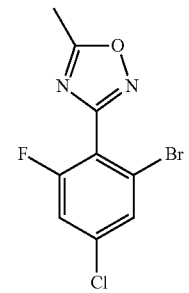

[A] 2-Bromo-4-chloro-6-fluoro-benzaldehyde

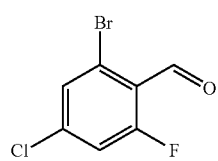 [SMILES: O=Cc1c(F)cc(Cl)cc1Br]

To a solution of 1,2-dibromo-5-chloro-3-fluoro-benzene (10 g, 34.68 mmol) in heptane (27 ml) was added THF (44 ml) and the mixture was cooled to −45° C. Then, iPrMgCl (38.14 ml, 38.14 mmol, 1M solution in THF) was added dropwise to the reaction mixture maintaining the temperature between −40° C. to −45° C. The mixture was stirred for 30 minutes at −40° C. before DMF (13.4 ml, 173.4 mmol) was added dropwise to the reaction mixture maintaining the temperature between −45° C. to −20° C. After stirring for another 15 minutes at −20° C., it was poured into a mixture of 2N HCl (20 ml) and ether (50 ml) at 0° C. The organic layer was separated and the aqueous layer was extracted two times with ether. The combined organic layers were dried with $Na_2SO_4$ and evaporated in vacuo to obtain the title compound (7.8 g, 95%) as yellow solid.

[B] 2-Bromo-4-chloro-6-fluoro-benzaldehyde oxime

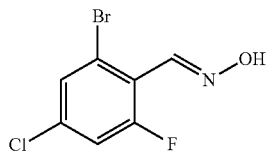 [SMILES: O/N=C/c1c(F)cc(Cl)cc1Br]

To a solution of 2-bromo-4-chloro-6-fluoro-benzaldehyde (15 g, 63.16 mmol) in 2-propanol (130 ml) was added hydroxylamine (50% solution in water, 4.55 g, 68.90 mmol) at 25° C. and the mixture was warmed to 40° C. for 2 h. Water (55 ml) was then added slowly to this mixture and the slurry was aged for 1 h at 20° C. The reaction mixture was filtered and the remaining solid was washed with a mixture of 2-propanol and water (1.5:1) and dried under vacuum to yield the title compound (12.5 g, 77%) as white solid.

[C]
2-Bromo-4-chloro-6-fluoro-N-hydroxy-benzamidine

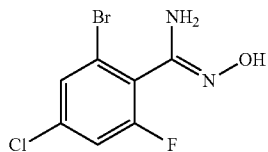 [SMILES: N/C(=N\O)c1c(F)cc(Cl)cc1Br]

A solution of N-chlorosuccinimide (8.34 g, 62.49 mmol) in DMF (25 ml) was added slowly to a solution of 2-bromo-4-chloro-6-fluoro-benzaldehyde oxime (15 g, 59.52 mmol) in DMF (50 ml) at 50° C. After completion of the addition, the reaction mixture was allowed to stir for 30 minutes at 50° C. It was then cooled to 3-5° C. and $NH_4OH$ (4.6 ml, 119 mmol) was added dropwise. During addition the temperature was maintained between 0-10° C. and the reaction mixture was stirred for another 15 minutes at the same temperature. EtOAc and brine were then added and the mixture was agitated vigorously for 10 minutes before the phases were allowed to settle. The aqueous layer was separated and extracted two times with EtOAc. The combined organic layers were dried with $Na_2SO_4$ and evaporated to obtain the title compound (13 g, 82%) as off white solid.

[D] 3-(2-Bromo-4-chloro-6-fluoro-phenyl)-5-methyl-[1,2,4]oxadiazole

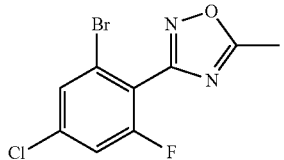

To a solution of 2-bromo-4-chloro-6-fluoro-N-hydroxy-benzamidine (26.5 g, 99.25 mmol) in 2-propanol (200 ml) was added N,N-dimethylacetamide dimethyl acetal (35.2 ml, 238.20 mmol) slowly at 25° C. and the reaction mixture was stirred for 30 minutes. After completion of the reaction all volatiles were evaporated and the resulting crude product was purified by chromatography (silica gel; hexane/EtOAc 97:3) to obtain the title compound (27.5 g, 58%) as white solid. MS: 290 (M+, 1Br).

Intermediate B-3

5-(2-Bromo-4-chloro-6-fluoro-phenyl)-2-methyl-2H-tetrazole

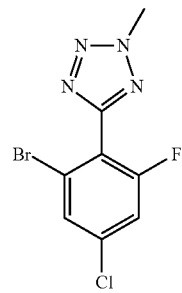

[A] 2-Bromo-4-chloro-6-fluoro-benzonitrile

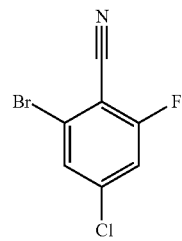

To a solution of 2-bromo-4-chloro-6-fluoro-phenylamine (10 g, 44.5 mmol) in anhydrous $CH_2Cl_2$ (100 ml) was added nitrosonium tetrafluoroborate (5.72 g, 49.01 mmol) and the mixture was stirred at 25° C. for 1 h. The reaction mixture was then cooled to 0° C. prior to addition of KCN (5.8 g, 89.1 mmol) followed by a dropwise addition of an aqueous solution (50 ml) of cupric sulfate hexahydrate (22.24 g, 89.1 mmol). After stirring for 40 minutes at 0° C., the reaction mixture was allowed to warm to 25° C. and stirring was continued for 1 h. The reaction mixture was diluted with CH$_2$Cl$_2$ (100 ml) and slowly quenched by the addition of aqueous saturated solution of NaHCO$_3$ until gas evolution was no longer observed. The resulting heterogeneous mixture was then filtered through a pad of celite and the organic layer was separated, washed twice with brine, dried with Na$_2$SO$_4$ and evaporated. The crude residue thus obtained was purified by chromatography (silica gel; hexane/EtOAc 90:10) to obtain the title compound (4 g, 38%) as reddish solid.

[B] 5-(2-Bromo-4-chloro-6-fluoro-phenyl)-2H-tetrazole

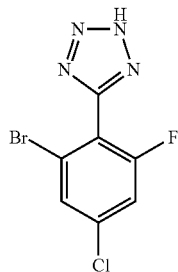

A mixture of 2-bromo-4-chloro-6-fluoro-benzonitrile (4 g, 17.06 mmol) and azidotrimethyltin (3.86 g, 18.77 mmol) in toluene (100 ml) was heated to 120° C. for 72 h. After completion of the reaction, the mixture was partitioned between EtOAc (50 ml) and aqueous 0.5N HCl solution (40 ml). The organic layer was separated, washed with water and brine, dried with Na$_2$SO$_4$ and concentrated under reduced pressure to afford the title compound (4.2 g, 87%) as red solid.

[C] 5-(2-Bromo-4-chloro-6-fluoro-phenyl)-2-methyl-2H-tetrazole

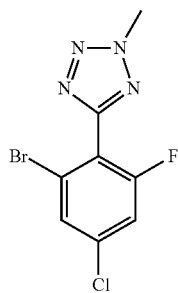

A mixture of 5-(2-bromo-4-chloro-6-fluoro-phenyl)-2H-tetrazole (4.15 g, 14.95 mmol), K$_2$CO$_3$ (3.1 g, 22.43 mmol) and iodomethane (1.3 ml, 20.94 mmol) in DMF (30 ml) was stirred at 25° C. for 3 h. The mixture was partitioned between EtOAc (80 ml) and water (60 ml), the organic layer was separated, washed with water and brine, dried with Na$_2$SO$_4$ and concentrated. The remaining residue was purified by chromatography (silica gel; hexane/EtOAc 100:0-90:10) to obtain 5-(2-bromo-4-chloro-6-fluoro-phenyl)-1-methyl-1H-tetrazole as pale yellow solid (1.5 g, 35%) and the title compound (1.7 g, 39%) as reddish liquid. MS: 291.0 (MH$^+$, 1Br).

Example 1

(rac)-2-(1-{[1-(2,2,2-Trifluoro-acetylamino)-cyclopropanecarbonyl]-amino}-indan-5-yl)-benzoic acid methyl ester

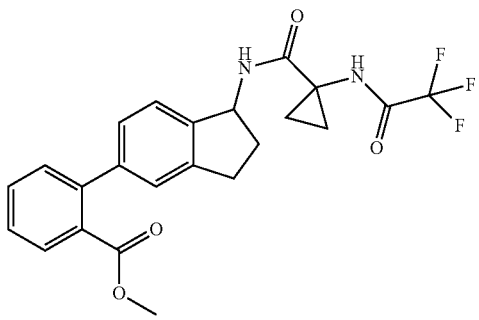 [SMILES: COC(=O)c1ccccc1-c1ccc2c(c1)CCC2NC(=O)C1(NC(=O)C(F)(F)F)CC1]

1-(2,2,2-Trifluoro-acetylamino)-cyclopropanecarboxylic acid ((rac)-5-bromo-indan-1-yl)-amide (intermediate A-1 [B]) (0.20 g, 511 μmol) and 2-(methoxycarbonyl)phenylboronic acid (184 mg, 1.02 mmol) were dissolved in dioxane (9.0 ml); then, sodium carbonate (163 mg, 1.53 mmol), dissolved in water, was added while stirring. Subsequently, (1,1'-bis-diphenylphosphino)-ferrocene)palladium-(II)dichloride (1:1 complex with CH$_2$Cl$_2$) (18.7 mg, 25.6 μmol, eq: 0.05) was added and the reaction mixture was heated up to 50° C. for 5 hours. It was then poured into H$_2$O (50 ml) and extracted with EtOAc (2×25 mL). The organic layers were dried over MgSO$_4$, filtered and concentrated in vacuo to give a crude product (0.296 g) which was purified by flash chromatography (silica gel, 20 g, 0% to 2% MeOH in CH$_2$Cl$_2$) to yield the title compound (0.21 g, 91%) as light brown oil. MS: 445.1 (M−H$^-$).

Example 2

1-(2,2,2-Trifluoro-acetylamino)-cyclopropanecarboxylic acid (rac)-{5-[3,5-dichloro-2-(2,2-difluoro-ethoxy)-phenyl]-indan-1-yl}-amide

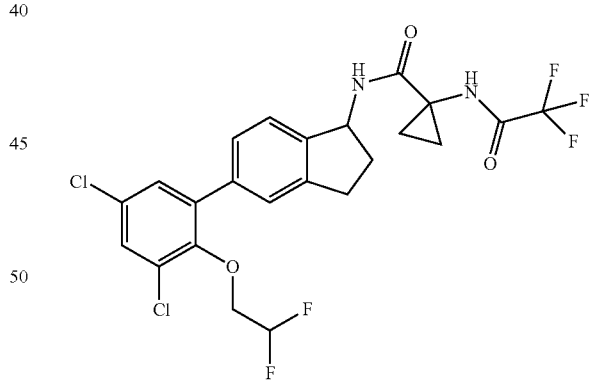

1-(2,2,2-Trifluoro-acetylamino)-cyclopropanecarboxylic acid[(rac)-5-(4,4,5,5-tetramethyl-[1,3,2]dioxaborolan-2-yl)-indan-1-yl]-amide (intermediate A-1) (0.22 g, 502 μmol), 1-bromo-3,5-dichloro-2-(2,2-difluoro-ethoxy)-benzene (intermediate B-1) (169 mg, 552 μmol) and tri-o-tolylphosphine (30.6 mg, 100 μmol, eq: 0.2) were dissolved in THF (10.0 ml); then palladium(II)acetate (5.64 mg, 25.1 μmol, eq: 0.05) was added, followed by potassium carbonate (173 mg, 1.25 mmol), dissolved in water (1.0 ml). The reaction mixture was stirred at RT over night, then poured into H$_2$O (50 ml) and extracted with EtOAc (2×25 mL). The organic layers were dried over MgSO$_4$, filtered and concentrated in vacuo to give a crude product (0.377 g) which was purified by flash chromatography (silica gel, 20 g, 10% to 50% EtOAc in heptane) to yield the title compound (0.15 g, 56%) as light yellow amorphous solid. MS: 535.1 (M−H⁻, 2Cl).

Example 3

(rac)-2-Chloro-6-(1-{[1-(2,2,2-trifluoro-acetylamino)-cyclopropanecarbonyl]-amino}-indan-5-yl)-benzoic acid methyl ester

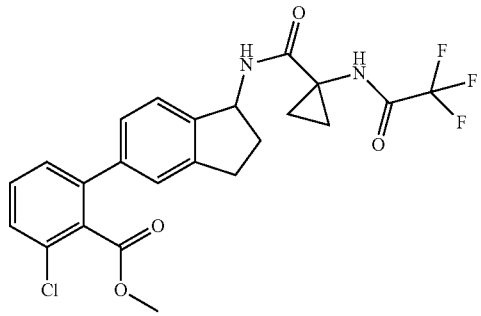 [SMILES: COC(=O)c1c(Cl)cccc1-c1ccc2c(c1)CCC2NC(=O)C1(NC(=O)C(F)(F)F)CC1]

In analogy to the procedure described for the preparation of example 2,1-(2,2,2-trifluoro-acetylamino)-cyclopropanecarboxylic acid[(rac)-5-(4,4,5,5-tetramethyl-[1,3,2]dioxaborolan-2-yl)-indan-1-yl]-amide (intermediate A-1) was reacted with 2-bromo-6-chloro-benzoic acid methyl ester to give the title compound as light yellow solid. MS: 479.1 (M−H⁻, 1Cl).

Example 4

1-(2,2,2-Trifluoro-acetylamino)-cyclopropanecarboxylic acid (rac)-{5-[5-chloro-3-fluoro-2-(5-methyl-[1,2,4]oxadiazol-3-yl)-phenyl]-indan-1-yl}-amide

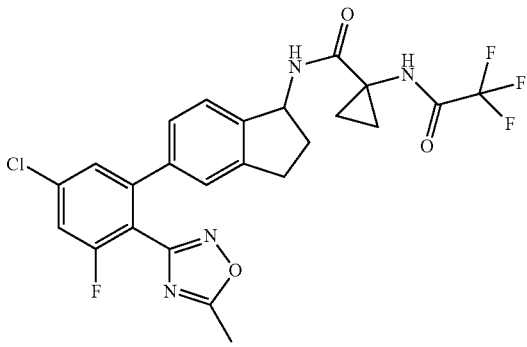

In analogy to the procedure described for the preparation of example 2,1-(2,2,2-trifluoro-acetylamino)-cyclopropanecarboxylic acid[(rac)-5-(4,4,5,5-tetramethyl-[1,3,2]dioxaborolan-2-yl)-indan-1-yl]-amide (intermediate A-1) was reacted with 3-(2-bromo-4-chloro-6-fluoro-phenyl)-5-methyl-[1,2,4]oxadiazole (intermediate B-2) to give the title compound as light yellow amorphous solid. MS: 521.1 (M−H⁻, 1Cl).

Example 5

1-(2,2,2-Trifluoro-acetylamino)-cyclopropanecarboxylic acid{(S)-5-[5-chloro-3-fluoro-2-(5-methyl-[1,2,4]oxadiazol-3-yl)-phenyl]-indan-1-yl}-amide

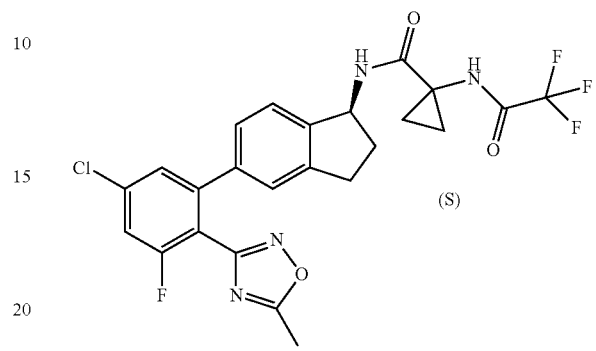

1-(2,2,2-Trifluoro-acetylamino)-cyclopropanecarboxylic acid[(S)-5-(4,4,5,5-tetramethyl-[1,3,2]dioxaborolan-2-yl)-indan-1-yl]-amide (intermediate A-2) (0.145 g, 331 µmol) and 3-(2-bromo-4-chloro-6-fluoro-phenyl)-5-methyl-[1,2,4]oxadiazole (intermediate B-2) (106 mg, 364 µmol) were dissolved in DMSO (5.00 ml), then sodium carbonate (87.7 mg, 827 µmol), dissolved in water (0.63 ml) was added, followed by (1,1'-bis-diphenylphosphino)-ferrocene)palladium-(II) dichloride (1:1 complex with CH₂Cl₂) (12.1 mg, 16.5 µmol, eq: 0.05). This mixture was heated up to 80° C. for 2 hours, then poured into H₂O (50 ml) and extracted with CH₂Cl₂ (2×25 mL). The organic layers were dried over MgSO₄, filtered and concentrated in vacuo to give a crude product (0.213 g) which was purified by flash chromatography (silica gel, 20 g, 10% to 50% EtOAc in heptane) to yield the title compound (0.094 g, 54%) as light yellow solid. MS: 523.1 (MH⁺, 1Cl).

Example 6

2-Chloro-6-((S)-1-{[3-(2,2,2-trifluoro-acetylamino)-oxetane-3-carbonyl]-amino}-indan-5-yl)-benzoic acid methyl ester

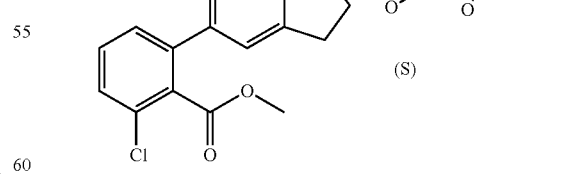

In analogy to the procedures described in example 5,3-(2,2,2-trifluoro-acetylamino)-oxetane-3-carboxylic acid[(S)-5-(4,4,5,5-tetramethyl-[1,3,2]dioxaborolan-2-yl)-indan-1-yl]-amide (intermediate A-3) was reacted with 2-bromo-6-chloro-benzoic acid methyl ester in the presence of (1,1'-bis-diphenylphosphino)-ferrocene)palladium-(II)dichloride (1:1 complex with CH$_2$Cl$_2$) to give the title compound as light yellow solid. MS: 514.1 (M+NH$_4^+$, 1Cl).

Example 7

3-(2,2,2-Trifluoro-acetylamino)-oxetane-3-carboxylic acid{(S)-5-[5-chloro-3-fluoro-2-(5-methyl-[1,2,4]oxadiazol-3-yl)-phenyl]-indan-1-yl}-amide

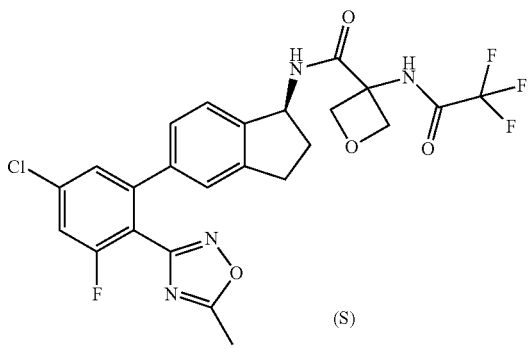 [SMILES: Cc1nc(-c2c(F)cc(Cl)cc2-c2ccc3c(c2)CC[C@@H]3NC(=O)C2(NC(=O)C(F)(F)F)COC2)no1 ; "(S)"]

In analogy to the procedures described in example 5,3-(2,2,2-trifluoro-acetylamino)-oxetane-3-carboxylic acid[(S)-5-(4,4,5,5-tetramethyl-[1,3,2]dioxaborolan-2-yl)-indan-1-yl]-amide (intermediate A-3) was reacted with 3-(2-bromo-4-chloro-6-fluoro-phenyl)-5-methyl-[1,2,4]oxadiazole (intermediate B-2) in the presence of (1,1'-bis-diphenylphosphino)-ferrocene)palladium-(II)dichloride (1:1 complex with CH$_2$Cl$_2$) to give the title compound as light yellow solid. MS: 537.1 (M−H$^-$, 1Cl).

Example 8

3-(2,2,2-Trifluoro-acetylamino)-oxetane-3-carboxylic acid{(S)-5-[5-chloro-3-fluoro-2-(2-methyl-2H-tetrazol-5-yl)-phenyl]-indan-1-yl}-amide

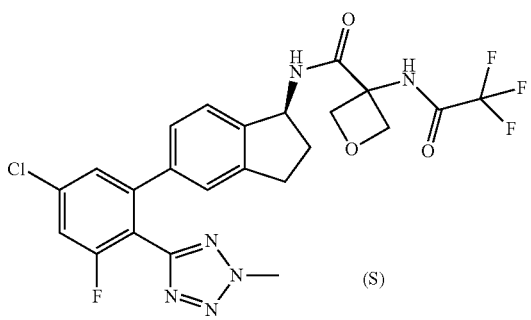 [SMILES: Cn1nnc(-c2c(F)cc(Cl)cc2-c2ccc3c(c2)CC[C@@H]3NC(=O)C2(NC(=O)C(F)(F)F)COC2)n1 ; "(S)"]

In analogy to the procedures described in example 5,3-(2,2,2-trifluoro-acetylamino)-oxetane-3-carboxylic acid[(S)-5-(4,4,5,5-tetramethyl-[1,3,2]dioxaborolan-2-yl)-indan-1-yl]-amide (intermediate A-3) was reacted with 5-(2-bromo-4-chloro-6-fluoro-phenyl)-2-methyl-2H-tetrazole (intermediate B-3) in the presence of (1,1'-bis-diphenylphosphino)-ferrocene)palladium-(II)dichloride (1:1 complex with CH$_2$Cl$_2$) to give the title compound as light brown solid. MS: 539.1 (MH$^+$, 1Cl).

Example 9

1-(2,2,2-Trifluoro-acetylamino)-cyclopropanecarboxylic acid{(rac)-6-[3,5-dichloro-2-(2,2-difluoro-ethoxy)-phenyl]-1,2,3,4-tetrahydro-naphthalen-1-yl}-amide

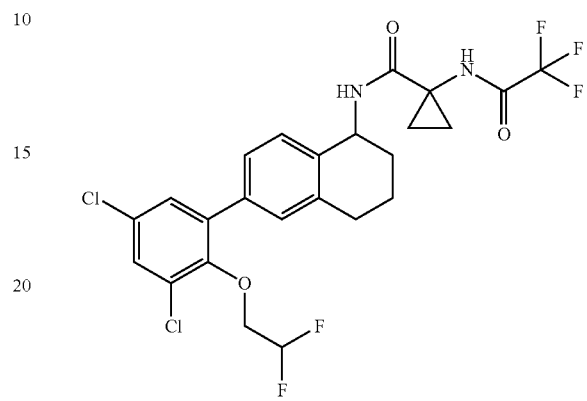

In analogy to the procedure described in example 5,1-(2,2,2-trifluoro-acetylamino)-cyclopropanecarboxylic acid [(rac)-6-(4,4,5,5-tetramethyl-[1,3,2]dioxaborolan-2-yl)-1,2,3,4-tetrahydro-naphthalen-1-yl]-amide (intermediate A-4) was reacted 1-bromo-3,5-dichloro-2-(2,2-difluoro-ethoxy)-benzene (intermediate B-1) and (1,1'-bis-diphenylphosphino)-ferrocene)palladium-(II)dichloride (1:1 complex with CH$_2$Cl$_2$) to give the title compound as light brown amorphous solid. MS: 549.1 (M−H$^-$, 2Cl).

Example 10

(rac)-2-Chloro-6-(5-{[1-(2,2,2-trifluoro-acetylamino)-cyclopropanecarbonyl]-amino}-5,6,7,8-tetrahydro-naphthalen-2-yl)-benzoic acid methyl ester

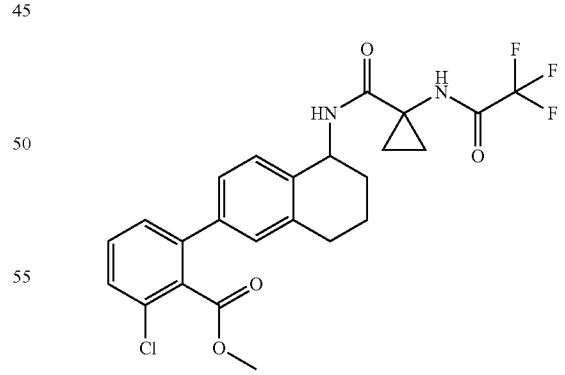

In analogy to the procedure described in example 5,1-(2,2,2-trifluoro-acetylamino)-cyclopropanecarboxylic acid [(rac)-6-(4,4,5,5-tetramethyl-[1,3,2]dioxaborolan-2-yl)-1,2,3,4-tetrahydro-naphthalen-1-yl]-amide (intermediate A-4) was reacted with 2-bromo-6-chloro-benzoic acid methyl ester to give the title compound as off-white solid. MS: 512.2 (M+NH$_4^+$, 1Cl).

Example 11

1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-1,2,3,4-tetrahydro-naphthalen-1-yl}-amide

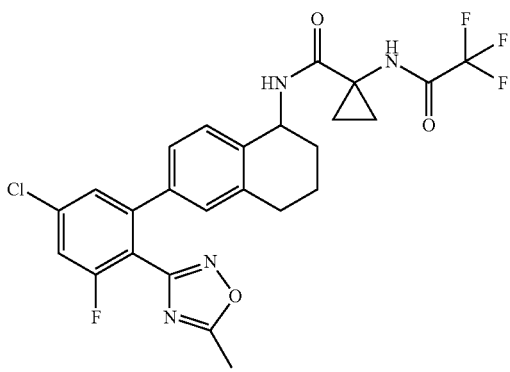 [SMILES: Cc1nc(-c2c(F)cc(Cl)cc2-c2ccc3c(c2)CCCC3NC(=O)C2(NC(=O)C(F)(F)F)CC2)no1]

In analogy to the procedure described in example 5, 1-(2,2,2-trifluoro-acetylamino)-cyclopropanecarboxylic acid [(rac)-6-(4,4,5,5-tetramethyl-[1,3,2]dioxaborolan-2-yl)-1,2,3,4-tetrahydro-naphthalen-1-yl]-amide (intermediate A-4) was reacted with 3-(2-bromo-4-chloro-6-fluoro-phenyl)-5-methyl-[1,2,4]oxadiazole (intermediate B-2) to give the title compound as light yellow solid. MS: 537.1 (MH$^+$, 1Cl).

Example 12

1-(2,2,2-Trifluoro-acetylamino)-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide

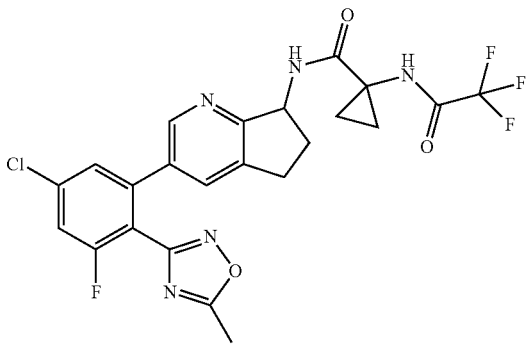 [SMILES: Cc1nc(-c2c(F)cc(Cl)cc2-c2cnc3c(c2)CCC3NC(=O)C2(NC(=O)C(F)(F)F)CC2)no1]

1-(2,2,2-trifluoro-acetylamino)-cyclopropanecarboxylic acid ((rac)-3-bromo-6,7-dihydro-5H-[1]pyrindin-7-yl)-amide (intermediate A-5) (0.2 g, 510 µmol), potassium acetate (150 mg, 1.53 mmol) and 4,4,4',4',5,5,5',5'-octamethyl-2,2'-bi(1,3,2-dioxaborolane) (155 mg, 612 µmol) were dissolved in DMSO (8.0 ml). The reaction vessel was closed and evacuated, then charged with argon; this procedure was repeated five times. After 10 minutes (1,1'-bis-diphenylphosphino)-ferrocene)palladium-(II)dichloride (1:1 complex with CH$_2$Cl$_2$) (18.7 mg, 25.5 µmol, eq: 0.05) was added and the reaction mixture was stirred at 90° C. for 1.5 hours. After cooling to RT, potassium carbonate (141 mg, 1.02 mmol), dissolved in water (1.0 ml) and 3-(2-bromo-4-chloro-6-fluoro-phenyl)-5-methyl-[1,2,4]oxadiazole (intermediate B-2) (164 mg, 561 µmol) were added, followed by (1,1'-bis-diphenylphosphino)-ferrocene)palladium-(II)dichloride (1:1 complex with CH$_2$Cl$_2$) (18.7 mg, 25.5 µmol, eq: 0.05). This reaction mixture was stirred at 80° C. for 3 hours, then poured into H$_2$O (50 ml) and extracted with CH$_2$Cl$_2$ (3×25 ml). The organic layers were dried over MgSO$_4$, filtered and concentrated in vacuo to give a crude product (0.364 g), which was purified by flash chromatography (silica gel, 20 g, 0% to 2% MeOH in CH$_2$Cl$_2$) to yield the title compound (0.134 g, 50%) as light grey solid. MS: 524.1 (MH$^+$, 1Cl).

Example 13

1-(2,2,2-Trifluoro-acetylamino)-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide

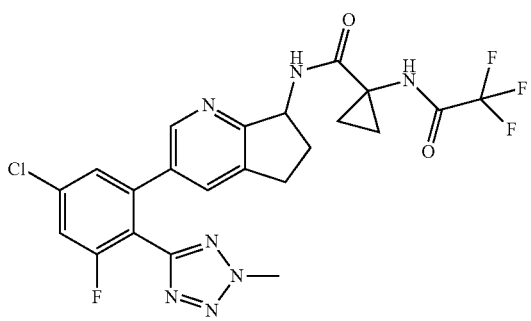 [SMILES: Cn1nnc(-c2c(F)cc(Cl)cc2-c2cnc3c(c2)CCC3NC(=O)C2(NC(=O)C(F)(F)F)CC2)n1]

In analogy to the procedure described in example 12, 1-(2,2,2-trifluoro-acetylamino)-cyclopropanecarboxylic acid ((rac)-3-bromo-6,7-dihydro-5H-[1]pyrindin-7-yl)-amide (intermediate A-5) was reacted with 4,4,4',4',5,5,5',5'-octamethyl-2,2'-bi(1,3,2-dioxaborolane), (1,1'-bis-diphenylphosphino)-ferrocene)palladium-(II)dichloride (1:1 complex with CH$_2$Cl$_2$) and subsequently with 5-(2-bromo-4-chloro-6-fluoro-phenyl)-2-methyl-2H-tetrazole (intermediate B-3) to give the title compound as off-white solid. MS: 524.2 (MH$^+$, 1Cl).

Example 14

1-(2,2,2-Trifluoro-acetylamino)-cyclopropanecarboxylic acid{(rac)-7-[5-chloro-3-fluoro-2-(5-methyl-[1,2,4]oxadiazol-3-yl)-phenyl]-chroman-4-yl}-amide

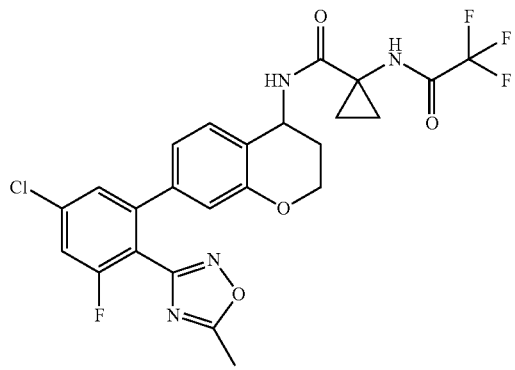 [SMILES: Cc1nc(-c2c(F)cc(Cl)cc2-c2ccc3c(c2)OCCC3NC(=O)C2(NC(=O)C(F)(F)F)CC2)no1]

In analogy to the procedure described in example 5,1-(2, 2,2-trifluoro-acetylamino)-cyclopropanecarboxylic acid [(rac)-7-(4,4,5,5-tetramethyl-[1,3,2]dioxaborolan-2-yl)-chroman-4-yl]-amide (intermediate A-6) was reacted with 3-(2-bromo-4-chloro-6-fluoro-phenyl)-5-methyl-[1,2,4] oxadiazole (intermediate B-2) to give the title compound as light yellow solid. MS: 539.1 (MH+, 1Cl).

Example 15

1-(2,2,2-Trifluoro-acetylamino)-cyclopropanecarboxylic acid{(rac)-7-[5-chloro-3-fluoro-2-(2-methyl-2H-tetrazol-5-yl)-phenyl]-chroman-4-yl}-amide

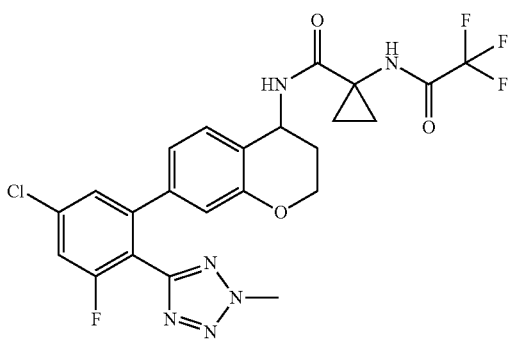 [SMILES: Cn1nnc(-c2c(F)cc(Cl)cc2-c2ccc3c(c2)OCCC3NC(=O)C2(NC(=O)C(F)(F)F)CC2)n1]

In analogy to the procedure described in example 5,1-(2, 2,2-trifluoro-acetylamino)-cyclopropanecarboxylic acid [(rac)-7-(4,4,5,5-tetramethyl-[1,3,2]dioxaborolan-2-yl)-chroman-4-yl]-amide (intermediate A-6) was reacted with 5-(2-bromo-4-chloro-6-fluoro-phenyl)-2-methyl-2H-tetrazole (intermediate B-3) to give the title compound as light yellow solid. MS: 539.1 (MH+, 1Cl).

Example 16

1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide

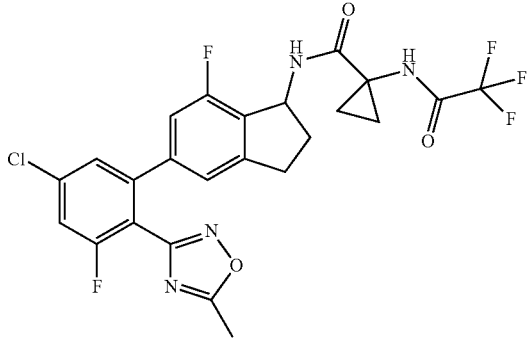 [SMILES: Cc1nc(-c2c(F)cc(Cl)cc2-c2cc(F)c3c(c2)CCC3NC(=O)C2(NC(=O)C(F)(F)F)CC2)no1]

In analogy to the procedure described in example 5,1-(2, 2,2-trifluoro-acetylamino)-cyclopropanecarboxylic acid [(rac)-7-fluoro-5-(4,4,5,5-tetramethyl-[1,3,2]dioxaborolan-2-yl)-indan-1-yl]-amide (intermediate A-7) was reacted with 3-(2-bromo-4-chloro-6-fluoro-phenyl)-5-methyl-[1,2,4] oxadiazole (intermediate B-2) to give the title compound as light yellow amorphous solid. MS: 541.1 (MH+, 1Cl).

Example 17

1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-1-methyl-indan-1-yl}-amide

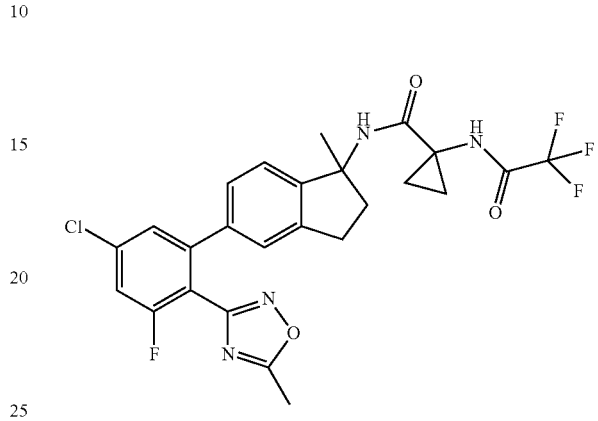

In analogy to the procedure described in example 12, 1-(2, 2,2-trifluoro-acetylamino)-cyclopropanecarboxylic acid ((rac)-5-bromo-1-methyl-indan-1-yl)-amide (intermediate A-10) was reacted with 4,4,4',4',5,5,5',5'-octamethyl-2,2'-bi (1,3,2-dioxaborolane), (1,1'-bis-diphenylphosphino)-ferrocene)palladium-(II)dichloride (1:1 complex with CH2Cl2) and subsequently with 3-(2-bromo-4-chloro-6-fluoro-phenyl)-5-methyl-[1,2,4]oxadiazole (intermediate B-2) to give the title compound as colorless amorphous solid. MS: 535.1 (M−H−, 1Cl).

Example 18

1-(2,2,2-Trifluoro-acetylamino)-cyclopropanecarboxylic acid{(rac)-5-[5-chloro-3-fluoro-2-(2-methyl-2H-tetrazol-5-yl)-phenyl]-1-methyl-indan-1-yl}-amide

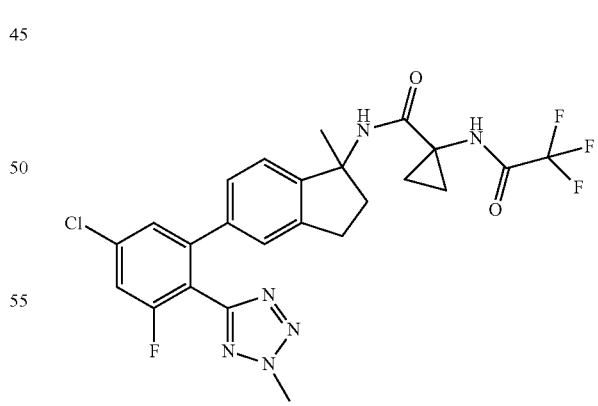

In analogy to the procedure described in example 12, 1-(2, 2,2-trifluoro-acetylamino)-cyclopropanecarboxylic acid ((rac)-5-bromo-1-methyl-indan-1-yl)-amide (intermediate A-10) was reacted with 4,4,4',4',5,5,5',5'-octamethyl-2,2'-bi (1,3,2-dioxaborolane), (1,1'-bis-diphenylphosphino)-ferrocene)palladium-(II)dichloride (1:1 complex with CH2Cl2) and subsequently with 5-(2-bromo-4-chloro-6-fluoro-phenyl)-2-methyl-2H-tetrazole (intermediate B-3) to give the title compound as colorless amorphous solid. MS: 534.8 (M−H⁻, 1Cl).

Example 19

1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide

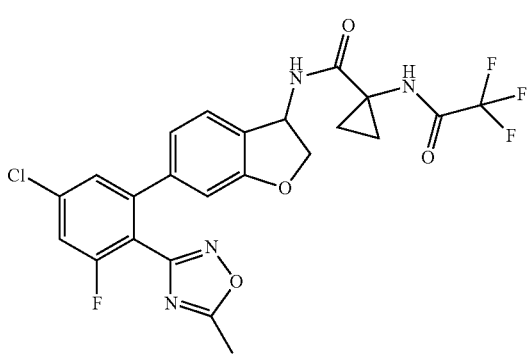 [SMILES: Cc1nc(-c2c(F)cc(Cl)cc2-c2ccc3c(c2)OCC3NC(=O)C2(NC(=O)C(F)(F)F)CC2)no1]

In analogy to the procedure described in example 5,1-(2,2,2-trifluoro-acetylamino)-cyclopropanecarboxylic acid [(rac)-6-(4,4,5,5-tetramethyl-[1,3,2]dioxaborolan-2-yl)-2,3-dihydro-benzofuran-3-yl]-amide (intermediate A-8) was reacted with 3-(2-bromo-4-chloro-6-fluoro-phenyl)-5-methyl-[1,2,4]oxadiazole (intermediate B-2) to give the title compound as light yellow solid. MS: 525.1 (MH⁺, 1Cl).

Example 20

1-(2,2,2-Trifluoro-acetylamino)-cyclopropanecarboxylic acid{(rac)-6-[5-chloro-3-fluoro-2-(2-methyl-2H-tetrazol-5-yl)-phenyl]-2,3-dihydro-benzofuran-3-yl}-amide

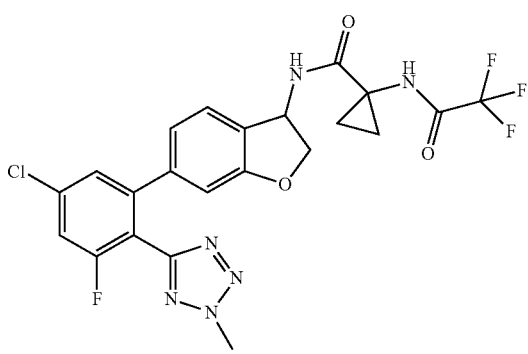 [SMILES: Cn1nnc(-c2c(F)cc(Cl)cc2-c2ccc3c(c2)OCC3NC(=O)C2(NC(=O)C(F)(F)F)CC2)n1]

In analogy to the procedure described in example 5,1-(2,2,2-trifluoro-acetylamino)-cyclopropanecarboxylic acid [(rac)-6-(4,4,5,5-tetramethyl-[1,3,2]dioxaborolan-2-yl)-2,3-dihydro-benzofuran-3-yl]-amide (intermediate A-8) was reacted with 5-(2-bromo-4-chloro-6-fluoro-phenyl)-2-me-thyl-2H-tetrazole (intermediate B-3) to give the title compound as light yellow solid. MS: 525.1 (MH⁺, 1Cl).

Example 21

1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-2,3-dihydro-benzo[b]thiophen-3-yl}-amide

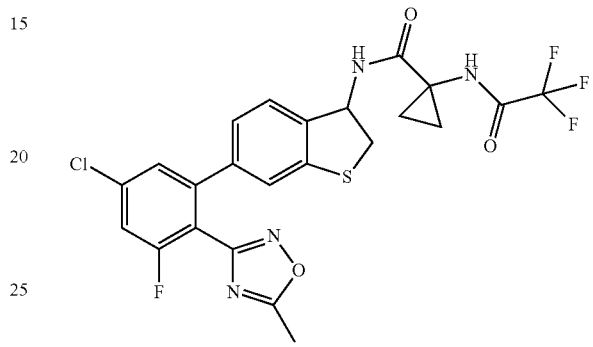

In analogy to the procedure described in example 5,1-(2,2,2-trifluoro-acetylamino)-cyclopropanecarboxylic acid [(rac)-6-(4,4,5,5-tetramethyl-[1,3,2]dioxaborolan-2-yl)-2,3-dihydro-benzo[b]thiophen-3-yl]-amide (intermediate A-9) was reacted with 3-(2-bromo-4-chloro-6-fluoro-phenyl)-5-methyl-[1,2,4]oxadiazole (intermediate B-2) to give the title compound as light yellow solid. MS: 541.1 (MH⁺, 1Cl).

Example 22

1-(2,2,2-Trifluoro-acetylamino)-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide

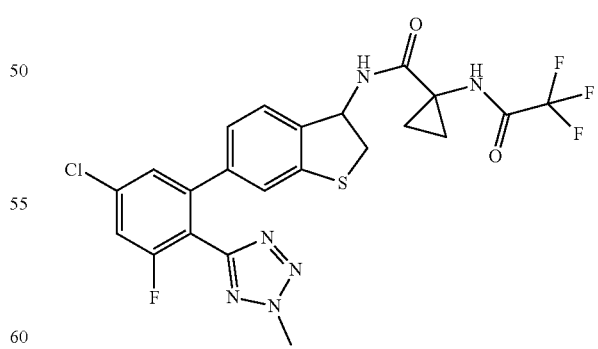

In analogy to the procedure described in example 5,1-(2,2,2-trifluoro-acetylamino)-cyclopropanecarboxylic acid [(rac)-6-(4,4,5,5-tetramethyl-[1,3,2]dioxaborolan-2-yl)-2,3-dihydro-benzo[b]thiophen-3-yl]-amide (intermediate A-9) was reacted with 5-(2-bromo-4-chloro-6-fluoro-phenyl)-2- methyl-2H-tetrazole (intermediate B-3) to give the title compound as light yellow solid. MS: 541.1 (MH⁺, 1Cl).

Example 23

(1-{(S)-5-[5-Chloro-3-fluoro-2-(5-methyl-[1,2,4]oxadiazol-3-yl)-phenyl]-indan-1-ylcarbamoyl}-cyclopropyl)-carbamic acid tert-butyl ester

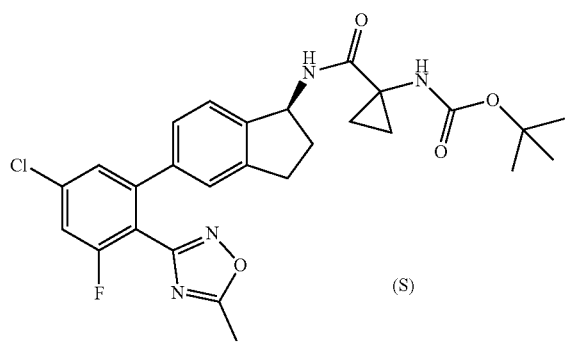 [SMILES: Cc1nc(-c2c(F)cc(Cl)cc2-c2ccc3c(c2)CC[C@@H]3NC(=O)C2(NC(=O)OC(C)(C)C)CC2)no1 ; "(S)"]

In analogy to the procedures described for the preparation of intermediate A-1 [B], (S)-5-[5-chloro-3-fluoro-2-(5-methyl-[1,2,4]oxadiazol-3-yl)-phenyl]-indan-1-ylamine (intermediate A-11) was coupled with 1-tert-butoxycarbonylamino-cyclopropanecarboxylic acid to yield the title compound as light yellow amorphous solid. MS: 527.2 (MH⁺, 1Cl).

Example 24

1-Amino-cyclopropanecarboxylic acid{(S)-5-[5-chloro-3-fluoro-2-(5-methyl-[1,2,4]oxadiazol-3-yl)-phenyl]-indan-1-yl}-amide

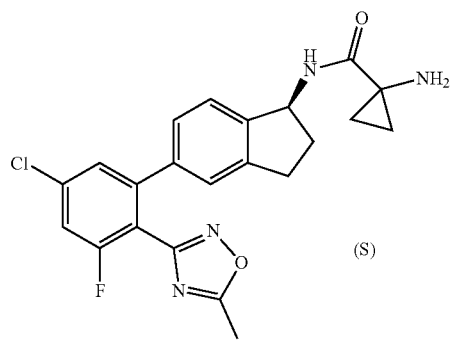 [SMILES: Cc1nc(-c2c(F)cc(Cl)cc2-c2ccc3c(c2)CC[C@@H]3NC(=O)C2(N)CC2)no1 ; "(S)"]

In analogy to the procedure described for the preparation of intermediate A-11 [C], (1-{(S)-5-[5-chloro-3-fluoro-2-(5-methyl-[1,2,4]oxadiazol-3-yl)-phenyl]-indan-1-ylcarbamoyl}-cyclopropyl)-carbamic acid tert-butyl ester (example 23) was treated with trifluoro-acetic acid (90%) in CH₂Cl₂ to yield the title compound light yellow amorphous solid. MS: 427.1 (MH⁺, 1Cl).

Example 25

Pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide

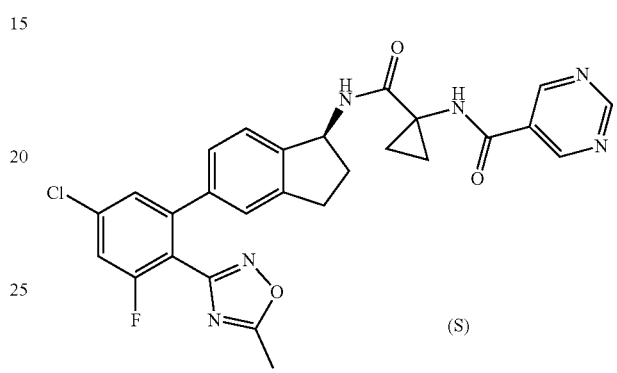

In analogy to the procedures described for the preparation of intermediate A-1 [B], 1-amino-cyclopropanecarboxylic acid{(S)-5-[5-chloro-3-fluoro-2-(5-methyl-[1,2,4]oxadiazol-3-yl)-phenyl]-indan-1-yl}-amide (example 24) was coupled with pyrimidine-5-carboxylic acid to yield the title compound as yellow solid. MS: 533.2 (MH⁺, 1Cl).

Example 26

2-Methoxy-pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide

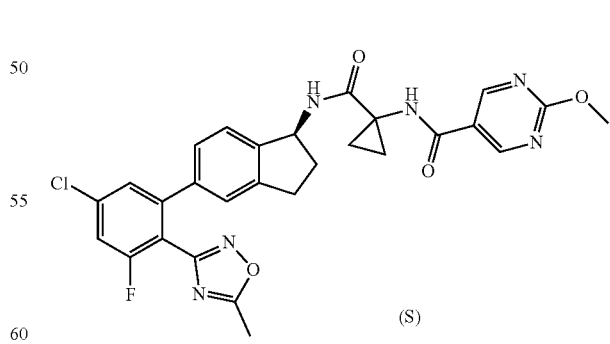

In analogy to the procedures described for the preparation of intermediate A-1 [B], 1-amino-cyclopropanecarboxylic acid{(S)-5-[5-chloro-3-fluoro-2-(5-methyl-[1,2,4]oxadiazol-3-yl)-phenyl]-indan-1-yl}-amide (example 24) was coupled with 2-methoxy-pyrimidine-5-carboxylic acid to yield the title compound as light yellow solid. MS: 563.2 (MH+, 1Cl).

Example 27

Pyridazine-4-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide

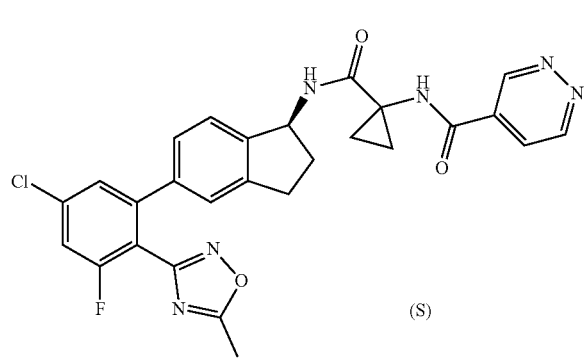 [SMILES: Cc1nc(-c2c(F)cc(Cl)cc2-c2ccc3c(c2)CC[C@@H]3NC(=O)C2(NC(=O)c3ccnnc3)CC2)no1 ; "(S)"]

In analogy to the procedures described for the preparation of intermediate A-1 [B], 1-amino-cyclopropanecarboxylic acid{(S)-5-[5-chloro-3-fluoro-2-(5-methyl-[1,2,4]oxadiazol-3-yl)-phenyl]-indan-1-yl}-amide (example 24) was coupled with pyridazine-4-carboxylic acid to yield the title compound as light yellow solid. MS: 533.2 (MH+, 1Cl).

Example 28

Isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide

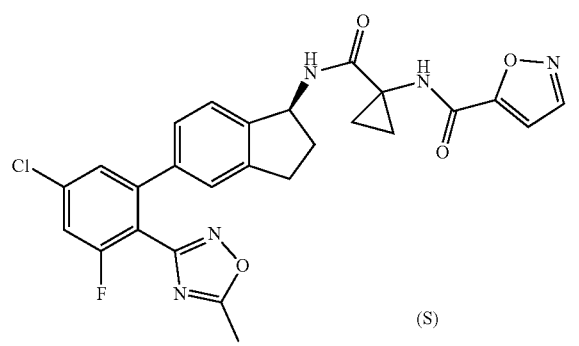 [SMILES: Cc1nc(-c2c(F)cc(Cl)cc2-c2ccc3c(c2)CC[C@@H]3NC(=O)C2(NC(=O)c3ccno3)CC2)no1 ; "(S)"]

In analogy to the procedures described for the preparation of intermediate A-1 [B], 1-amino-cyclopropanecarboxylic acid{(S)-5-[5-chloro-3-fluoro-2-(5-methyl-[1,2,4]oxadiazol-3-yl)-phenyl]-indan-1-yl}-amide (example 24) was coupled with isoxazole-5-carboxylic acid to yield the title compound as light yellow solid. MS: 522.1 (MH+, 1Cl).

Example 29

5-Methyl-[1,3,4]oxadiazole-2-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide

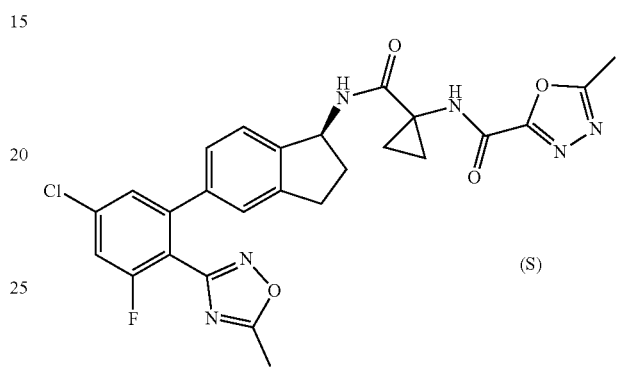

In analogy to the procedures described for the preparation of intermediate A-1 [B], 1-amino-cyclopropanecarboxylic acid{(S)-5-[5-chloro-3-fluoro-2-(5-methyl-[1,2,4]oxadiazol-3-yl)-phenyl]-indan-1-yl}-amide (example 24) was coupled with 5-methyl-[1,3,4]oxadiazole-2-carboxylic acid to yield the title compound as light yellow solid. MS: 534.2 (MH+, 1Cl).

Example 30

3-Methoxy-isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide In analogy to the procedures described for the preparation of intermediate A-1 [B], 1-amino-cyclopropanecarboxylic acid{(S)-5-[5-chloro-3-fluoro-2-(5-methyl-[1,2,4]oxadiazol-3-yl)-phenyl]-indan-1-yl}-amide (example 24) was coupled with 3-methoxy-isoxazole-5-carboxylic acid to yield the title compound as light yellow solid. MS: 552.2 (MH+, 1Cl).

Example 31

(1-{(rac)-5-[5-Chloro-3-fluoro-2-(5-methyl-[1,2,4] oxadiazol-3-yl)-phenyl]-7-fluoro-indan-1-ylcarbamoyl}-cyclopropyl)-carbamic acid tert-butyl ester

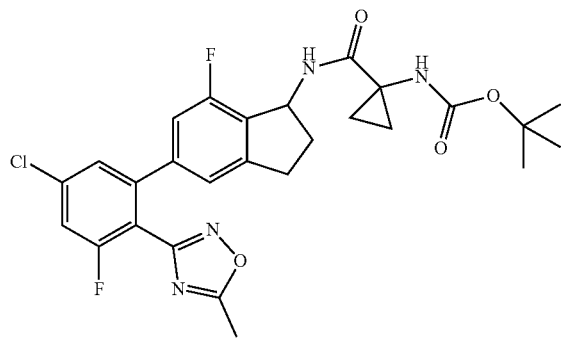 [SMILES: Cc1nc(-c2c(F)cc(Cl)cc2-c2cc(F)c3c(c2)CCC3NC(=O)C2(NC(=O)OC(C)(C)C)CC2)no1]

In analogy to the procedures described for the preparation of intermediate A-1 [B] and for the preparation of example 12, (rac)-5-bromo-7-fluoro-indan-1-ylamine (intermediate A-7 [C]) has been coupled with 1-tert-butoxycarbonylamino-cyclopropanecarboxylic acid to give [1-((rac)-5-bromo-7-fluoro-indan-1-ylcarbamoyl)-cyclopropyl]-carbamic acid tert-butyl ester, which was then reacted with 4,4,4',4',5,5,5',5'-octamethyl-2,2'-bi(1,3,2-dioxaborolane) and (1,1'-bis-diphenylphosphino)-ferrocene)palladium-(II)dichloride (1:1 complex with CH2Cl2) and subsequently with 3-(2-bromo-4-chloro-6-fluoro-phenyl)-5-methyl-[1,2,4]oxadiazole (intermediate B-2) to give the title compound as light brown solid. MS: 545.2 (MH+, 1Cl).

Example 32

1-Amino-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide

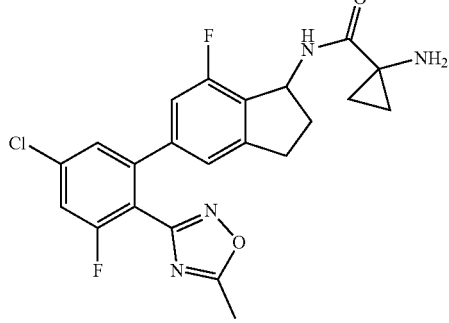

In analogy to the procedure described for the preparation of intermediate A-11 [C], (1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-carbamic acid tert-butyl ester (example 31) has been treated with trifluoroacetic acid (90%) to give the title compound as light brown oil. MS: 445.1 (MH+, 1Cl).

Example 33

2-Methoxy-pyrimidine-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide

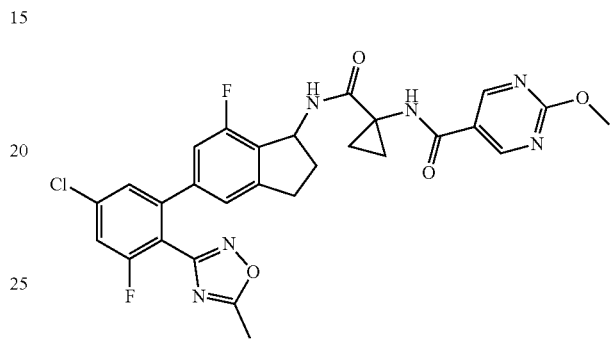

In analogy to the procedure described for the preparation of intermediate A-1 [B], 1-amino-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide (example 32) has been coupled with 2-methoxy-pyrimidine-5-carboxylic acid to yield the title compound as light yellow solid. MS: 581.2 (MH+, 1Cl).

Example 34

Pyridazine-4-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide

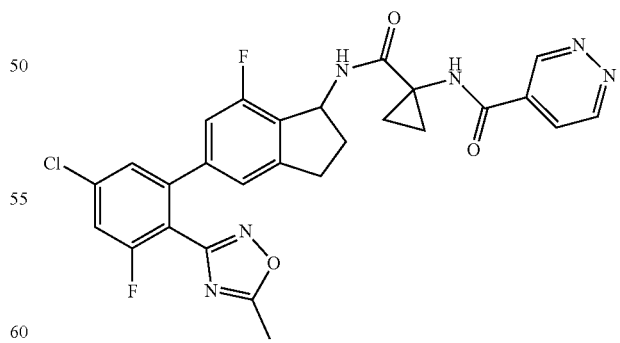

In analogy to the procedure described for the preparation of intermediate A-1 [B], 1-amino-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide (example 32)

has been coupled with pyridazine-4-carboxylic acid to yield the title compound as light yellow solid. MS: 551.1 (MH+, 1Cl).

Example 35

3-Methoxy-isoxazole-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide

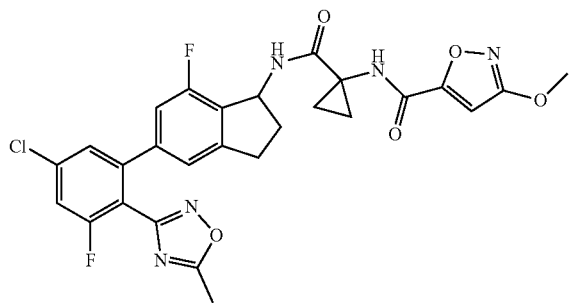 [SMILES: COc1cc(C(=O)NC2(C(=O)NC3CCc4cc(-c5cc(Cl)cc(F)c5-c5noc(C)n5)cc(F)c43)CC2)on1]

In analogy to the procedure described for the preparation of intermediate A-1 [B], 1-amino-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide (example 32) has been coupled with 3-methoxy-isoxazole-5-carboxylic acid to yield the title compound as light red oil. MS: 570.1 (MH+, 1Cl).

Example 36

(1-{(rac)-3-[5-Chloro-3-fluoro-2-(5-methyl-[1,2,4]oxadiazol-3-yl)-phenyl]-6,7-dihydro-5H-[1]pyrindin-7-ylcarbamoyl}-cyclopropyl)-carbamic acid tert-butyl ester

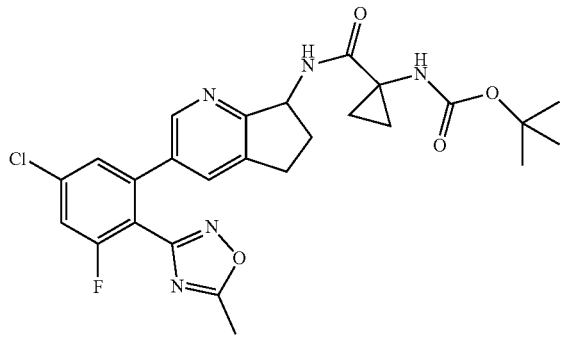 [SMILES: Cc1nc(-c2c(F)cc(Cl)cc2-c2cnc3c(c2)CCC3NC(=O)C2(NC(=O)OC(C)(C)C)CC2)no1]

In analogy to the procedures described for the preparation of intermediate A-11 [A], of example 12, of intermediate A-11 [C] and for the preparation of intermediate A-1 [B], the title compound has been prepared by the following reaction sequence: i) (rac)-3-bromo-6,7-dihydro-5H-[1]pyrindin-7-ylamine (intermediate A-5 [B]) was converted into ((rac)-3-bromo-6,7-dihydro-5H-[1]pyrindin-7-yl)-carbamic acid tert-butyl ester; ii) ((rac)-3-bromo-6,7-dihydro-5H-[1]pyrindin-7-yl)-carbamic acid tert-butyl ester has been reacted with 4,4,4',4',5,5,5',5'-octamethyl-2,2'-bi(1,3,2-dioxaborolane) and (1,1'-bis-diphenylphosphino)-ferrocene)palladium-(II) dichloride (1:1 complex with CH$_2$Cl$_2$) and subsequently with 3-(2-bromo-4-chloro-6-fluoro-phenyl)-5-methyl-[1,2,4]oxadiazole (intermediate B-2) to give {(rac)-3-[5-chloro-3-fluoro-2-(5-methyl-[1,2,4]oxadiazol-3-yl)-phenyl]-6,7-dihydro-5H-[1]pyrindin-7-yl}-carbamic acid tert-butyl ester; iii) removal of the BOC protective group to give (rac)-3-[5-chloro-3-fluoro-2-(5-methyl-[1,2,4]oxadiazol-3-yl)-phenyl]-6,7-dihydro-5H-[1]pyrindin-7-ylamine; iv) coupling with 1-tert-butoxycarbonylamino-cyclopropanecarboxylic acid to give the title compound as light red oil. MS: 528.2 (MH+, 1Cl).

Example 37

1-Amino-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide

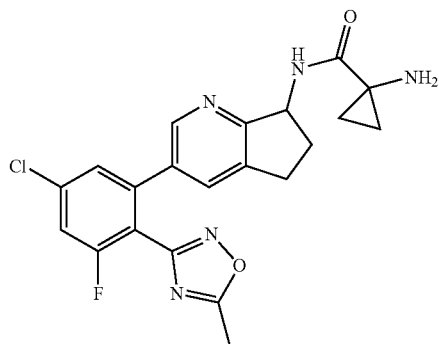 [SMILES: Cc1nc(-c2c(F)cc(Cl)cc2-c2cnc3c(c2)CCC3NC(=O)C2(N)CC2)no1]

In analogy to the procedure described for the preparation of intermediate A-11 [C], (1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-carbamic acid tert-butyl ester (example 36) has been treated with trifluoroacetic acid (90%) to give the title compound as light yellow oil. MS: 428.1 (MH+, 1Cl).

Example 38

3-Methoxy-isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide

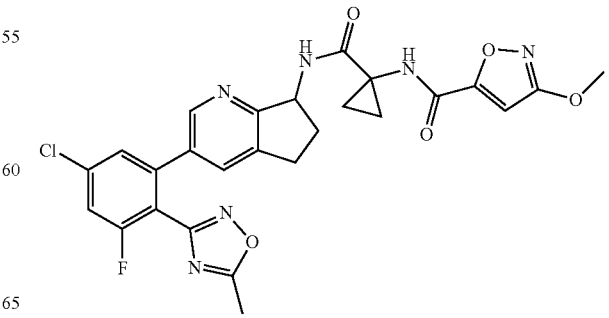

In analogy to the procedure described for the preparation of intermediate A-1 [B], 1-amino-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide (example 37) has been coupled with 3-methoxy-isoxazole-5-carboxylic acid to yield the title compound as light grey solid. MS: 553.1 (MH$^+$, 1Cl).

Example 39

Pyridazine-4-carboxylic acid(1-{(rac) 3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide

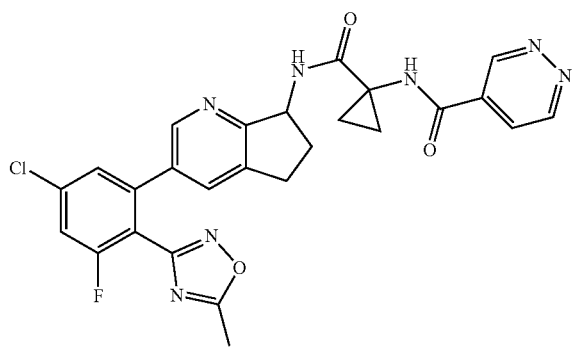 [SMILES: Cc1nc(-c2c(F)cc(Cl)cc2-c2cnc3c(c2)CCC3NC(=O)C2(NC(=O)c3ccnnc3)CC2)no1]

In analogy to the procedure described for the preparation of intermediate A-1 [B], 1-amino-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide (example 37) has been coupled with pyridazine-4-carboxylic acid to yield the title compound as light brown amorphous solid. MS: 534.1 (MH$^+$, 1Cl).

Example 40

Pyridazine-4-carboxylic acid(1-{(R or S) 3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide

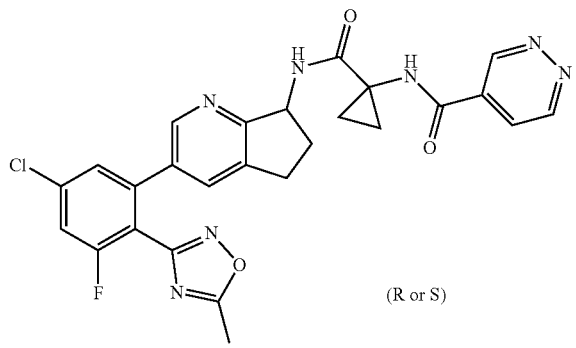 [SMILES: Cc1nc(-c2c(F)cc(Cl)cc2-c2cnc3c(c2)CCC3NC(=O)C2(NC(=O)c3ccnnc3)CC2)no1]

(R or S)

Pyridazine-4-carboxylic acid(1-{(rac) 3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide (example 39) (200 mg) has been separated into its antipodes by HPLC chromatography (Chiralpak AD HPLC column, 40% 2-propanol in heptane) to give the tile compound, $[\alpha]^D_{(20\ deg)}$=+7.52, (c=1.0 in CHCl$_3$) (81 mg) as colorless solid; and, see example 41.

Example 41

Pyridazine-4-carboxylic acid(1-{(S or R) 3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide

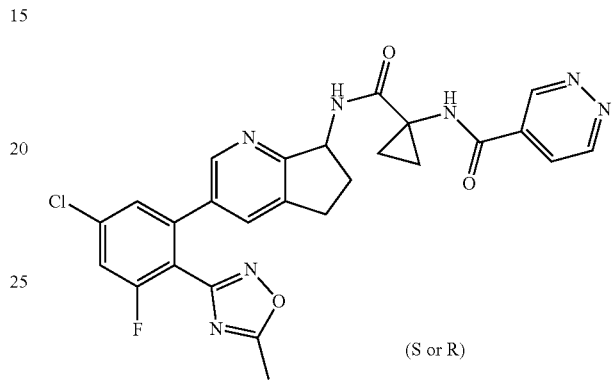

(S or R)

Pyridazine-4-carboxylic acid(1-{(rac) 3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide (example 39) (200 mg) has been separated into its antipodes by HPLC chromatography (Chiralpak AD HPLC column, 40% 2-propanol in heptane) to give the tile compound, $[\alpha]^D_{(20\ deg)}$=−7.50, (c=1.0 in CHCl$_3$) (85 mg) as off-white solid; and, see example 40.

Example 42

2-Methoxy-pyrimidine-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide

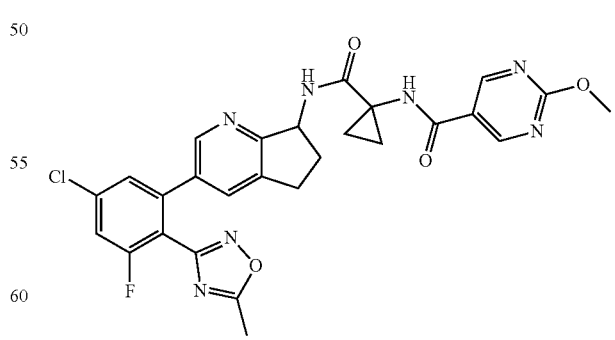

In analogy to the procedure described for the preparation of intermediate A-1 [B], 1-amino-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide (example 37) has been coupled with 2-methoxy-pyrimidine-5-carboxylic acid to yield the title compound as off-white solid. MS: 564.2 (MH+, 1Cl).

Example 43

Isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide

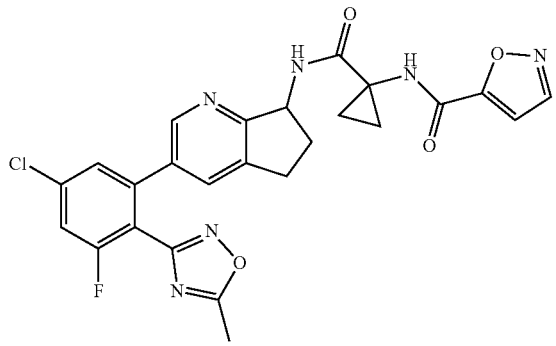 [SMILES: Cc1nc(-c2c(F)cc(Cl)cc2-c2cnc3c(c2)CCC3NC(=O)C2(NC(=O)c3ccno3)CC2)no1]

In analogy to the procedure described for the preparation of intermediate A-1 [B], 1-amino-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide (example 37) has been coupled with isoxazole-5-carboxylic acid to yield the title compound as off-white solid. MS: 523.1 (MH+, 1Cl).

Example 44

(1-{(rac)-6-[5-Chloro-3-fluoro-2-(5-methyl-[1,2,4]oxadiazol-3-yl)-phenyl]-2,3-dihydro-benzofuran-3-ylcarbamoyl}-cyclopropyl)-carbamic acid tert-butyl ester

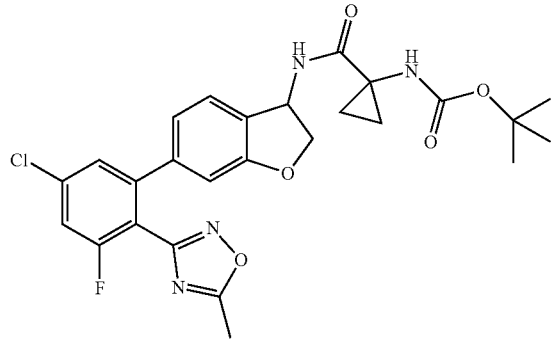 [SMILES: Cc1nc(-c2c(F)cc(Cl)cc2-c2ccc3c(c2)OCC3NC(=O)C2(NC(=O)OC(C)(C)C)CC2)no1]

In analogy to the procedures described for the preparation of intermediate A-1 [B] and for the preparation of example 12, (rac)-6-bromo-2,3-dihydro-benzofuran-3-ylamine (intermediate A-8 [B]) has been coupled with 1-tert-butoxycarbonylamino-cyclopropanecarboxylic acid to give [1-((rac)-6-bromo-2,3-dihydro-benzofuran-3-ylcarbamoyl)-cyclopropyl]-carbamic acid tert-butyl ester, which was then reacted with 4,4,4',4',5,5,5',5'-octamethyl-2,2'-bi(1,3,2-dioxaborolane) and (1,1'-bis-diphenylphosphino)-ferrocene)palladium-(II)dichloride (1:1 complex with CH2Cl2) and subsequently with 3-(2-bromo-4-chloro-6-fluoro-phenyl)-5-methyl-[1,2,4]oxadiazole (intermediate B-2) to give the title compound as light yellow solid. MS: 529.2 (MH+, 1Cl).

Example 45

1-Amino-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide

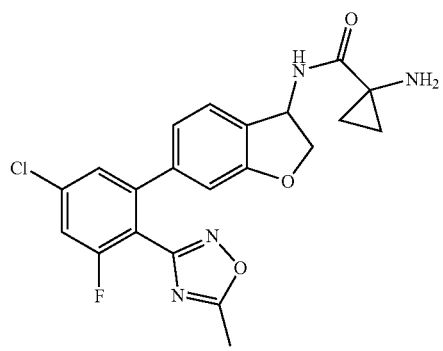 [SMILES: Cc1nc(-c2c(F)cc(Cl)cc2-c2ccc3c(c2)OCC3NC(=O)C2(N)CC2)no1]

In analogy to the procedure described for the preparation of intermediate A-11 [C], (1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-carbamic acid tert-butyl ester (example 44) has been treated with trifluoroacetic acid (90%) to give the title compound as light yellow oil. MS: 429.1 (MH+, 1Cl).

Example 46

Pyridazine-4-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide

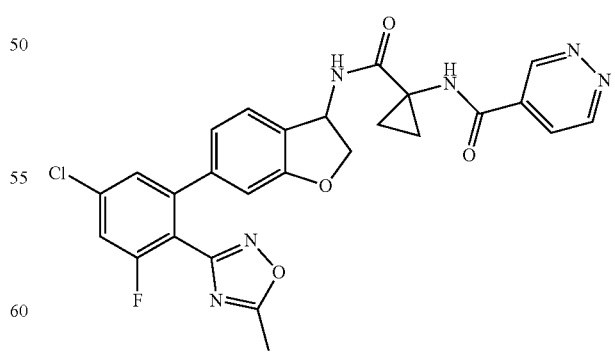

In analogy to the procedure described for the preparation of intermediate A-1 [B], 1-amino-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide (example 45) has been coupled with pyridazine-4-carboxylic acid to yield the title compound as yellow solid. MS: 535.1 (MH⁺, 1Cl).

Example 47

2-Methoxy-pyrimidine-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide

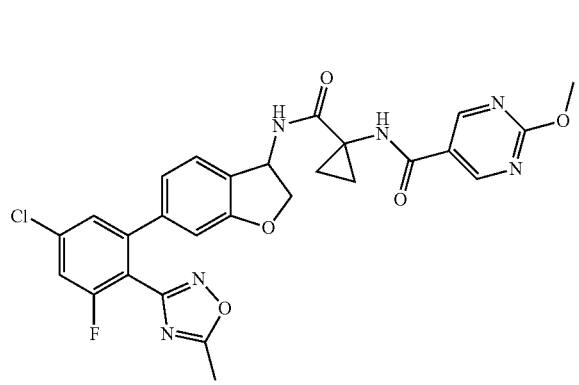 [SMILES: COc1ncc(C(=O)NC2(C(=O)NC3COc4cc(-c5cc(Cl)cc(F)c5-c5noc(C)n5)ccc43)CC2)cn1]

In analogy to the procedure described for the preparation of intermediate A-1 [B], 1-amino-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide (example 45) has been coupled with 2-methoxy-pyrimidine-5-carboxylic acid to yield the title compound as light yellow solid. MS: 565.1 (MH⁺, 1Cl).

Example 48

3-Methoxy-isoxazole-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide

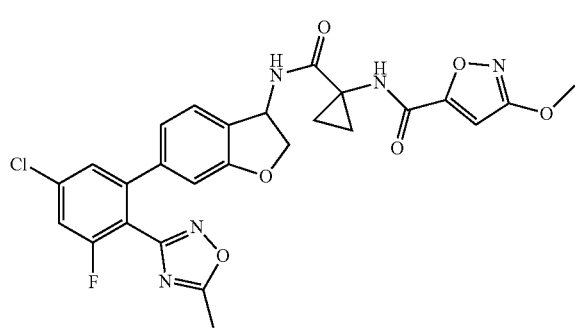 [SMILES: COc1cc(C(=O)NC2(C(=O)NC3COc4cc(-c5cc(Cl)cc(F)c5-c5noc(C)n5)ccc43)CC2)on1]

In analogy to the procedure described for the preparation of intermediate A-1 [B], 1-amino-cyclopropanecarboxylic acid{(rac)-6-[5-chloro-3-fluoro-2-(5-methyl-[1,2,4]oxadia-zol-3-yl)-phenyl]-2,3-dihydro-benzofuran-3-yl}-amide (example 45) has been coupled with 3-methoxy-isoxazole-5-carboxylic acid to yield the title compound as light yellow oil. MS: 554.1 (MH⁺, 1Cl).

Example 49

3-Amino-oxetane-3-carboxylic acid{(S)-5-[5-chloro-3-fluoro-2-(5-methyl-[1,2,4]oxadiazol-3-yl)-phenyl]-indan-1-yl}-amide

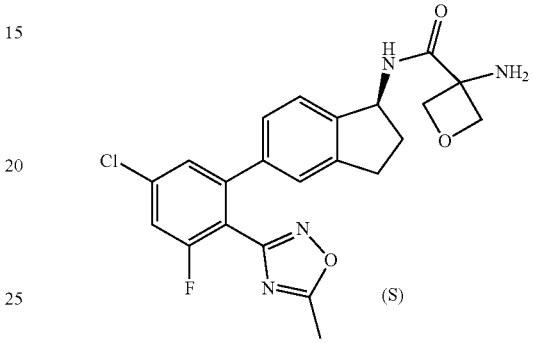

To a solution of (3-{(S)-5-[5-chloro-3-fluoro-2-(5-methyl-[1,2,4]oxadiazol-3-yl)-phenyl]-indan-1-ylcarbamoyl}-oxetan-3-yl)-carbamic acid 9H-fluoren-9-ylmethyl ester (intermediate A-12) (2.94 g, 4.42 mmol) in MeCl₂ (50.0 ml) was added piperidine (4.38 ml) and the mixture was stirred at room temperature for 15 h. The colorless solution was concentrated to dryness under high vacuum at RT. The remaining residue was purified by chromatography (silica gel; MeCl₂/MeOH 100:0-95:5) and the title compound was obtained as light brown oil (1.09 g, 56%). MS: 443.1 (MH⁺, 1Cl).

Example 50

Pyrimidine-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide

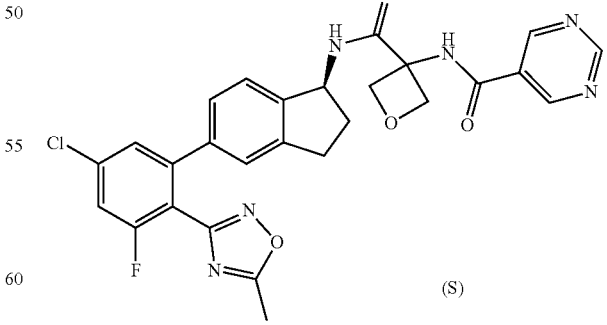

In analogy to the procedures described for the preparation of intermediate A-1 [B], 3-amino-oxetane-3-carboxylic acid {(S)-5-[5-chloro-3-fluoro-2-(5-methyl-[1,2,4]oxadiazol-3-yl)-phenyl]-indan-1-yl}-amide (example 49) was coupled with pyrimidine-5-carboxylic acid to yield the title compound as light yellow solid. MS: 549.1 (MH+, 1Cl).

Example 51

Isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide

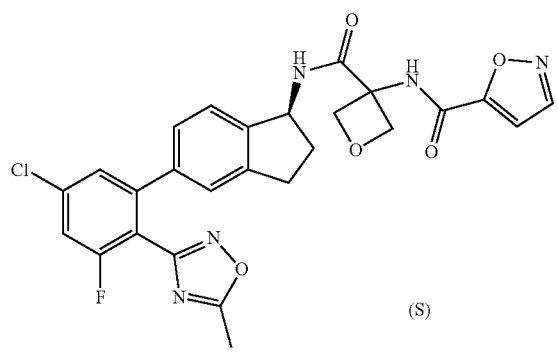 [SMILES: Cc1nc(-c2c(F)cc(Cl)cc2-c2ccc3c(c2)CC[C@@H]3NC(=O)C2(NC(=O)c3ccno3)COC2)no1 ; "(S)"]

In analogy to the procedures described for the preparation of intermediate A-1 [B], 3-amino-oxetane-3-carboxylic acid {(S)-5-[5-chloro-3-fluoro-2-(5-methyl-[1,2,4]oxadiazol-3-yl)-phenyl]-indan-1-yl}-amide (example 49) was coupled with isoxazole-5-carboxylic acid to yield the title compound as yellow oil. MS: 538.1 (MH+, 1Cl).

Example 52

3-Methyl-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide

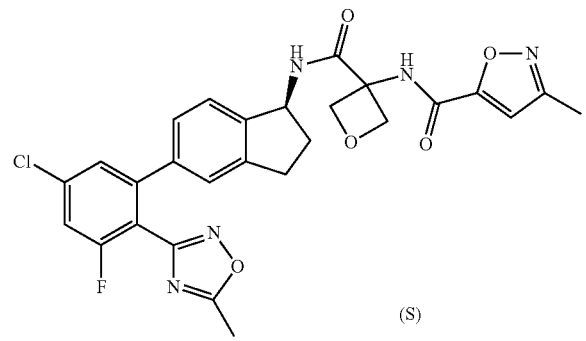 [SMILES: Cc1cc(C(=O)NC2(C(=O)N[C@H]3CCc4cc(-c5cc(Cl)cc(F)c5-c5noc(C)n5)ccc43)COC2)on1 ; "(S)"]

In analogy to the procedures described for the preparation of intermediate A-1 [B], 3-amino-oxetane-3-carboxylic acid {(S)-5-[5-chloro-3-fluoro-2-(5-methyl-[1,2,4]oxadiazol-3-yl)-phenyl]-indan-1-yl}-amide (example 49) was coupled with 3-methyl-isoxazole-5-carboxylic acid to yield the title compound as light yellow oil. MS: 552.1 (MH+, 1Cl).

Example 53

3-Methoxy-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide

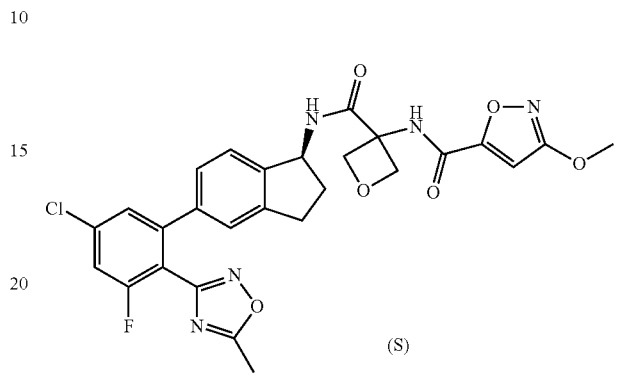

In analogy to the procedures described for the preparation of intermediate A-1 [B], 3-amino-oxetane-3-carboxylic acid {(S)-5-[5-chloro-3-fluoro-2-(5-methyl-[1,2,4]oxadiazol-3-yl)-phenyl]-indan-1-yl}-amide (example 49) was coupled with 3-methoxy-isoxazole-5-carboxylic acid to yield the title compound as light yellow viscous oil. MS: 568.1 (MH+, 1Cl).

Example 54

(1-{(rac)-3-[5-Chloro-3-fluoro-2-(2-methyl-2H-tetrazol-5-yl)-phenyl]-6,7-dihydro-5H-[1]pyrindin-7-ylcarbamoyl}-cyclopropyl)-carbamic acid tert-butyl ester

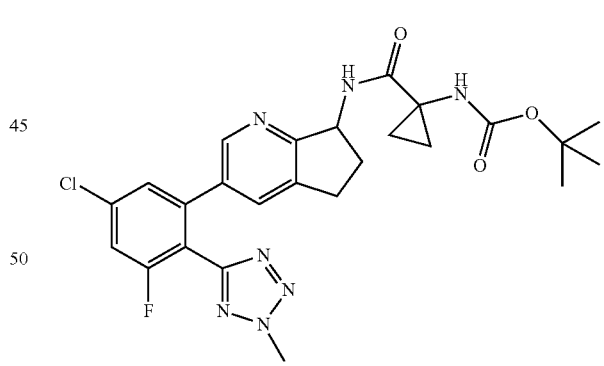

In analogy to the procedures described for the preparation of example 12, of intermediate A-11 [C] and for the preparation of intermediate A-1 [B], the title compound has been prepared by the following reaction sequence: i) ((rac)-3-bromo-6,7-dihydro-5H-[1]pyrindin-7-yl)-carbamic acid tert-butyl ester (example 36) has been reacted with 4,4,4',4',5,5,5',5'-octamethyl-2,2'-bi(1,3,2-dioxaborolane) and (1,1'-bis-diphenylphosphino)-ferrocene)palladium-(II)dichloride (1:1 complex with CH$_2$Cl$_2$) and subsequently with 5-(2-bromo-4-chloro-6-fluoro-phenyl)-2-methyl-2H-tetrazole (intermediate B-3) to give {(rac)-3-[5-chloro-3-fluoro-2-(2-methyl-2H-tetrazol-5-yl)-phenyl]-6,7-dihydro-5H-[1]pyrindin-7-yl}- carbamic acid tert-butyl ester; ii) removal of the BOC protective group to give (rac)-3-[5-chloro-3-fluoro-2-(2-methyl-2H-tetrazol-5-yl)-phenyl]-6,7-dihydro-5H-[1]pyrindin-7-ylamine; iii) coupling with 1-tert-butoxycarbonylamino-cyclopropanecarboxylic acid to yield the title compound as purple amorphous solid. MS: 528.2 (MH+, 1Cl).

Example 55

1-Amino-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide

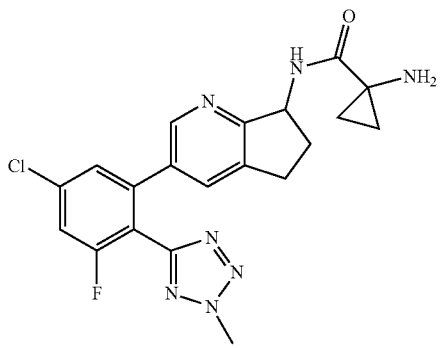 [SMILES: Cn1nnc(-c2c(F)cc(Cl)cc2-c2cnc3c(c2)CCC3NC(=O)C2(N)CC2)n1]

In analogy to the procedure described for the preparation of intermediate A-11 [C], (1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-carbamic acid tert-butyl ester (example 54) has been treated with trifluoroacetic acid (90%) to give the title compound as light brown amorphous solid. MS: 428.1 (MH+, 1Cl).

Example 56

2-Methoxy-pyrimidine-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide

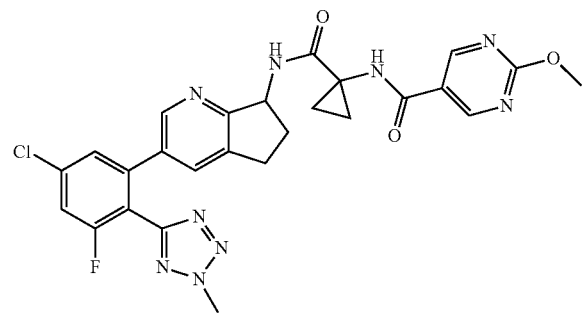 [SMILES: COc1ncc(C(=O)NC2(C(=O)NC3CCc4cc(-c5cc(Cl)cc(F)c5-c5nnn(C)n5)cnc43)CC2)cn1]

In analogy to the procedures described for the preparation of intermediate A-1 [B], 1-amino-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide (example 55) was coupled with 2-methoxy-pyrimidine-5-carboxylic acid to yield the title compound as light yellow solid. MS: 562.2 (M−H−, 1Cl).

Example 57

Isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide

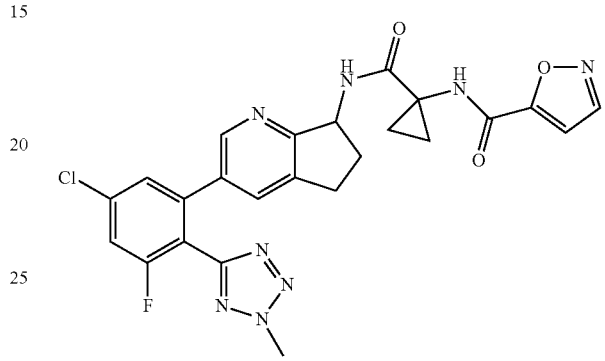

In analogy to the procedures described for the preparation of intermediate A-1 [B], 1-amino-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide (example 55) was coupled with isoxazole-5-carboxylic acid to yield the title compound as light yellow solid. MS: 523.1 (MH+, 1Cl).

Example 58

3-Methyl-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide

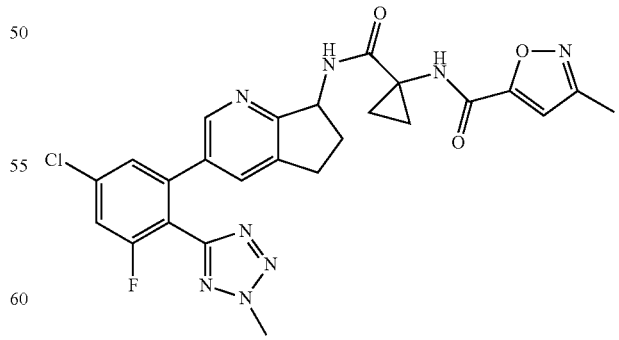

In analogy to the procedures described for the preparation of intermediate A-1 [B], 1-amino-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide (example 55) was coupled with 3-methyl-isoxazole-5-carboxylic acid to yield the title compound as light yellow solid. MS: 537.2 (MH+, 1Cl).

Example 59

3-Methoxy-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide

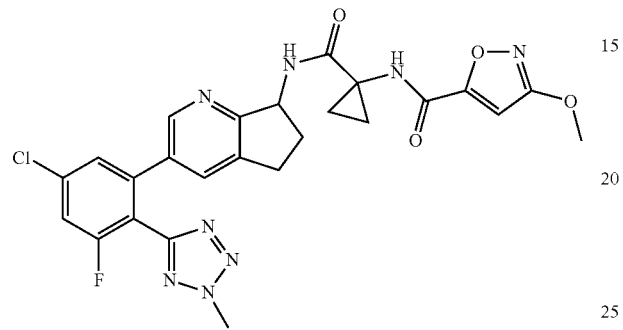

In analogy to the procedures described for the preparation of intermediate A-1 [B], 1-amino-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide (example 55) was coupled with 3-methoxy-isoxazole-5-carboxylic acid to yield the title compound as light yellow solid. MS: 553.2 (MH+, 1Cl).

Example 60

(1-{(rac)-6-[5-Chloro-3-fluoro-2-(2-methyl-2H-tetrazol-5-yl)-phenyl]-2,3-dihydro-benzo[b]thiophen-3-ylcarbamoyl}-cyclopropyl)-carbamic acid tert-butyl ester

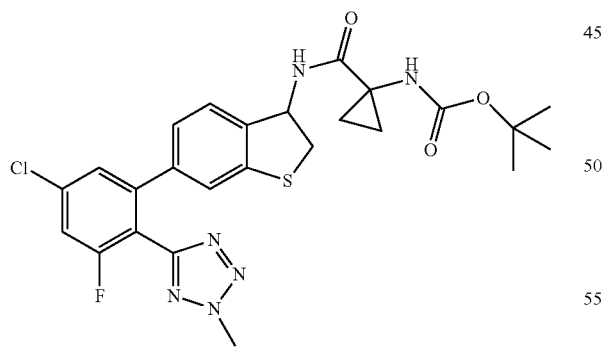

In analogy to the procedures described for the preparation of intermediates A-1 [B] and A-1 [C], and for the preparation of example 5, (rac)-6-bromo-2,3-dihydro-benzo[b]thiophen-3-ylamine (intermediate A-9 [A]) has been coupled with 1-tert-butoxycarbonylamino-cyclopropanecarboxylic acid to give [1-((rac)-6-bromo-2,3-dihydro-benzo[b]thiophen-3-ylcarbamoyl)-cyclopropyl]-carbamic acid tert-butyl ester, which was then reacted with 4,4,4',4',5,5,5',5'-octamethyl-2,2'-bi(1,3,2-dioxaborolane) and (1,1'-bis-diphenylphosphino)-ferrocene)palladium-(II)dichloride (1:1 complex with CH2Cl2) to give {1-[(rac)-6-(4,4,5,5-tetramethyl-[1,3,2]dioxaborolan-2-yl)-2,3-dihydro-benzo[b]thiophen-3-ylcarbamoyl]-cyclopropyl}-carbamic acid tert-butyl ester, which was then treated again with (1,1'-bis-diphenylphosphino)-ferrocene)palladium-(II)dichloride (1:1 complex with CH2Cl2) and 5-(2-bromo-4-chloro-6-fluoro-phenyl)-2-methyl-2H-tetrazole (intermediate B-3) to give the title compound as light yellow amorphous solid. MS: 545.2 (MH+, 1Cl).

Example 61

1-Amino-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide

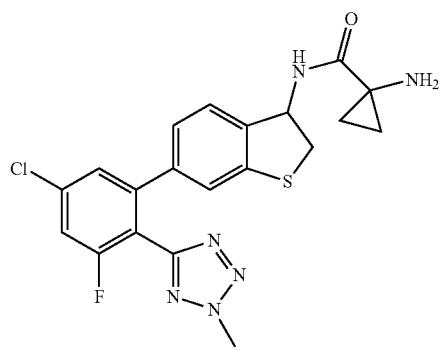 [SMILES: Cn1nnc(-c2c(F)cc(Cl)cc2-c2ccc3c(c2)SCC3NC(=O)C2(N)CC2)n1]

In analogy to the procedure described for the preparation of intermediate A-11 [C], (1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-carbamic acid tert-butyl ester (example 60) has been treated with trifluoroacetic acid (90%) to give the title compound as light yellow amorphous solid. MS: 445.1 (MH+, 1Cl).

Example 62

5-Methyl-[1,3,4]oxadiazole-2-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide

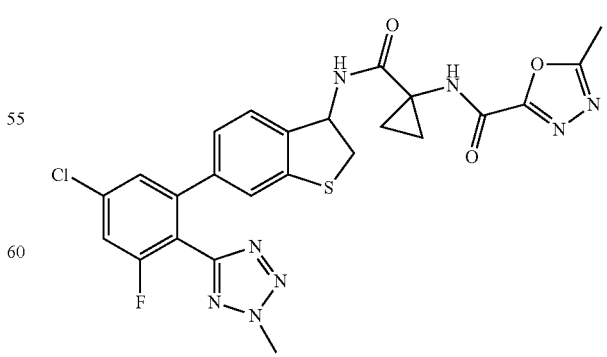

In analogy to the procedure described for the preparation of intermediate A-1 [B], 1-amino-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide (example 61) has been coupled with 5-methyl-[1,3,4]oxadiazole-2-carboxylic acid to yield the title compound as light yellow amorphous solid. MS: 555.1 (MH+, 1Cl).

Example 63

Pyrimidine-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide

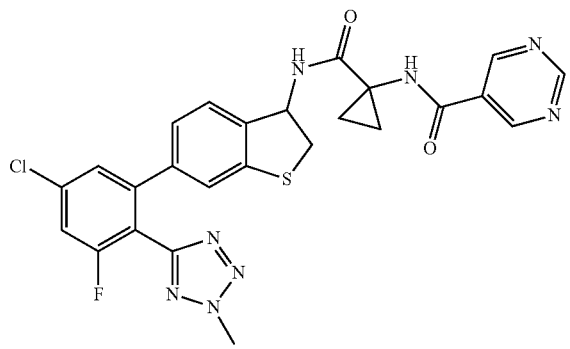 [SMILES: Cn1nnc(-c2c(F)cc(Cl)cc2-c2ccc3c(c2)SCC3NC(=O)C2(NC(=O)c3cncnc3)CC2)n1]

In analogy to the procedure described for the preparation of intermediate A-1 [B], 1-amino-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide (example 61) has been coupled with pyrimidine-5-carboxylic acid to yield the title compound as light yellow amorphous solid. MS: 551.1 (MH+, 1Cl).

Example 64

Isoxazole-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide

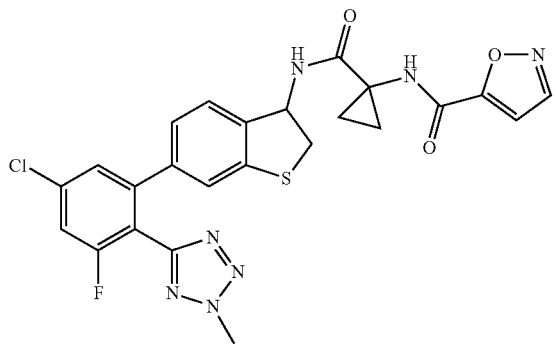 [SMILES: Cn1nnc(-c2c(F)cc(Cl)cc2-c2ccc3c(c2)SCC3NC(=O)C2(NC(=O)c3ccno3)CC2)n1]

In analogy to the procedure described for the preparation of intermediate A-1 [B], 1-amino-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide (example 61) has been coupled with isoxazole-5-carboxylic acid to yield the title compound as light yellow oil. MS: 540.1 (MH+, 1Cl).

Example 65

3-Methoxy-isoxazole-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide

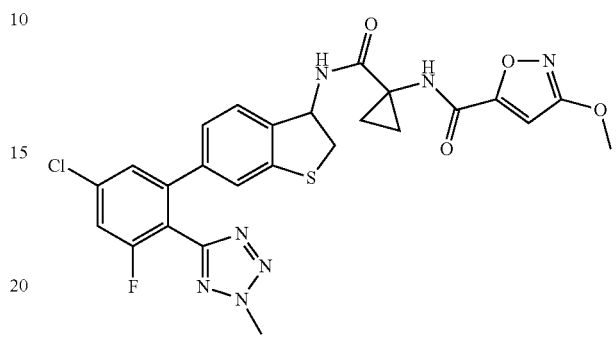

In analogy to the procedure described for the preparation of intermediate A-1 [B], 1-amino-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide (example 61) has been coupled with 3-methoxy-isoxazole-5-carboxylic acid to yield the title compound as light yellow oil. MS: 570.1 (MH+, 1Cl).

Example A

A compound of formula (I) can be used in a manner known per se as the active ingredient for the production of tablets of the following composition:

|  | Per tablet |
|---|---|
| Active ingredient | 200 mg |
| Micro crystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound according to formula (I)

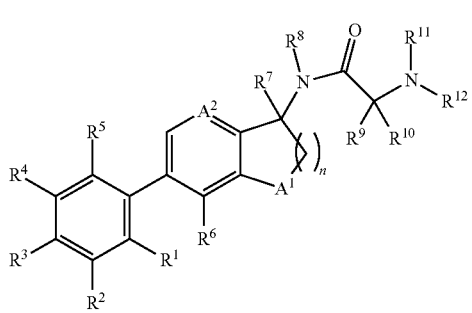

wherein
R$^1$ is selected from the group consisting of alkyl, cycloalkyl, cycloalkylalkyl, alkoxy, alkoxyalkyl, cycloalkoxy, cycloalkoxyalkyl, haloalkyl, haloalkoxy, haloalkoxyalkyl, halocycloalkyl, halocycloalkylalkyl, halocycloalkoxy, halocycloalkoxyalkyl, alkoxycarbonyl, cycloalkoxycarbonyl, haloalkoxycarbonyl, halocycloalkoxycarbonyl, cyano, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, alkoxy, alkoxyalkyl, haloalkoxy, alkoxyalkoxy, alkoxyalkoxyalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;
R$^2$ is selected from the group consisting of hydrogen, alkyl, haloalkyl, alkoxy, cycloalkyl, cyano and halogen;
R$^3$ is selected from the group consisting of hydrogen, alkyl, haloalkyl, alkoxy, cycloalkyl, cyano and halogen;
R$^4$ is selected from the group consisting of hydrogen, alkyl, haloalkyl, alkoxy, cycloalkyl, cyano and halogen;
R$^5$ is selected from the group consisting of hydrogen, alkyl, haloalkyl, alkoxy, cycloalkyl, cyano and halogen;
R$^6$ is selected from the group consisting of hydrogen, alkyl, haloalkyl, alkoxy, cycloalkyl, cyano and halogen;
R$^7$ is selected from the group consisting of hydrogen, alkyl and cycloalkyl;
R$^8$ is selected from the group consisting of hydrogen, alkyl and cycloalkyl;
R$^9$ and R$^{10}$ together with the carbon they are attached to form a cycloalkyl or a oxetanyl;
R$^{11}$ is selected from the group consisting of hydrogen, alkyl and cycloalkyl;
R$^{12}$ is selected from the group consisting of hydrogen, alkyl, cycloalkyl and —C(O)—R$^{13}$;
R$^{13}$ is selected from the group consisting of alkyl, cycloalkyl, cycloalkylalkyl, alkoxy, alkoxyalkoxy, cycloalkoxy, halocycloalkoxy, alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;
R$^{14}$ is selected from the group consisting of hydrogen, alkyl, alkoxy and cycloalkyl;
R$^{15}$ is selected from the group consisting of hydrogen, alkyl and cycloalkyl;
R$^{16}$ is selected from the group consisting of hydrogen, alkyl, haloalkyl, alkoxy, cycloalkyl, cyano and halogen;
A$^1$ is selected from the group consisting of CR$^{14}$, O, and S;
A$^2$ is CR$^{16}$ or N; and
n is 1;
or a pharmaceutically acceptable salt thereof.
2. A compound according to claim 1, wherein R$^1$ is selected from the group consisting of haloalkoxy, alkoxycarbonyl, cycloalkoxycarbonyl, haloalkoxycarbonyl, heteroaryl and substituted heteroaryl, wherein substituted heteroaryl is substituted with one to three alkyl.
3. A compound according to claim 1, wherein R$^2$ is hydrogen or halogen.
4. A compound according to claim 1, wherein R$^3$ is hydrogen.
5. A compound according to claim 1, wherein R$^4$ is hydrogen or halogen.
6. A compound according to claim 1, wherein R$^5$ is hydrogen.
7. A compound according to claim 1, wherein R$^6$ is hydrogen.
8. A compound according to claim 1, wherein R$^7$ is hydrogen or alkyl.
9. A compound according to claim 1, wherein R$^8$ is hydrogen.
10. A compound according to claim 1, wherein R$^{11}$ is hydrogen.
11. A compound according to claim 1, wherein R$^{12}$ is selected from the group consisting of hydrogen, alkyl and cycloalkyl.
12. A compound according to claim 1, wherein R$^{12}$ is —C(O)—R$^{13}$.
13. A compound according to claim 1, wherein R$^{13}$ is selected from the group consisting of
alkoxy, alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, halogen, cyano, haloalkyl, alkoxy, alkoxyalkyl, amino and substituted amino, wherein substituted amino is substituted with one to two substituents independently selected from alkyl and cycloalkyl.
14. A compound according to claim 1, wherein A$^2$ is CR$^{16}$.
15. A compound according to claim 1, wherein A$^2$ is N.
16. A compound according to claim 1, wherein R$^{14}$ is hydrogen.

17. A compound according to claim 1, wherein $R^{15}$ is hydrogen.

18. A compound according to claim 1, wherein $R^{16}$ is hydrogen or halogen.

19. A compound according to claim 1, selected from the group consisting of
- (rac)-2-(1-{[1-(2,2,2-Trifluoro-acetylamino)-cyclopropanecarbonyl]-amino}-indan-5-yl)-benzoic acid methyl ester;
- 1-(2,2,2-Trifluoro-acetylamino)-cyclopropanecarboxylic acid{(rac)-5-[3,5-dichloro-2-(2,2-difluoro-ethoxy)-phenyl]-indan-1-yl}-amide;
- (rac)-2-Chloro-6-(1-{[1-(2,2,2-trifluoro-acetylamino)-cyclopropanecarbonyl]-amino}-indan-5-yl)-benzoic acid methyl ester;
- 1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-indan-1-yl}-amide;
- 1-(2,2,2-Trifluoro-acetylamino)-cyclopropanecarboxylic acid{(S)-5-[5-chloro-3-fluoro-2-(5-methyl-[1,2,4]oxadiazol-3-yl)-phenyl]-indan-1-yl}-amide;
- 2-Chloro-6-((S)-1-{[3-(2,2,2-trifluoro-acetylamino)-oxetane-3-carbonyl]-amino}-indan-5-yl)-benzoic acid methyl ester;
- 3-(2,2,2-Trifluoro-acetylamino)-oxetane-3-carboxylic acid{(S)-5-[5-chloro-3-fluoro-2-(5-methyl-[1,2,4]oxadiazol-3-yl)-phenyl]-indan-1-yl}-amide;
- 3-(2,2,2-Trifluoro-acetylamino)-oxetane-3-carboxylic acid{(S)-5-[5-chloro-3-fluoro-2-(2-methyl-2H-tetrazol-5-yl)-phenyl]-indan-1-yl}-amide;

and pharmaceutically-acceptable salts thereof.

20. A compound according to claim 1, selected from the group consisting of
- 1-(2,2,2-Trifluoro-acetylamino)-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide;
- 1-(2,2,2-Trifluoro-acetylamino)-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl-}amide;
- 1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-7-fluoro-indan-1-yl-}amide;
- 1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-1-methyl-indan-1-yl}-amide;
- 1-(2,2,2-Trifluoro-acetylamino)-cyclopropanecarboxylic acid{5-[5-chloro-3-fluoro-2-(2-methyl-2H-tetrazol-5-yl)-phenyl]-1-methyl-indan-1-yl}-amide;
- 1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide;
- 1-(2,2,2-Trifluoro-acetylamino)-cyclopropanecarboxylic acid{(rac)-6-[5-chloro-3-fluoro-2-(2-methyl-2H-tetrazol-5-yl)-phenyl]-2,3-dihydro-benzofuran-3-yl}-amide;

and pharmaceutically acceptable salts thereof.

21. A compound according to claim 1, selected from the group consisting of
- 1-(2,2,2-Trifluoro-acetylamino)-cyclopropanecarboxylic acid{(rac)-6-[5-chloro-3-fluoro-2-(5-methyl-[1,2,4]oxadiazol-3-yl)-phenyl]-2,3-dihydro-benzo[b]thiophen-3-yl}-amide;
- 1-(2,2,2-Trifluoro-acetylamino)-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide;
- (1-{(S)-5-[5-Chloro-3-fluoro-2-(5-methyl-[1,2,4]oxadiazol-3-yl)-phenyl]-indan-1-ylcarbamoyl}-cyclopropyl)-carbamic acid tert-butyl ester;
- 1-Amino-cyclopropanecarboxylic acid{(S)-5-[5-chloro-3-fluoro-2-(5-methyl-[1,2,4]oxadiazol-3-yl)-phenyl]-indan-1-yl}-amide;
- Pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
- 2-Methoxy-pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
- Pyridazine-4-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
- Isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
- 5-Methyl-[1,3,4]oxadiazole-2-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;
- 3-Methoxy-isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;

and pharmaceutically acceptable salts thereof.

22. A compound according to claim 1, selected from the group consisting of
- (1-{(rac)-5-[5-Chloro-3-fluoro-2-(5-methyl-[1,2,4]oxadiazol-3-yl)-phenyl]-7-fluoro-indan-1-ylcarbamoyl}-cyclopropyl)-carbamic acid tert-butyl ester;
- 1-Amino-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide;
- 2-Methoxy-pyrimidine-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;
- Pyridazine-4-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;
- 3-Methoxy-isoxazole-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;
- (1-{(rac)-3-[5-Chloro-3-fluoro-2-(5-methyl-[1,2,4]oxadiazol-3-yl)-phenyl]-6,7-dihydro-5H-[1]pyrindin-7-ylcarbamoyl}-cyclopropyl)-carbamic acid tert-butyl ester;
- 1-Amino-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide;
- 3-Methoxy-isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
- Pyridazine-4-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;
- Pyridazine-4-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

and pharmaceutically acceptable salts thereof.

23. A compound according to claim 1, selected from the group consisting of

Pyridazine-4-carboxylic acid(1-{(S or R)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

2-Methoxy-pyrimidine-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

Isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

(1-{(rac)-6-[5-Chloro-3-fluoro-2-(5-methyl-[1,2,4]oxadiazol-3-yl)-phenyl]-2,3-dihydro-benzofuran-3-ylcarbamoyl}-cyclopropyl)-carbamic acid tert-butyl ester;

1-Amino-cyclopropanecarboxylic acid{(rac)-6-[5-chloro-3-fluoro-2-(5-methyl-[1,2,4]oxadiazol-3-yl)-phenyl]-2,3-dihydro-benzofuran-3-yl}-amide;

Pyridazine-4-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

2-Methoxy-pyrimidine-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

3-Methoxy-isoxazole-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

3-Amino-oxetane-3-carboxylic acid{(S)-5-[5-chloro-3-fluoro-2-(5-methyl-[1,2,4]oxadiazol-3-yl)-phenyl]-indan-1-yl}-amide;

Pyrimidine-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

and pharmaceutically acceptable salts thereof.

24. A compound according to claim 1, selected from the group consisting of

Isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

3-Methyl-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

3-Methoxy-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

(1-{(rac)-3-[5-Chloro-3-fluoro-2-(2-methyl-2H-tetrazol-5-yl)-phenyl]-6,7-dihydro-5H-[1]pyrindin-7-ylcarbamoyl}-cyclopropyl)-carbamic acid tert-butyl ester;

1-Amino-cyclopropanecarboxylic acid{(rac)-3-[5-chloro-3-fluoro-2-(2-methyl-2H-tetrazol-5-yl)-phenyl]-6,7-dihydro-5H-[1]pyrindin-7-yl}-amide;

2-Methoxy-pyrimidine-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

Isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

3-Methyl-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

3-Methoxy-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

(1-{(rac)-6-[5-Chloro-3-fluoro-2-(2-methyl-2H-tetrazol-5-yl)-phenyl]-2,3-dihydro-benzo[b]thiophen-3-ylcarbamoyl}-cyclopropyl)-carbamic acid tert-butyl ester;

and pharmaceutically acceptable salts thereof.

25. A compound according to claim 1, selected from the group consisting of

1-Amino-cyclopropanecarboxylic acid{(rac)-6-[5-chloro-3-fluoro-2-(2-methyl-2H-tetrazol-5-yl)-phenyl]-2,3-dihydro-benzo[b]thiophen-3-yl}-amide;

5-Methyl-[1,3,4]oxadiazole-2-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

Pyrimidine-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

Isoxazole-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

3-Methoxy-isoxazole-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

and pharmaceutically acceptable salts thereof.

26. A compound according to claim 1, selected from the group consisting of 1-(2,2,2-Trifluoro-acetylamino)-cyclopropanecarboxylic acid{(S)-5-[5-chloro-3-fluoro-2-(5-methyl-[1,2,4]oxadiazol-3-yl)-phenyl]-indan-1-yl}-amide;

1-(2,2,2-Trifluoro-acetylamino)-cyclopropanecarboxylic acid{(rac)-3-[5-chloro-3-fluoro-2-(5-methyl-[1,2,4]oxadiazol-3-yl)-phenyl]-6,7-dihydro-5H-[1]pyrindin-7-yl}-amide;

1-(2,2,2-Trifluoro-acetylamino)-cyclopropanecarboxylic acid{(rac)-5-[5-chloro-3-fluoro-2-(5-methyl-[1,2,4]oxadiazol-3-yl)-phenyl]-7-fluoro-indan-1-yl}-amide;

2-Methoxy-pyrimidine-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;

Pyridazine-4-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;

3-Methoxy-isoxazole-5-carboxylic acid(1-{(S)-5-[5-chloro-3-fluoro-2-(5-methyl-[1,2,4]oxadiazol-3-yl)-phenyl]-indan-1-ylcarbamoyl}-cyclopropyl)-amide;

and pharmaceutically acceptable salts thereof.

27. A compound according to claim 1, selected from the group consisting of

2-Methoxy-pyrimidine-5-carboxylic acid(1-{(rac)-5-[5-chloro-3-fluoro-2-(5-methyl-[1,2,4]oxadiazol-3-yl)-phenyl]-7-fluoro-indan-1-ylcarbamoyl}-cyclopropyl)-amide;

3-Methoxy-isoxazole-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

2-Methoxy-pyrimidine-5-carboxylic acid(1-{(rac)-3-[5-chloro-3-fluoro-2-(5-methyl-[1,2,4]oxadiazol-3-yl)-phenyl]-6,7-dihydro-5H-[1]pyrindin-7-ylcarbamoyl}-cyclopropyl)-amide;

2-Methoxy-pyrimidine-5-carboxylic acid(1-{(rac)-6-[5-chloro-3-fluoro-2-(5-methyl-[1,2,4]oxadiazol-3-yl)-phenyl]-2,3-dihydro-benzofuran-3-ylcarbamoyl}-cyclopropyl)-amide;

3-Methoxy-isoxazole-5-carboxylic acid (3-{(S)-5-[5-chloro-3-fluoro-2-(5-methyl-[1,2,4]oxadiazol-3-yl)-phenyl]-indan-1-ylcarbamoyl}-oxetan-3-yl)-amide;

2-Methoxy-pyrimidine-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

3-Methoxy-isoxazole-5-carboxylic acid(1-{(rac)-3-[5-chloro-3-fluoro-2-(2-methyl-2H-tetrazol-5-yl)-phenyl]-6,7-dihydro-5H-[1]pyrindin-7-ylcarbamoyl}-cyclopropyl)-amide;

Pyrimidine-5-carboxylic acid(1-{(rac)-6-[5-chloro-3-fluoro-2-(2-methyl-2H-tetrazol-5-yl)-phenyl]-2,3-dihydro-benzo[b]thiophen-3-ylcarbamoyl}-cyclopropyl)-amide;

and pharmaceutically acceptable salts thereof.

28. A pharmaceutical composition comprising a compound according to claim 1 and a therapeutically inert carrier.

29. A compound according to claim 21 which is pyridazine-4-carboxylic acid(1-{(S)-5-[5-chloro-3-fluoro-2-(5-methyl-[1,2,4]oxodiazol-3yl)-phenyl]indan-1-ylcarbamoyl}-cyclopropyl-amide and pharmaceutically acceptable salts thereof.

* * * * *